US009770454B2

(12) United States Patent
Reuveni et al.

(10) Patent No.: US 9,770,454 B2
(45) Date of Patent: Sep. 26, 2017

(54) IGF-1R SIGNALING PATHWAY INHIBITORS USEFUL IN THE TREATMENT OF NEURODEGENERATIVE DISEASES

(71) Applicant: YISSUM RESEARCH DEVELOPMENT COMPANY OF THE HEBREW UNIVERSITY OF JERUSALEM, LTD., Jerusalem (IL)

(72) Inventors: Hadas Reuveni, Har Adar (IL); Ehud Cohen, Jerusalem (IL); Alexander Levitzki, Jerusalem (IL); Shmuel Ben-Sasson, Jerusalem (IL)

(73) Assignee: Yissum Research Development Company of the Hebrew University of Jerusalem, Ltd., Jerusalem (IL)

( * ) Notice: Subject to any disclaimer, the term of this patent is extended or adjusted under 35 U.S.C. 154(b) by 0 days.

(21) Appl. No.: 14/904,787

(22) PCT Filed: Jul. 13, 2014

(86) PCT No.: PCT/IB2014/063071
§ 371 (c)(1),
(2) Date: Jan. 13, 2016

(87) PCT Pub. No.: WO2015/008206
PCT Pub. Date: Jan. 22, 2015

(65) Prior Publication Data
US 2016/0158243 A1 Jun. 9, 2016

Related U.S. Application Data

(60) Provisional application No. 61/846,014, filed on Jul. 14, 2013.

(51) Int. Cl.
*A61K 31/5415* (2006.01)
*A61K 31/165* (2006.01)
*C07D 279/08* (2006.01)

(52) U.S. Cl.
CPC ........ *A61K 31/5415* (2013.01); *A61K 31/165* (2013.01); *C07D 279/08* (2013.01)

(58) Field of Classification Search
CPC . A61K 31/5415; A61K 31/165; C07D 279/08
See application file for complete search history.

(56) References Cited

U.S. PATENT DOCUMENTS

| 5,217,999 | A | 6/1993 | Levitzki |
| 5,302,606 | A | 4/1994 | Spada |
| 5,691,362 | A | 11/1997 | McCormick |
| 5,773,476 | A * | 6/1998 | Chen ............... A61K 31/245 514/618 |
| 5,789,427 | A | 8/1998 | Chen |
| 6,020,332 | A | 2/2000 | Li |
| 6,225,335 | B1 | 5/2001 | Tang |
| 6,525,046 | B1 | 2/2003 | Cirillo |
| 8,058,309 | B2 | 11/2011 | Reuveni |
| 2002/0068687 | A1 | 6/2002 | Chen |
| 2004/0127555 | A1 | 7/2004 | Snow |
| 2004/0197335 | A1 | 10/2004 | Slavin |
| 2009/0143397 | A1 | 6/2009 | Kuo |
| 2012/0083528 | A1 | 4/2012 | Reuveni |

FOREIGN PATENT DOCUMENTS

| CN | 1155977 | 8/1997 |
| CN | 1167568 | 12/1997 |
| EP | 0860438 | 1/2003 |
| EP | 1340500 | 9/2003 |
| JP | 2005-513100 | 5/2005 |
| JP | 2005-516983 | 6/2005 |
| WO | 95/24190 | 9/1995 |
| WO | 97/45111 | 12/1997 |
| WO | 97/45400 | 12/1997 |
| WO | 99/24442 | 5/1999 |
| WO | 00/43384 | 7/2000 |
| WO | 01/068593 | 9/2001 |
| WO | 03/045378 | 6/2003 |
| WO | 03/053425 | 7/2003 |
| WO | 03/072570 | 9/2003 |
| WO | 2004/030627 | 4/2004 |
| WO | 2005/068414 | 7/2005 |
| WO | 2005/077942 | 8/2005 |
| WO | 2005/094376 | 10/2005 |
| WO | 2006/098554 | 9/2006 |
| WO | 2007/072041 | 6/2007 |
| WO | 2008/028314 | 3/2008 |

(Continued)

OTHER PUBLICATIONS

Aaronson (1991) Growth factors and cancer. Science 254(5035): 1146-53.
Bäckström et al., (1989) Synthesis of some novel potent and selective catechol O-methyltransferase inhibitors. J Med Chem 32(4): 841-6.
Balch et al., (2008) Adapting proteostasis for disease intervention. Science 319(5865): 916-9.
Baserga (2009) The insulin receptor substrate-1: a biomarker for cancer? Exp Cell Res 315(5): 727-32.
Berge et al., (1977) Pharmaceutical salts. J Pharm Sci 66(1): 1-19.
Blum et al., (2000) Substrate competitive inhibitors of IGF-1 receptor kinase. Biochemistry 39(51): 15705-12.
Bollag et al., (2010) Clinical efficacy of a RAF inhibitor needs broad target blockade in BRAF-mutant melanoma. Nature 467(7315): 596-9.
Boura-Halfon and Zick (2009) Serine kinases of insulin receptor substrate proteins. Vitam Horm 80: 313-49.
Buchwald et al., (1980) Long-term, continuous intravenous heparin administration by an implantable infusion pump in ambulatory patients with recurrent venous thrombosis. Surgery 88(4): 507-16.

(Continued)

*Primary Examiner* — Sudhakar Katakam
(74) *Attorney, Agent, or Firm* — Rothwell, Figg, Ernst & Manbeck, P.C.

(57) ABSTRACT

The present invention provides compounds acting as Insulin/IGF signaling modulators useful in the treatment of neurodegenerative diseases and disorders. The invention provides pharmaceutical compositions including such compounds, and methods of using these compounds and compositions for the treatment of neurodegenerative diseases, in particular neurodegenerative diseases caused by proteotoxicity such as Alzheimer's disease.

12 Claims, 11 Drawing Sheets

(56) References Cited

FOREIGN PATENT DOCUMENTS

| | | |
|---|---|---|
| WO | 2008/068751 | 6/2008 |
| WO | 2009/147682 | 12/2009 |
| WO | 2010/075511 | 7/2010 |
| WO | 2012/090204 | 7/2012 |

OTHER PUBLICATIONS

Buck et al., (2008) Feedback mechanisms promote cooperativity for small molecule inhibitors of epidermal and insulin-like growth factor receptors. Cancer Res 68(20): 8322-32.
Cardone et al., (1998) Regulation of cell death protease caspase-9 by phosphorylation. Science 282(5392): 1318-21.
Cohen and Dillin (2008) The insulin paradox: aging, proteotoxicity and neurodegeneration. Nat Rev Neurosci 9(10): 759-67.
Cohen et al., (2006) Opposing activities protect against age-onset proteotoxicity. Science 313(5793):1604-10.
Cohen et al., (2009) Reduced IGF-1 signaling delays age-associated proteotoxicity in mice. Cell 139(6): 1157-69.
Cohen et al., (2010) Temporal requirements of insulin/IGF-1 signaling for proteotoxicity protection. Aging Cell 9: 126-34.
Crose and Linardic (2011) Receptor tyrosine kinases as therapeutic targets in rhabdomyosarcoma. Sarcoma. 2011: 756982; 11 pages.
Dillin et al., (2002) Timing requirements for insulin/IGF-1 signaling in C. elegans. Science 298(5594): 830-4.
El-Ami et al., (2014) A novel inhibitor of the insulin/IGF signaling pathway protects from age-onset, neurodegeneration-linked proteotoxicity. Aging Cell 13(1): 165-74.
Favelyukis et al., (2001) Structure and autoregulation of the insulin-like growth factor 1 receptor kinase. Nat Struct Biol 8(12): 1058-63.
Flachsbart et al., (2009) Association of FOXO3A variation with human longevity confirmed in German centenarians. Proc Natl Acad Sci U S A 106(8): 2700-5.
Flaherty et al., (2010) Inhibition of mutated, activated BRAF in metastatic melanoma. N Engl J Med 363(9): 809-19.
Frei and Eder; Section 11: Chemotherapy; Chapter 44. Principles of Dose, Schedule, and Combination Therapy. In: Holland-Frei Cancer Medicine, 6th edition; edited by: Kufe DW, Pollock RE, Weichselbaum RR, Bast RC, Gansler TS, HollandJF and Frei E. Hamilton (ON): BC Decker; 2003, pp. 669-677.
Gazit et al., (1989) Tyrphostins I: synthesis and biological activity of protein tyrosine kinase inhibitors. J Med Chem 32(10): 2344-52.
Gazit et al., (1991) Tyrphostins. II. Heterocyclic and .alpha.-substituted benzylidenemalononitrile tyrphostins as potent inhibitors of EGF receptor and ErbB2/neu tyrosine kinases. J Med Chem 34(6): 1896-1907.
Goodson JM (1984) Dental Applications. In: Medical Applications of Controlled Release, vol. 2; CRC Press, Boca Raton, FL. pp. 115-138.
Holzenberger et al., (2003) IGF-1 receptor regulates lifespan and resistance to oxidative stress in mice. Nature 421(6919): 182-7.
Hsu et al., (2003) Regulation of aging and age-related disease by DAF-16 and heat-shock factor. Science 300(5622): 1142-5.
Hu et al., (2000) Rho(0) tumor cells: a model for studying whether mitochondria are targets for rhodamine 123, doxorubicin, and other drugs. Biochem Pharmacol 60(12): 1897-905.
Kaplan et al., (1990) Effects of 2-deoxyglucose on drug-sensitive and drug-resistant human breast cancer cells: toxicity and magnetic resonance spectroscopy studies of metabolism. Cancer Res 50(3): 544-51.
Keniry and Parsons (2011) mTOR inhibition, the second generation: ATP-competitive mTOR inhibitor initiates unexpected receptor tyrosine kinase-driven feedback loop. Cancer Discov 1(3): 203-4.
Kenyon (2005) The plasticity of aging: insights from long-lived mutants. Cell 120(4): 449-60.
Kenyon et al., (1993) A C. elegans mutant that lives twice as long as wild type. Nature 366(6454): 461-4.
Kolho et al., (1993) Hepatitis C antibodies in dialysis patients and patients with leukaemia. J Med Virol 40(4): 318-21.
Langer (1990) New methods of drug delivery. Science 249(4976): 1527-33.
Levitzki (1990) Tyrphostins—potential antiproliferative agents and novel molecular tools. Biochem Pharmacol 40(5): 913-8.
Levitzki (1992) Tyrphostins: tyrosine kinase blockers as novel antiproliferative agents and dissectors of signal transduction. FASEB J 6(14): 3275-82.
Levitzki and Gazit (1995) Tyrosine kinase inhibition: an approach to drug development. Science 267(5205): 1782-8.
Li et al., (2009) Inhibition of the insulin-like growth factor-1 receptor (IGF1R) tyrosine kinase as a novel cancer therapy approach. J Med Chem 52(16): 4981-5004.
Link (1995) Expression of human beta-amyloid peptide in transgenic Caenorhabditis elegans. Proc Natl Acad Sci U S A 92(20): 9368-9372.
Link et al., (1999) Direct observation of stress response in Caenorhabditis elegans using a reporter transgene. Cell Stress Chaperones 4(4): 235-42.
Liu et al., (2001) Hypersensitization of tumor cells to glycolytic inhibitors. Biochemistry 40(18): 5542-7.
Liu et al., (2002) Hypoxia increases tumor cell sensitivity to glycolytic inhibitors: a strategy for solid tumor therapy (Model C). Biochem Pharmacol 64(12): 1745-51.
Mazumder et al., (1995) Effects of tyrphostins, protein kinase inhibitors, on human immunodeficiency virus type 1 integrase. Biochemistry 34(46): 15111-22.
McColl et al., (2010) Insulin-like signaling determines survival during stress via posttranscriptional mechanisms in C. elegans. Cell Metab 12(3): 260-72.
Morley et al., (2002) The threshold for polyglutamine-expansion protein aggregation and cellular toxicity is dynamic and influenced by aging in Caenorhabditis elegans. Proc Natl Acad Sci U S A 99(16): 10417-22.
Murakami and Johnson (1996) A genetic pathway conferring life extension and resistance to UV stress in Caenorhabditis elegans. Genetics 143(3): 1207-18.
Murphy et al., (2003) Genes that act downstream of DAF-16 to influence the lifespan of Caenorhabditis elegans. Nature 424(6946): 277-83.
Oliveira et al., (2008) Antineoplastic effect of rapamycin is potentiated by inhibition of IRS-1 signaling in prostate cancer cells xenografts. J Cancer Res Clin Oncol 134(8): 833-9.
O'Reilly et al., (2006) mTOR inhibition induces upstream receptor tyrosine kinase signaling and activates Akt. Cancer Res 66(3): 1500-8.
Posner et al., (1994) Kinetics of inhibition by tyrphostins of the tyrosine kinase activity of the epidermal growth factor receptor and analysis by a new computer program. Mol Pharmacol 45(4): 673-83.
Reuveni et al., (2013) Therapeutic destruction of insulin receptor substrates for cancer treatment. Cancer Res 73(14): 4383-94.
Ryan and Goss (2008) The emerging role of the insulin-like growth factor pathway as a therapeutic target in cancer. Oncologist 13(1): 16-24.
Saudek et al., (1989) A preliminary trial of the programmable implantable medication system for insulin delivery. N Engl J Med 321(9): 574-9.
Schlessinger (1988) Signal transduction by allosteric receptor oligomerization. Trends Biochem Sci 13(11): 443-7.
Schlessinger and Ullrich (1992) Growth factor signaling by receptor tyrosine kinases. Neuron 9(3): 383-91.
Scott et al., (1992) Chimeric prion protein expression in cultured cells and transgenic mice. Protein Sci 1(8): 986-97.
Selkoe (2003) Folding proteins in fatal ways. Nature 426(6968): 900-4.
Snutch et al., (1988) The Caenorhabditis elegans hsp70 gene family: a molecular genetic characterization. Gene 64(2): 241-55.
Steiner et al., (2007) ATP non-competitive IGF-1 receptor kinase inhibitors as lead anti-neoplastic and anti-papilloma agents. Eur J Pharmacol 562(1-2): 1-11.
Suh et al., (2008) Functionally significant insulin-like growth factor I receptor mutations in centenarians. Proc Natl Acad Sci U S A 105(9): 3438-42.
Taguchi et al., (2007) Brain IRS2 signaling coordinates life span and nutrient homeostasis. Science 317(5836): 369-72.

(56) References Cited

OTHER PUBLICATIONS

Teixeira-Castro et al., (2011) Neuron-specific proteotoxicity of mutant ataxin-3 in C. elegans: rescue by the DAF-16 and HSF-1 pathways. Hum Mol Genet 20(15): 2996-3009.

Ting and Morris (1978) Reactivity of autolymphocytotoxic antibodies from dialysis patients with lymphocytes from chronic lymphocytic leukemia (CLL) patients. Transplantation 25(1): 31-3.

Ullrich and Schlessinger (1990) Signal transduction by receptors with tyrosine kinase activity. Cell 61(2): 203-12.

van Ham et al., (2010) Identification of MOAG-4/SERF as a regulator of age-related proteotoxicity. Cell 142(4): 601-12.

Villanueva et al., (2010) Acquired resistance to BRAF inhibitors mediated by a RAF kinase switch in melanoma can be overcome by cotargeting MEK and IGF-1R/PI3K. Cancer Cell 18(6): 683-95.

Wang et al., (2010) RNAi screening implicates a SKN-1-dependent transcriptional response in stress resistance and longevity deriving from translation inhibition. PLoS Genet 6(8). 17 pages.

Willcox et al., (2008) FOXO3A genotype is strongly associated with human longevity. Proc Natl Acad Sci U S A 105(37): 13987-92.

Yaish et al., (1988) Blocking of EGF-dependent cell proliferation by EGF receptor kinase inhibitors. Science 242(4880): 933-5.

Yamada et al., (1999) Cellular sensitization to cisplatin and carboplatin with decreased removal of platinum-DNA adduct by glucose-regulated stress. Cancer Chemother Pharmacol 44(1): 59-64.

Yoneda et al., (1991) The antiproliferative effects of tyrosine kinase inhibitors tyrphostins on a human squamous cell carcinoma in vitro and in nude mice. Cancer Res 51(16): 4430-5.

Yuan and Parrill (2000) QSAR development to describe HIV-1 integrase inhibition. Journal of Molecular Structure: Theochem 529(1-3): 273-282.

Zhang et al., (2011) TDP-43 neurotoxicity and protein aggregation modulated by heat shock factor and insulin/IGF-1 signaling. Hum Mol Genet 20(10): 1952-65.

* cited by examiner

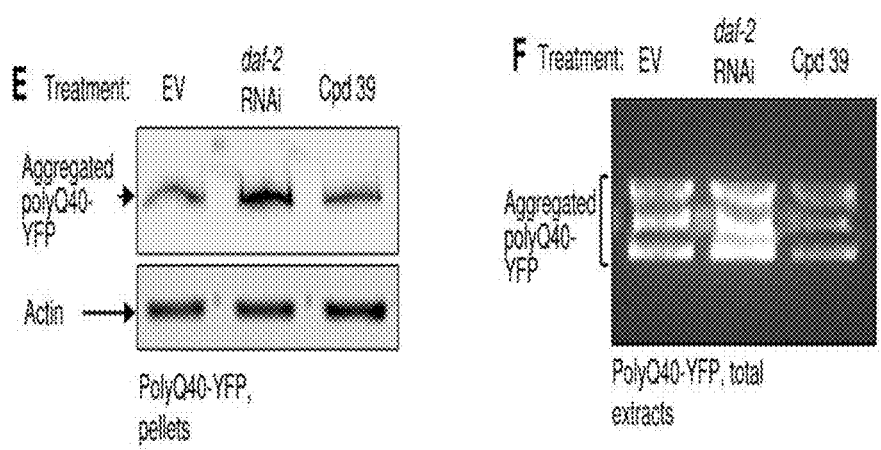
Figure 7 (ii)

IGF-1R SIGNALING PATHWAY INHIBITORS USEFUL IN THE TREATMENT OF NEURODEGENERATIVE DISEASES

CROSS REFERENCE TO RELATED APPLICATIONS

This application is a 35 U.S.C. §371 National Phase Entry Application from PCT/IB2014/063071, filed on Jul. 13, 2014, and designating the United States, which claims the benefit from of U.S. Provisional Patent Application No. 61/846,014 filed 14 Jul. 2013, which is hereby incorporated herein in its entirety by reference.

FIELD OF THE INVENTION

The present invention related to IGF-1 receptor signaling pathway inhibitor compounds useful in the prevention and treatment of neurodegenerative diseases and disorders. The invention provides pharmaceutical compositions including such compounds, and methods of using these compounds and compositions in the treatment of neurodegenerative diseases, in particular neurodegenerative diseases associated with toxic protein aggregation, especially Alzheimer's disease.

BACKGROUND OF THE INVENTION

Aberrant protein aggregation is mechanistically linked to the emergence of late-onset human neurodegenerative disorders such as Alzheimer's (AD), Parkinson's (PD) and Huntington's (HD) diseases (Selkoe, 2003, Nature 426 (6968):900-4). Although the nature of the aggregating proteins and the mechanisms that underlie the development of these maladies differ greatly, they share surprisingly similar temporal patterns of emergence. Typically, familial, mutation-linked cases emerge during the fifth decade of life while sporadic cases do not onset earlier the seventh decade (Amaducci and Tesco, 1994, Curr. Opin. Neurol. 7(4):283-6). Hitherto it is largely unknown why these disorders onset late in life and why distinct maladies exhibit similar temporal emergence patterns, however recent studies indicate that the aging process plays major roles in enabling the aggregation of neurodegeneration-linked proteins, to onset late in life (Cohen et al., 2006, Science 313(5793):1604-10).

Perhaps the most prominent aging and lifespan regulating pathway is the Insulin/IGF signaling pathway (IIS). IIS reduction elevates stress resistance and extends lifespans of worms, flies (Kenyon, 2005, Cell 120(4):449-60) and mice (Holzenberger et al., 2003, Nature 421(6919):182-7). In the nematode Caenorhabditis elegans (C. elegans), the sole Insulin/IGF receptor DAF-2, initiates a signaling cascade that mediates the phosphorylation of its downstream transcription factor DAF-16. Phosphorylated DAF-16 is prevented from entering the nucleus and from regulating its target genes. Thus, IIS reduction hyper-activates DAF-16 and creates long-lived, stress resistant worms (Kenyon, 2005, Cell 120(4):449-60). Similarly, reduced IGF signaling mediates longevity and stress resistance of mice (Holzenberger et al., 2003, Nature 421(6919):182-7; Taguchi et al. 2007, Science 317(5836):369-72).

The IGF signaling pathway was shown to attenuate in human centenarians of different ethnicities (Suh et al. 2008, Proc. Natl. Acad. Sci 105(9):3438-42; Flachsbart et al. 2009, Proc. Natl. Acad. Sci 106(8):2700-5), suggesting that this longevity mechanism is conserved from worms to humans.

IIS reduction was further found to protect worms from the toxic effects that stem from the expression and aggregation of the human Alzheimer's disease associated peptide, $A\beta 1$-42 in their body wall muscles ($A\beta$ worms) (Cohen et al., 2006, Science, 313(5793):1604-10). It is apparent that the cellular ability to maintain proper protein homeostasis is critical to enable longevity (Cohen and Dillin, 2008, Nature Rev. Neuroscience 9: 759-67). Analogously to worms, long-lived mice that harbor only one copy of the IGF1 receptor (IGF1 receptor is a mammalian DAF-2 orthologue) are protected from behavioral and pathological impairments associated with the aggregation and deposition of human $A\beta$ in the brain. This protection was suggested to be conferred by the formation of densely packed $A\beta$ of low toxicity in the brain (Cohen et al. 2009, Cell 139(6):1157-69). It was further shown that late life IIS reduction efficiently protects from Ab toxicity of transgenic nematodes that express human $A\beta$ without affecting development, reproduction or lifespan (Cohen et al. 2010, Aging Cell 9:126-34). These data indicate that the protection from $A\beta$ proteotoxicity provided by reduced IIS is conserved from worms to mice.

Recent studies indicate that this approach of IIS reduction can protect worm models from toxicity of various neurodegeneration-linked, aggregative proteins including ataxin-3 (Teixeira-Castro et al, Hum Mol Genet. 20(15): 2996-3009) and TDP-43 (Zhang et al, Hum Mol Genet. 15; 20(10):1952-65). WO 2010/075511, to some of the inventors of the present invention, disclosed a study in which genetically engineered Alzheimer's model of mice with reduced IGF-1 signaling were found to be protected from Alzheimer's like disease symptoms, including reduced behavioral impairment, mitigated neuroinflammation, and slower rate of neuronal loss. This protection was correlated with the hyper-aggregation of $A\beta$ leading to tightly packed, ordered plaques, suggesting that one aspect of the protection conferred by reduced IGF signaling is the sequestration of highly toxic soluble $A\beta$ oligomers into dense aggregates of lower toxicity. Based on these results, it was suggested that agents that reduce IGF-1 signaling may be useful for the treatment of neurodegenerative diseases, yet not a single candidate was identified.

IIS reduction was previously suggested for the treatment of various cell proliferative disorders. Enhanced activities of protein tyrosine kinases resulting from overexpression of the normal kinase, upregulation of ligands of receptor tyrosine kinases or activating mutations, are a hallmark of many diseases which involve cellular proliferation, including cancer. Examples of specific receptor tyrosine kinases associated with cell proliferative disorders include platelet derived growth factor receptor (PDGFR), insulin-like growth factor 1 receptor (IGF-1R), epidermal growth factor receptor (EDFR), and the related HER2.

WO 2008/068751 and WO 2009/147682 to some of the inventors of the present invention discloses the use of tyrphostin derivatives acting as protein kinase (PK) and receptor kinase (RK) signaling modulators for the treatment of diseases associated with altered or abnormal activity or signaling of protein kinases, such as cell proliferative disorders, in particular cancer, diabetic nephropathy, a metabolic disorder, a fibrotic disorder or psoriasis.

There have been several drugs developed for the treatment of Alzheimer's disease, including several anticholinergic agents, which are currently marketed. However, there remains a continuing need for the development of additional therapeutic strategies for the treatment of Alzheimer's disease as well as other neurodegenerative diseases.

SUMMARY OF THE INVENTION

The present invention relates to use of compounds which show increased inhibitory properties of insulin-like growth factor 1 receptor (IGF-1R) for the inhibition, treatment or prevention of neurodegenerative diseases by reducing the signaling activity of the pathway initiated by the insulin-like growth factor 1. In particular these compounds and compositions are useful in the treatment of neurodegenerative diseases associated with toxic protein aggregation. Without wishing to be bound by theory or mechanism of action it is assumed that IGF-1R signaling reduction either early or late in life, can protect from age onset proteotoxicity by invoking a mechanism that converts toxic aggregates into larger, less toxic high molecular weight aggregates.

The present invention is based in part on the unexpected discovery that inhibition of the Insulin/IGF signaling cascade (IIS) leads to elevation the expression of protective IIS target genes, promotes stress resistance and protects nematodes from AD- and HD-associated proteotoxicity without affecting lifespan. Thus, the potent IIS inhibitors described herein (e.g., compound 39), are promising compounds for the treatment of neurodegenerative disorders through a selective manipulation of aging.

According to one aspect, the present invention provides a method for the prevention or treatment of a neurodegenerative disease, wherein the method comprises the step of administering to a subject in need thereof a therapeutically effective amount of a compound represented by the structure of formula I:

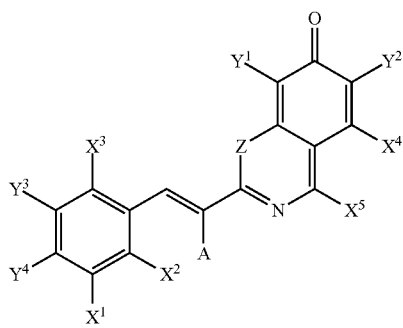

wherein
A is H or CN;
Z is S, SO or $SO_2$;
$X^1$, $X^2$, $X^3$, $X^4$, $X^5$, $Y^1$ and $Y^2$ are each independently selected from H, halogen, alkyl, haloalkyl and $OR^1$; and
$Y^3$ and $Y^4$ are each $OR^1$, wherein each $R^1$ is independently H, $C_1$-$C_4$ alkyl, acyl, —$(CH_2CH_2O)_n$ wherein n is an integer of 1 to 20, or a functional group that gives rise to hydroxyl upon hydrolysis, including salts, hydrates, solvates, polymorphs, optical isomers, geometrical isomers, enantiomers, diastereomers, and mixtures thereof.

According to another aspect, the present invention provides a method for the prevention or treatment of a neurodegenerative disease, wherein the method comprises the step of administering to a subject in need thereof a therapeutically effective amount of a compound represented by the structure of formula II:

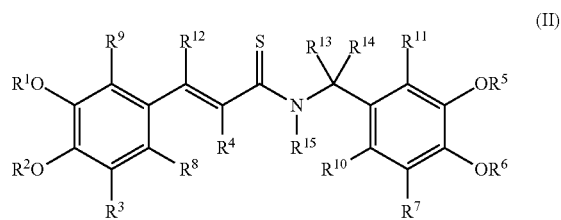

wherein
$R^1$, $R^2$, $R^5$ and $R^6$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $(CH_2CH_2O)_nH$, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, haloalkyl, acyl and a functional group that gives rise to hydroxyl upon hydrolysis;
$R^3$, $R^4$, $R^7$, $R^8$, $R^9$, $R^{10}$, $R^{11}$, $R^{12}$, $R^{13}$ and $R^{14}$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, halogen, haloalkyl, $NO_2$, CN, $N_3$, $SO_2R^a$, $COOR^a$, $CSNR^aR^b$, $CSOR^a$, $OR^a$, $CONR^aR^b$, $NR^aR^b$, $SR^a$, and $CH_2SR^a$, wherein $R^a$ and $R^b$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, haloalkyl, $(CH_2CH_2O)_nH$, acyl or a functional group that gives rise to hydroxyl upon hydrolysis; and
$R^{15}$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, haloalkyl, or $OR^b$ wherein $R^b$ is independently H or $C_1$-$C_4$ alkyl; including salts, hydrates, solvates, polymorphs, optical isomers, geometrical isomers, enantiomers, diastereomers, and mixtures thereof.

According to some embodiments, the present invention provides a method for the prevention or treatment of a neurodegenerative disease, wherein the method comprises the step of administering to a subject in need thereof a therapeutically effective amount of a compound represented by the structure of formula III:

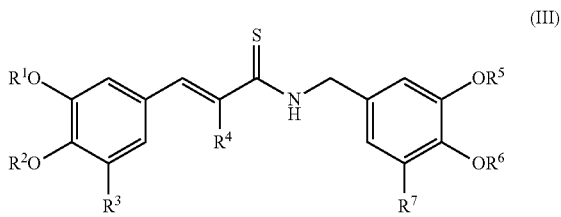

wherein
$R^1$, $R^2$, $R^5$ and $R^6$ are independently selected from H, $C_1$-$C_4$ alkyl, $(CH_2CH_2O)_n$, wherein n is an integer of 1 to 20, acyl and a functional group that gives rise to hydroxyl upon hydrolysis;

R$^3$ and R$^7$ are independently selected from H, halogen, C$_1$-C$_4$ alkyl, haloalkyl and OR$^{16}$ wherein R$^{16}$ is H, C$_1$-C$_4$ alkyl, (CH$_2$CH$_2$O)$_n$, acyl or a functional group that gives rise to hydroxyl upon hydrolysis; and R$^4$ is H or CN.

According to some embodiments, the present invention provides a method for the prevention or treatment of a neurodegenerative disease, wherein the method comprises the step of administering to a subject in need thereof a therapeutically effective amount of a compound represented by the structure of formula IV:

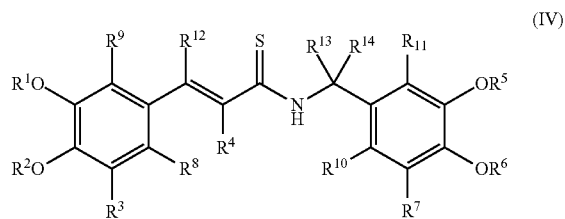

(IV)

wherein
R$^1$, R$^2$, R$^5$ and R$^6$ are independently selected from H, C$_1$-C$_4$ alkyl, (CH$_2$CH$_2$O)$_n$, wherein n is an integer of 1 to 20, acyl and a functional group that gives rise to hydroxyl upon hydrolysis;
R$^3$, R$^7$, R$^8$, R$^9$, R$^{10}$, R$^{11}$, R$^{12}$, R$^{13}$ and R$^{14}$ are independently selected from H, halogen, C$_1$-C$_4$ alkyl, haloalkyl and OR$^{16}$ wherein R$^{16}$ is H, C$_1$-C$_4$ alkyl, (CH$_2$CH$_2$O)$_n$, acyl or a functional group that gives rise to hydroxyl upon hydrolysis; and
R$^4$ is H or CN.

According to some embodiments, the neurodegenerative disease to be treated by methods of the invention is a neurodegenerative disease caused by toxic protein aggregation. According to some other embodiments, the toxic protein aggregation is selected from Amyloidosis, Prion disorders, Motor Neuron disease, Alzheimer's disease, Frontotemporal dementia 17 (FTD17), Huntington's disease (HD) and Parkinson's disease. Non limiting examples of Amyloidosis diseases include AL amyloidosis, AA amyloidosis, familial amyloid polyneuropathies, senile systemic amyloidosis, Leptomeningeal amyloidosis, Haemodialysis-associated amyloidosis, Finnish type amyloidosis, Cerebral amyloid angiopathy; Familial visceral amyloidosis; Familial corneal amyloidosis; Primary cutaneous amyloidosis and Senile amyloid of atria of heart. Non limiting examples of prion disorders include Finnish type amyloidosis; creutzfeldt-Jakob disease, kuru, fatal familiar insomnia and Gerstmann-Straussler-Scheinker disease.

According to some embodiments, the neurodegenerative disease is caused by toxic amyloid beta (Aβ) aggregation. According to some currently preferred embodiments, the neurodegenerative disease is Alzheimer's disease.

In other embodiments, the present invention provides a method for the prevention or treatment of a neurodegenerative disease, wherein the method comprises administering to a subject in need thereof a therapeutically effective amount of a compound represented by the structure of formula I, wherein A is CN, Z is S, Y$^3$ and Y$^4$ are each OH, and X$^1$ is a halogen selected from Br and I. Each possibility represents a separate embodiment of the present invention. In yet other embodiments, the present invention provides a method for the prevention or treatment of a neurodegenerative disease, wherein the method comprises administering to a subject in need thereof a therapeutically effective amount of a compound represented by the structure of formula I, wherein A is H, Z is S, Y$^3$ and Y$^4$ are each OH, and X$^3$ is a halogen selected from Br and I. Each possibility represents a separate embodiment of the present invention. In further embodiments, the present invention provides a method for the prevention or treatment of a neurodegenerative disease, wherein the method comprises administering to a subject in need thereof a therapeutically effective amount of a compound represented by the structure of formula I, wherein A is H, Z is S, Y$^3$ and Y$^4$ are each OH, and X$^2$ is a halogen selected from Br and I. Each possibility represents a separate embodiment of the present invention. In additional embodiments, the present invention provides a method for the prevention or treatment of a neurodegenerative disease, wherein the method comprises administering to a subject in need thereof a therapeutically effective amount of a compound represented by the structure of formula I, wherein A is H, Z is S, Y$^3$ and Y$^4$ are each OH, and X$^1$ and X$^4$ are each a halogen selected from Br and I. In yet other embodiments, the present invention provides a method for the prevention or treatment of a neurodegenerative disease, wherein the method comprises administering to a subject in need thereof a therapeutically effective amount of a compound represented by the structure of formula I, wherein A is H, Z is SO$_2$, Y$^3$ and Y$^4$ are each OH, and X$^1$ is a halogen selected from Br and I. In yet other embodiments, the present invention provides a method for the prevention or treatment of a neurodegenerative disease, wherein the method comprises administering to a subject in need thereof a therapeutically effective amount of a compound represented by the structure of formula I, wherein A is H, Z is SO$_2$, Y$^3$ and Y$^4$ are each OH, and at least one of X$^1$, X$^2$, X$^3$, X$^4$, Y$^1$ and Y$^2$ is a halogen. Each possibility represents a separate embodiment of the present invention.

According to some embodiments, the present invention provides a method for the prevention or treatment of a neurodegenerative disease, wherein the method comprises the step of administering to a subject in need thereof a therapeutically effective amount of a compound represented by the structure of formula II, wherein R$^1$, R$^2$, R$^5$ and R$^6$ are each H or a functional group that gives rise to hydroxyl upon hydrolysis. In another embodiment, the present invention provides a method for the prevention or treatment of a neurodegenerative disease, wherein the method comprises administering to a subject in need thereof a therapeutically effective amount of a compound represented by the structure of formula II wherein R$^7$ is OR$^a$ and R$^1$, R$^2$, R$^5$, R$^6$, and R$^a$ are each H or a functional group that gives rise to hydroxyl upon hydrolysis. In yet another embodiment, the present invention provides a method for the prevention or treatment of a neurodegenerative disease, wherein the method comprises administering to a subject in need thereof a therapeutically effective amount of a compound represented by the structure of formula II wherein R$^{13}$ and R$^{14}$ are each independently H, C$_1$-C$_4$ alkyl, C$_2$-C$_6$ alkenyl, C$_2$-C$_6$ alkynyl, C$_1$-C$_4$ alkyl-C$_2$-C$_6$ alkenyl or C$_1$-C$_4$ alkyl-C$_2$-C$_6$ alkynyl. In still another embodiment, one of R$^{13}$ and R$^{14}$ is H or C$_1$-C$_4$ alkyl. Each possibility represents a separate embodiment of the invention.

In particular embodiments, the present invention provides a method for the prevention or treatment of a neurodegenerative disease, wherein the method comprises administering to a subject in need thereof a therapeutically effective amount of a compound represented by the structure of formula II, wherein R$^4$, R$^{11}$, R$^{12}$, R$^{13}$, R$^{14}$ and R$^{15}$ are each H. In additional embodiments, substituents $R^{13}$, $R^{14}$ and $R^{15}$ are each H. Each possibility represents a separate embodiment of the invention.

In some embodiments, the present invention provides a method for the prevention or treatment of a neurodegenerative disease, wherein the method comprises administering to a subject in need thereof a therapeutically effective amount of a compound represented by the structure of formula II wherein $R^3$, $R^4$, $R^7$, $R^8$, $R^9$, $R^{10}$, $R^{11}$, $R^{12}$, $R^{13}$ and $R^{14}$ are each H, halogen, haloalkyl, OH, $NO_2$, CN, or $CH_2SR^a$, wherein $R^a$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

According to some additional embodiments, the present invention provides a method for the prevention or treatment of a neurodegenerative disease, wherein the method comprises administering to a subject in need thereof a therapeutically effective amount of a compound represented by the structure of formula II wherein $R^3$, $R^7$, $R^8$, $R^9$, $R^{10}$ and $R^{11}$ are each independently H, halogen, haloalkyl, $CH_2SR^a$ or OH; $R^4$, $R^{12}$, $R^{13}$, and $R^{14}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, aryl, halogen, haloalkyl, $NO_2$, or CN; and $R^{15}$ is H, wherein $R^a$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

In certain embodiments, the present invention provides a method for the prevention or treatment of a neurodegenerative disease, wherein the method comprises the step of administering to a subject in need thereof a therapeutically effective amount of a compound represented by the structure of formula II wherein $R^3$, $R^7$, $R^8$, $R^9$, $R^{10}$ and $R^{11}$ are each independently H, halogen, haloalkyl, OH or $CH_2SR^a$; and $R^4$, $R^{12}$, $R^{13}$ and $R^{14}$ and $R^{15}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, aryl, halogen, haloalkyl, $NO_2$ or CN, wherein $R^a$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

In some embodiments, the substituents $R^4$, $R^{11}$, $R^{12}$, $R^{13}$, $R^{14}$ and $R^{15}$ in the compound represented by formula II are each H or $C_1$-$C_4$ alkyl. In specific embodiments, $R^1$, $R^2$, $R^5$ and $R^6$ in the compound represented by formula II are each H or a functional group that gives rise to hydroxyl upon hydrolysis; $R^3$, $R^8$, and $R^9$ in the compound represented by formula II are each independently H, halogen, haloalkyl, or $CH_2SR^a$; $R^7$, $R^{10}$ and $R^{11}$ in the compound represented by formula II are each independently H, halogen, haloalkyl, OH or a functional group that gives rise to hydroxyl upon hydrolysis; and $R^4$, $R^{12}$, $R^{13}$, $R^{14}$ and $R^{15}$ in the compound represented by formula II are each H, or $C_1$-$C_4$ alkyl, wherein $R^a$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

In particular non-liming embodiments, the substituents $R^1$, $R^2$, $R^4$, $R^5$, $R^6$, $R^1$, $R^{12}$, $R^{13}$, $R^{14}$ and $R^{15}$ in the compound represented by formula II are each H; $R^7$ in the compound represented by formula II is OH; and at least one of $R^3$, $R^8$, $R^9$ and $R^1$ in the compound represented by formula II is halogen. In additional embodiments, $R^1$, $R^2$, $R^4$, $R^5$, $R^6$, $R^8$, $R^{10}$, $R^{12}$, $R^{13}$, $R^{14}$ and $R^{15}$ in the compound represented by formula II are each H; $R^7$ is OH; and at least one of $R^3$, $R^9$ and $R^{11}$ in the compound represented by formula II is halogen. Each possibility represents a separate embodiment of the invention.

In some embodiments, the present invention provides a method for the prevention or treatment of a neurodegenerative disease, wherein the method comprises the step of administering to a subject in need thereof a therapeutically effective amount of a compound represented by the structure of formula III, wherein $R^4$ is CN.

In other embodiments, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each hydrogen.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each $CH_3$.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^3$ and $R^7$ are each a hydrogen, halogen, halomethyl, OH or $OCH_3$.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each H, $R^3$ is halogen and $R^7$ is OH.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each H, and $R^3$ and $R^7$ are each halogen.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each H, $R^3$ is halomethyl and $R^7$ is OH.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each H, $R^3$ is halogen and $R^7$ is H.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each H, $R^3$ is OH and $R^7$ is halogen.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each $CH_3$, $R^3$ is halogen and $R^7$ is $OCH_3$.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each $CH_3$, and $R^3$ and $R^7$ are each halogen.

In another embodiment, the present invention provides a method for the prevention or treatment of a neurodegenerative disease, wherein the method comprises the step of administering to a subject in need thereof a therapeutically effective amount of a compound represented by the structure of formula III wherein $R^4$ is hydrogen.

In another embodiment, the present invention provides a method for the prevention or treatment of a neurodegenerative disease, wherein the method comprises the step of administering to a subject in need thereof a therapeutically effective amount of a compound represented by the structure of formula III wherein $R^1$, $R^2$, $R^5$ and $R^6$ are each hydrogen.

In another embodiment, the present invention provides a method for the prevention or treatment of a neurodegenerative disease, wherein the method comprises the step of administering to a subject in need thereof a therapeutically effective amount of a compound represented by the structure of formula III wherein $R^1$, $R^2$, $R^5$ and $R^6$ are each $CH_3$.

In another embodiment, the present invention provides a method for the prevention or treatment of a neurodegenerative disease, wherein the method comprises the step of administering to a subject in need thereof a therapeutically effective amount of a compound represented by the structure of formula III wherein $R^3$ and $R^7$ are each hydrogen, halogen, halomethyl, OH or $OCH_3$.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each H, $R^3$ is halogen and $R^7$ is OH.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each H, and $R^3$ and $R^7$ are each halogen.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each H, $R^3$ is halomethyl and $R^7$ is OH.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each H, $R^3$ is halogen and $R^7$ is H.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each H, $R^3$ is OH and $R^7$ is halogen.

In another embodiment, the present invention provides a method for the prevention or treatment of a neurodegenerative disease, wherein the method comprises the step of administering to a subject in need thereof a therapeutically effective amount of a compound represented by the structure of formula III wherein $R^3$ is halogen and $R^7$ is $OCH_3$.

In another embodiment, the present invention provides a method for the prevention or treatment of a neurodegenerative disease, wherein the method comprises the step of administering to a subject in need thereof a therapeutically effective amount of a compound represented by the structure of formula III, wherein $R^1$, $R^2$, $R^5$ and $R^6$ are each $CH_3$, and $R^3$ and $R^7$ are each halogen.

According to some embodiments, the present invention provides a method for the prevention or treatment of a neurodegenerative disease, wherein the method comprises the step of administering to a subject in need thereof a therapeutically effective amount of a compound selected from the group consisting of compounds represented by structures nos. 1-39

It is to be emphasized that compounds represented by structures nos. 1-39 encompasses all structural and geometrical isomers of such compounds, including cis, trans, E and Z isomers and optical isomers, independently at each occurrence.

According to some currently preferred embodiments, the present invention provides method for the treatment of a neurodegenerative disease, wherein the method comprises the step of administering to a subject in need thereof a therapeutically effective amount of compound no. 39. According to some additional preferred embodiments, the present invention provides method for the treatment of a neurodegenerative disease, wherein the method comprises the step of administering to a subject in need thereof a therapeutically effective amount of compound no. 29. According to other preferred embodiments, the present invention provides method for the treatment of a neurodegenerative disease, wherein the method comprises the step of administering to a subject in need thereof a therapeutically effective amount of compound no. 4. According to further preferred embodiments, the present invention provides method for the treatment of a Alzheimer's disease, wherein the method comprises administering to a subject in need thereof a therapeutically effective amount of compound no. 39. According to further preferred embodiments, the present invention provides method for the treatment of a Alzheimer's disease, wherein the method comprises administering to a subject in need thereof a therapeutically effective amount of compound no. 29. According to yet other preferred embodiments, the present invention provides method for the treatment of a Alzheimer's disease, wherein the method comprises administering to a subject in need thereof a therapeutically effective amount of compound no. 4. The above compounds may be isolated from any medium containing them. Accordingly, in some embodiments, the present invention provides method for the treatment of a neurodegenerative disease, wherein the method comprises administering to a subject in need thereof a therapeutically effective amount of isolated compounds represented by the general structure of formulae I-IV, or any compounds encompassed by this generic structure including, but not limited to, compounds 1-39. Each of these methods represents a separate embodiment of the present invention.

In one embodiment, the neurodegenerative disease or disorder is related to the activity of the insulin-like growth factor-1 receptor (IGF-1R).

Without being bound to any particular theory or mechanism of action, it is contemplated that the compounds of the present invention are inhibitors of the IGF-1 signaling pathway. It has now been surprisingly found that these compounds protect worms from symptoms that stem from toxic aggregation of the Aβ peptide that leads to Alzheimer's like disease, including reduced motility. This protection was further correlated with the hyperaggregation of Aβ leading to tightly packed, ordered plaques, suggesting that one aspect of the protection conferred by reduced IGF signaling is the sequestration of soluble Aβ oligomers into dense aggregates of lower toxicity.

In some embodiments, the compounds represented by formulae I-IV are inhibitors of an insulin receptor or an insulin-like growth factor-1 receptor (IGF-1R) signaling, and/or the compounds of formulae I-IV interact with, affect or inhibit a substrate protein in the IGF-1R mediated pathway. In some embodiments, the substrate protein is Insulin Receptor Substrate 1 (IRS1), Insulin Receptor Substrate 2 (IRS2), or a combination thereof. In one particular embodiment, the compounds of formulae I-IV are IGF-1R kinase inhibitors that lead to at least one of the dissociation of IRS1 or IRS2 from the cell membrane, phosphorylation of IRS1 or IRS2, and/or degradation of IRS1 or IRS2, in any order.

The terms "interacts with, affects or inhibits" includes, without limitation, post-translational modifications, phosphorylation, translocation, and degradation, where such effects may be direct, i.e., by direct interaction of the compound of formulae I-IV, or indirectly. e.g., through another protein or proteins.

Within the scope of the present invention are pharmaceutical compositions comprising at least one compound represented by the structure of formulae I-IV or at least one of compounds 1-39 for inhibiting, treating or preventing a neurodegenerative disease in a subject. In various embodiments, the pharmaceutical compositions of the present invention are useful in inhibiting, treating or preventing an insulin-like growth factor 1 receptor (IGF-1R) and/or insulin receptor substrate 1 (IRS1) and/or insulin receptor substrate 2 (IRS2) signaling related disorder. In certain embodiments, the present invention provides a compound represented by the structure of formulae I-IV or any of compounds 1-39 for use in inhibiting, treating or preventing a neurodegenerative disease in a subject. Each possibility represents a separate embodiment of the present invention. In other specific embodiments, the present invention provides a compound represented by the structure of formulae I-IV or any of compounds 1-39 for use in inhibiting, treating or preventing Alzheimer's disease in a subject. Each possibility represents a separate embodiment of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

D-F. Relative expression levels of DAF-16 (D), HSF-1 (E) and SKN-1 (F) target genes in untreated (black bars), COMPOUND 39-treated (dashed bars) and daf-2 RNAi-treated CF512 worms as measured by real-time quantitative PCR. Bars represent average values of three independent experiments±SEM.

Figure 6:
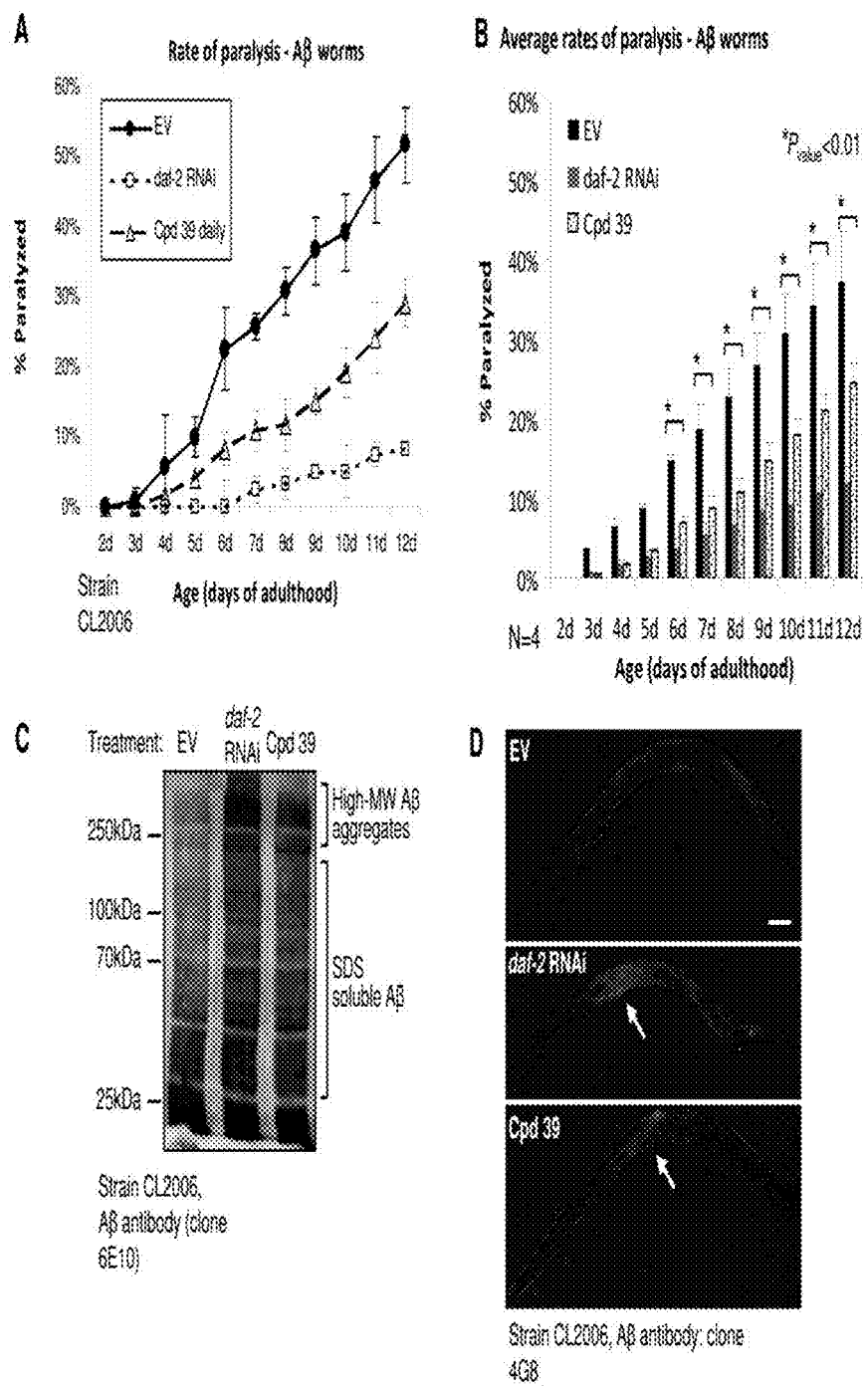

FIG. 6: Protection from Aβ-mediated proteotoxicity by compound no. 39. A. EV bacteria grown CL2006 worms were treated with either 600 μM compound no. 39 or the vehicle on days 1 and 2 of adulthood and placed on plates which were supplemented daily with compound no. 39 or the vehicle. Rates of paralysis were scored daily from day 3 to day 12 of adulthood. Compound no. 39 significantly reduced the rate of paralysis within the worm population (triangles) compared to the control group (black circles). daf-2 RNAi (open squares) provides more efficient protection compared to compound no. 39. B. Four independent repeats of the experiment described in A. C. Similarly to daf-2 RNAi, compound no. 39 treatment resulted in Aβ hyper-aggregation as revealed by WB analysis of high-speed supernatants of untreated CL2006 worms and their counterparts that were treated with either daf-2 RNAi or compound no. 39. D. Immune-fluorescence visualization indicates that IIS reduction by either compound no. 39 or daf-2 RNAi leads to the accumulation of Aβ in the center of the worm body.

Figure 7:
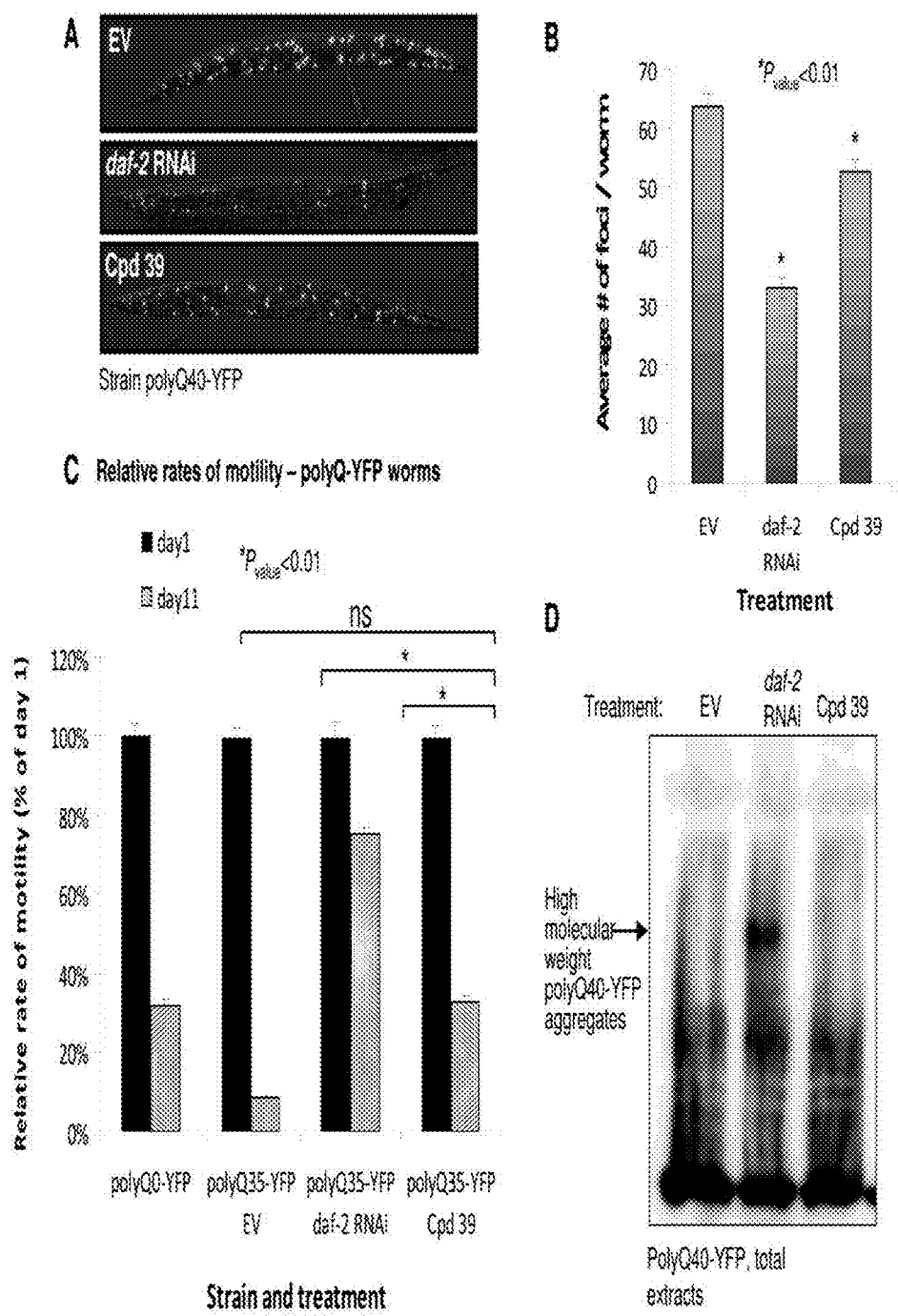

FIG. 7: Compound no. 39 alleviates polyQ-associated toxicity. A-B. compound no. 39-treated polyQ40-YFP worms contain significantly fewer polyQ40-YFP foci compared to their counterparts that were treated with the chemical vehicle as visualized (A) and quantified (B) by fluorescent microscopy (average numbers of foci/worm in EV and in compound no. 39-treated animals were 63.66 and 52.78 respectively, $P_{value}$=0.00026). The effect of compound no. 39 was less prominent than that of daf-2 RNAi (average of 32.94 foci/worm). C. compound no. 39 treatment rescues polyQ35-YFP worms from late-life motility impairment. While the average crawling speed of 11 days old, untreated polyQ35-YFP worms was 8.8% of the average speed at day 1 of adulthood, the speed of compound no. 39-treated animals was 32.9% of the speed at day 1 ($P_{value}$=1.21E-29). The average crawling speed of compound no. 39-treated animals was similar to that of day 11 worms that do not express polyQ stretches (polyQ0-YFP, average speed of 31.8% at day 11 compared to day 1 of adulthood). The relative speed of day 11 old daf-2 RNAi-treated animals was 75.4% compared to the speed measured at day 1. D-F. compound no. 39 treatment does not enhance the aggregation rate of polyQ40-YFP as examined by WB of whole worm extracts (D), high-speed pellets of worm debris (E) and by YFP fluorescence assay of worm homogenates separated on native gel (F).

Figure 8:
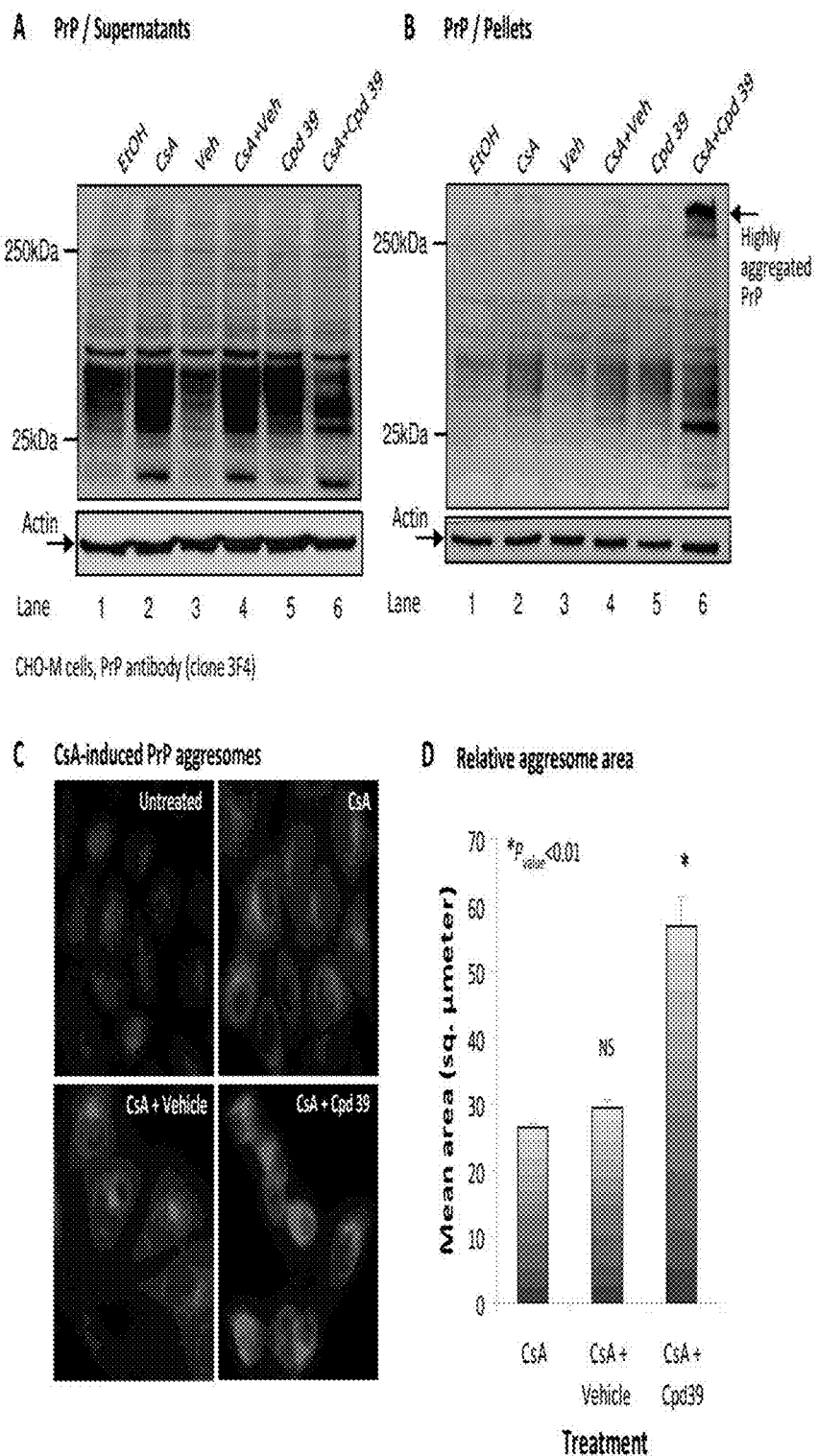

FIG. 8: Enhanced PrP aggregation and deposition in cells treated with both CsA and Compound no. 39. A-B. CHO-M cells were treated with 60 μg/ml cyclosporine-A (CsA), 3 μM Compound no. 39, or both, lysed and subjected to high-speed centrifugation. PrP was blotted in supernatants (A) and pellets (B). Combined treatment with CsA and Compound no. 39 reduced the amounts of soluble and elevated the quantities of highly aggregated PrP. C. Immunofluorescence using PrP antibody indicated that PrP-containing aggresomes of cells that were treated with both drugs CsA and Compound no. 39 occupy larger areas than PrP aggresomes of cells that were treated solely with CsA. D. Average areas of aggresomes of cells that were treated as in C.

Figure 9:
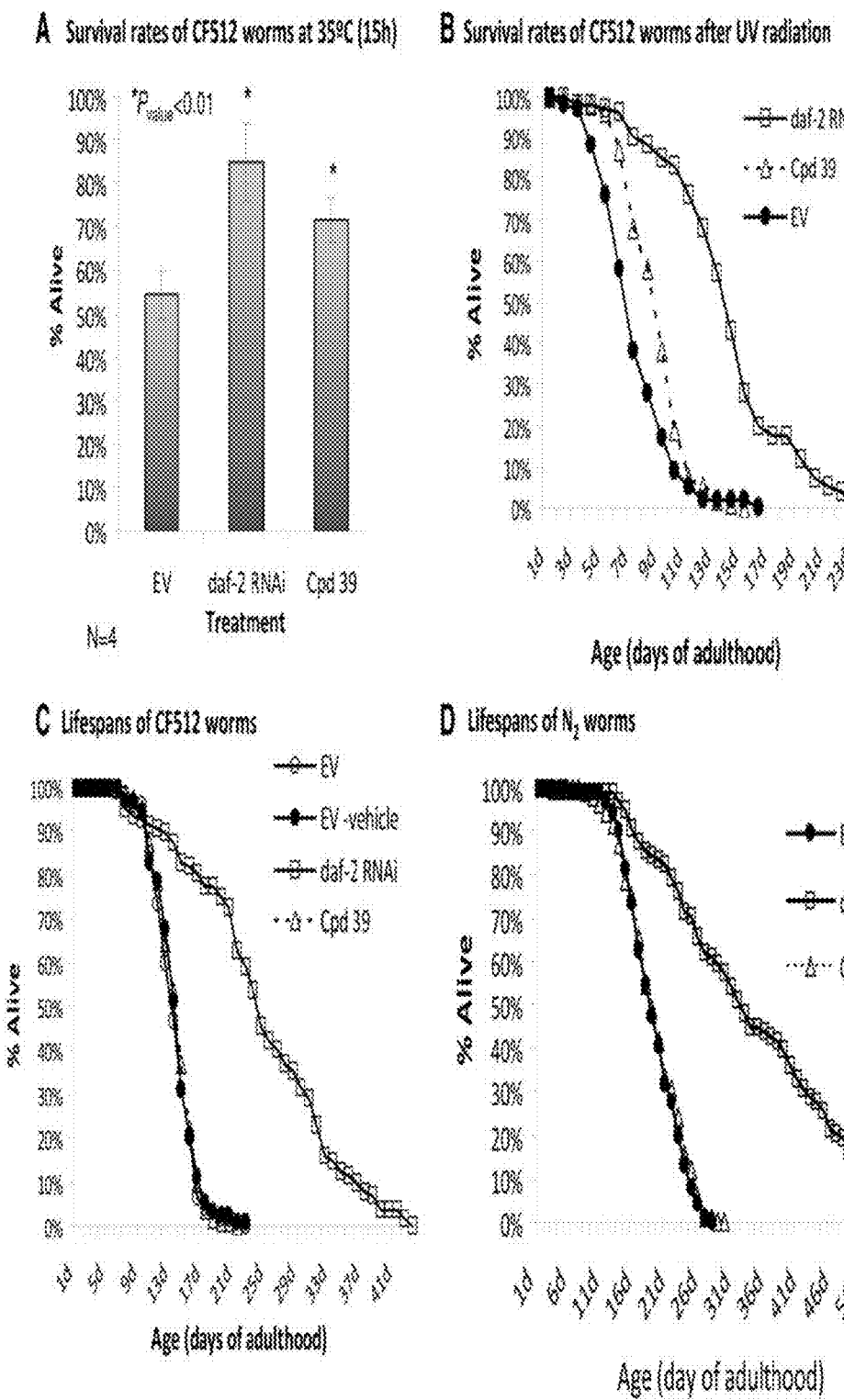

FIG. 9: Compound no. 39 elevates stress resistance but has no effect on lifespan. A. Compound no. 39-treated CF512 worms exhibit significantly elevated survival rate (71.7%) after 15 hours of exposure to 35° C. compared to their untreated counterparts (54.3%, $P_{value}$=0.008) but lower than daf-2 RNAi-treated animals (84.8%, $P_{value}$=0.0001). B. CF512 worms were treated as in A, exposed to sub-lethal UV dose and their survival rates were recorded daily. COMPOUND 39-treated animals lived longer than untreated worms (8.76±0.21 and 7.03±0.22 days respectively, $P_{value}$=2.36E-8) but less than their daf-2 RNAi-treated counterparts (13.89±0.41 days). C. Untreated worms (open circles), Compound no. 39-treated animals (triangles) and their counterparts that were supplemented with the chemical vehicle (black circles) exhibit indistinguishable lifespans. daf-2 RNAi-treated worms exhibited extended lifespan (squares). D. The lifespans of wild-type worms (strain $N_2$) were not affected by a daily Compound no. 39 treatment.

DETAILED DESCRIPTION OF THE INVENTION

The present invention relates to compounds which are potent inhibitors of and the IGF-1 signaling pathway. The compounds are useful in treating neurodegenerative diseases and conditions; in particular, toxic protein aggregation related neurodegenerative diseases, for example, wherein the toxicity is associated with ameloid beta (Aβ) expression.

Toxic protein aggregation (proteotoxicity) is a unifying feature in the development of late-onset human neurodegenerative disorders. Reduction of insulin/IGF-1 signaling (IIS), a prominent lifespan, developmental and reproductive regulatory pathway was previously shown to protect transgenic nematodes from proteotoxicity associated with the aggregation of the Alzheimer's disease-linked Aβ peptide (Cohen et al., 2006, Science 15; 313(5793):1604-10). It was also shown that reduced IGF-1R signaling results in a profound reduction in the toxicity associated with Aβ expression in the brain of mice (Cohen et al., 2009, Cell, 139:1157-69). The present invention is based in part on the unexpected discovery that specific IGF-1R kinase inhibitors previously shown to be useful in the treatment of a wide range of cancer cells type, were found to elevate stress resistance of worms and protect them from Aβ toxicity without affecting the worms' lifespan According to one aspect, the present invention provides a method for the prevention or treatment of a neurodegenerative disease, wherein the method comprises the step of administering to a subject in need thereof a therapeutically effective amount of a compound represented by the structure of formula I:

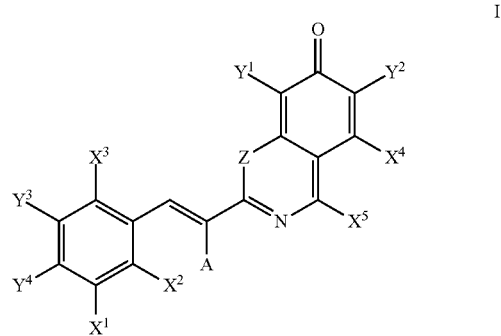

wherein

A is H or CN;

Z is S, SO or SO$_2$;

$X^1$, $X^2$, $X^3$, $X^4$, $X^5$, $Y^1$ and $Y^2$ are each independently selected from H, halogen, alkyl, haloalkyl and $OR^1$; and $Y^3$ and $Y^4$ are each $OR^1$, wherein each $R^1$ is independently H, $C_1$-$C_4$ alkyl, —(CH$_2$CH$_2$O)$_n$ wherein n is an integer of 1 to 20, acyl or a functional group that gives rise to hydroxyl upon hydrolysis, including salts, hydrates, solvates, polymorphs, optical isomers, geometrical isomers, enantiomers, diastereomers, and mixtures thereof.

In one embodiment, the present invention provides a method for the prevention or treatment of a neurodegenerative disease, wherein the method comprises administering to a subject in need thereof a therapeutically effective amount of a compound represented by the structure of formula I, wherein A is H. In another embodiment, the present invention provides a method for the prevention or treatment of a neurodegenerative disease, wherein the method comprises administering to a subject in need thereof a therapeutically effective amount of a compound represented by the structure of formula I, wherein A is CN. In some embodiments, the present invention provides a method for the prevention or treatment of a neurodegenerative disease, wherein the method comprises administering to a subject in need thereof a therapeutically effective amount of a compound represented by the structure of formula I, wherein Z is S. In other embodiments, the present invention provides a method for the prevention or treatment of a neurodegenerative disease, wherein the method comprises administering to a subject in need thereof a therapeutically effective amount of a compound represented by the structure of formula I, wherein Z is SO$_2$. In certain embodiments, the present invention provides a method for the prevention or treatment of a neurodegenerative disease, the method comprises administering to a subject in need thereof a therapeutically effective amount of a compound represented by the structure of formula I, wherein at least one of $X^1$, $X^2$, $X^3$, $X^4$, $Y^1$ and $Y^2$ is a halogen. In other embodiments, the present invention provides a method for the prevention or treatment of a neurodegenerative disease, wherein the method comprises administering to a subject in need thereof a therapeutically effective amount of a compound represented by the structure of formula I, wherein at least one of $X^1$, $X^2$, $X^3$, $X^4$, $Y^1$ and $Y^2$ is Br. In some embodiments, the present invention provides a method for the prevention or treatment of a neurodegenerative disease, wherein the method comprises administering to a subject in need thereof a therapeutically effective amount of a compound represented by the structure of formula I, wherein at least one of $X^1$, $X^2$, $X^3$, $X^4$, $Y^1$ and $Y^2$ is I. In certain embodiments, the present invention provides a method for the prevention or treatment of a neurodegenerative disease, wherein the method comprises administering to a subject in need thereof a therapeutically effective amount of a compound represented by the structure of formula I, wherein $X^1$, $X^2$, $X^3$, and $X^4$ are each selected from H or a halogen, wherein the halogen is preferably Br or I. In certain embodiments, the present invention provides a method for the prevention or treatment of a neurodegenerative disease, wherein the method comprises administering to a subject in need thereof a therapeutically effective amount of a compound represented by the structure of formula I, wherein $X^2$ is H. In certain embodiments, the present invention provides a method for the prevention or treatment of a neurodegenerative disease, wherein the method comprises administering to a subject in need thereof a therapeutically effective amount of a compound represented by the structure of formula I, wherein $X^5$ is H. In certain embodiments, the present invention provides a method for the prevention or treatment of a neurodegenerative disease, wherein the method comprises administering to a subject in need thereof a therapeutically effective amount of a compound represented by the structure of formula I, wherein $X^5$ is alkyl, preferably methyl. In some embodiments, the present invention provides a method for the prevention or treatment of a neurodegenerative disease, wherein the method comprises administering to a subject in need thereof a therapeutically effective amount of a compound represented by the structure of formula I, wherein $Y^3$ and $Y^4$ are each OH. In other embodiments, the present invention provides a method for the prevention or treatment of a neurodegenerative disease, wherein the method comprises administering to a subject in need thereof a therapeutically effective amount of a compound represented by the structure of formula I, wherein $Y^1$ and $Y^2$ are each OH. In particular embodiments, the present invention provides a method for the prevention or treatment of a neurodegenerative disease, wherein the method comprises administering to a subject in need thereof a therapeutically effective amount of a compound represented by the structure of formula I, wherein A is H, Z is S, $Y^3$ and $Y^4$ are each OH, and $X^1$ is a halogen selected from Br and I. Each possibility represents a separate embodiment of the present invention.

Representative and non-limiting examples of such structures are compounds selected from the group consisting of compounds 1-8:

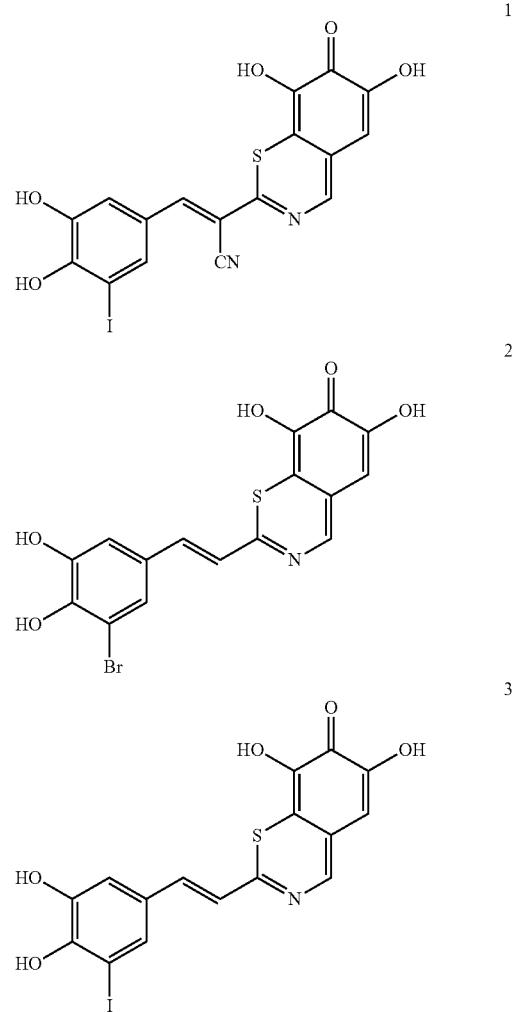

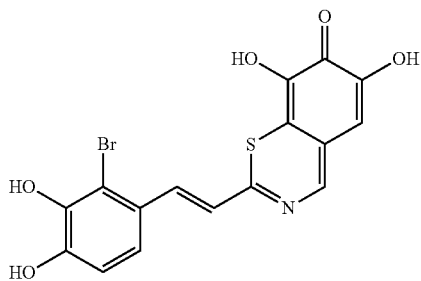

4

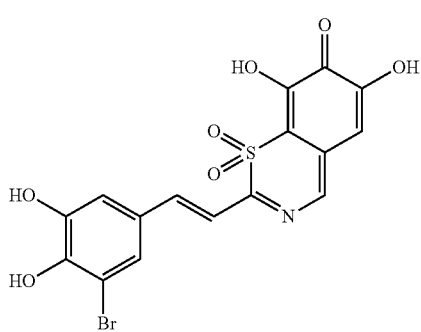

5

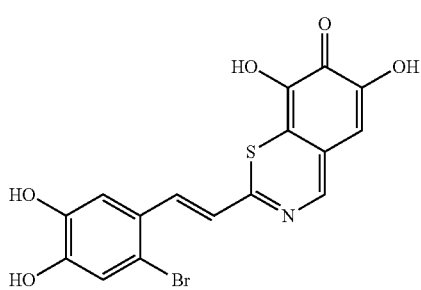

6

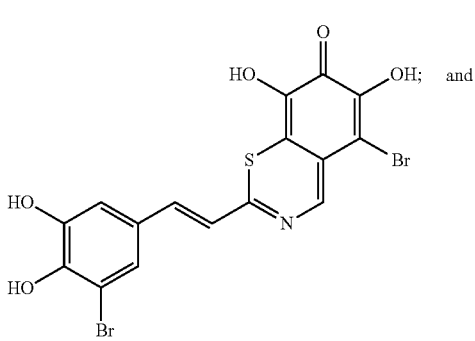

7

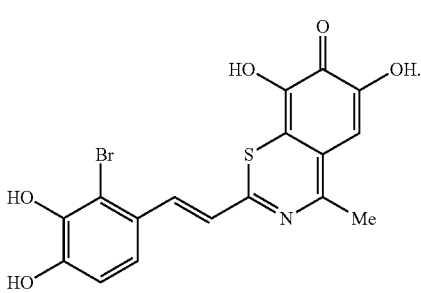

8

According to some other embodiments, the compounds to be used for the treatment of neurodegenerative disease are tyrphostin derivatives represented by the general structure of formula II. Any tyrphostin derivative of the general structure of formula II can be used in the compositions of the present invention:

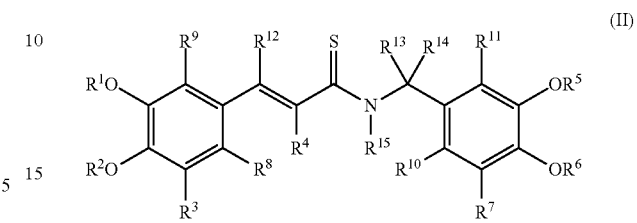

(II)

wherein $R^1$, $R^2$, $R^5$ and $R^6$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $(CH_2CH_2O)_nH$, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, haloalkyl, acyl and a functional group that gives rise to hydroxyl upon hydrolysis;

$R^3$, $R^4$, $R^7$, $R^8$, $R^9$, $R^{10}$, $R^{11}$, $R^{12}$, $R^{13}$ and $R^{14}$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, halogen, haloalkyl, $NO_2$, CN, $N_3$, $SO_2R^a$, $COOR^a$, $CSNR^aR^b$, $CSOR^a$, $OR^a$, $CONR^aR^b$, $NR^aR^b$, $SR^a$, and $CH_2SR^a$, wherein $R^a$ and $R^b$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, haloalkyl, $(CH_2CH_2O)_nH$, acyl or a functional group that gives rise to hydroxyl upon hydrolysis; and $R^{15}$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, haloalkyl, or $OR^b$ wherein $R^b$ is independently H or $C_1$-$C_4$ alkyl; including salts, hydrates, solvates, polymorphs, optical isomers, geometrical isomers, enantiomers, diastereomers, and mixtures thereof. Each possibility represents a separate embodiment of the invention.

In an exemplary embodiment, the tyrphostin derivative is a compound represented by formula 29:

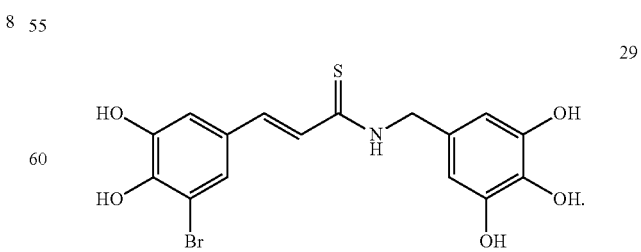

29

In another exemplary embodiment, the tyrphostin derivative is a compound represented by formula 28:

In another exemplary embodiment, the tyrphostin derivative is a compound represented by formula 28:

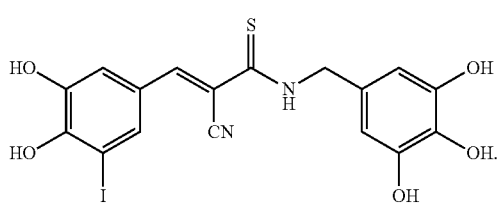

In another exemplary embodiment, the tyrphostin derivative is a compound represented by formula 30:

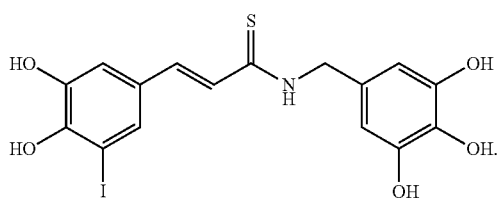

In another exemplary embodiment, the tyrphostin derivative is a compound represented by formula 39:

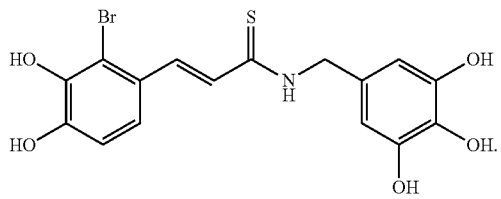

In another exemplary embodiment, the tyrphostin derivative is a compound represented by formula 33:

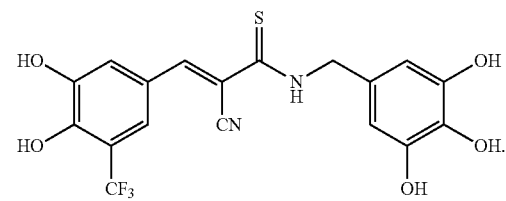

In another embodiment, the tyrphostin derivative is a compound of formula II wherein $R^1$, $R^2$, $R^4$, $R^5$, $R^6$, $R^{10}$, $R^{12}$, $R^{13}$, $R^{14}$ and $R^{15}$ are each H; $R^7$ is OH; and at least one of $R^3$, $R^8$, $R^9$ and $R^{11}$ is halogen.

In another embodiment, the tyrphostin derivative is a compound of formula II wherein $R^1$, $R^2$, $R^4$, $R^5$, $R^6$, $R^8$, $R^{10}$, $R^{12}$, $R^{13}$, $R^{14}$ and $R^{15}$ are each H; $R^7$ is OH; and at least one of $R^3$, $R^9$ and $R^{11}$ is halogen.

In another embodiment, the tyrphostin derivative is a compound of formula II wherein $R^1$, $R^2$, R and $R^6$ are each H or a functional group that gives rise to hydroxyl upon hydrolysis.

In another embodiment, the tyrphostin derivative is a compound of formula II wherein $R^7$ is H or $OR^a$ and $R^1$, $R^2$, $R^5$, $R^6$, and $R^a$ are each H or a functional group that gives rise to hydroxyl upon hydrolysis.

In another embodiment, the tyrphostin derivative is a compound of formula II wherein $R^{13}$ and $R^{14}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl or $C_1$-$C_4$ alkyl-$C_2$-$C_6$ alkynyl.

In another embodiment, the tyrphostin derivative is a compound of formula II wherein at least one of $R^{13}$ and $R^{14}$ is H or $C_1$-$C_4$ alkyl.

In another embodiment, the tyrphostin derivative is a compound of formula II wherein $R^3$, $R^4$, $R^7$, $R^8$, $R^9$, $R^{10}$, $R^{11}$, $R^{12}$, $R^{13}$ and $R^{14}$ are each independently H, halogen, haloalkyl, OH, $NO_2$, CN, or $CH_2SR^a$, wherein $R^a$ is as defined hereinabove.

In another embodiment, the tyrphostin derivative is a compound of formula II wherein $R^4$ is H.

In another embodiment, the tyrphostin derivative is a compound of formula II wherein $R^4$ is CN.

In another embodiment, the tyrphostin derivative is a compound of formula II wherein $R^4$, $R^{11}$, $R^{12}$, $R^{13}$, $R^{14}$ and $R^{15}$ are each H.

In another embodiment, the tyrphostin derivative is a compound of formula II wherein $R^{13}$, $R^{14}$ and $R^{15}$ are each H.

In another embodiment, the tyrphostin derivative is a compound of formula II wherein $R^3$, $R^7$, $R^8$, $R^9$, $R^{10}$ and $R^{11}$ are each independently H, halogen, haloalkyl, $CH_2SR^a$ or OH; $R^4$, $R^{12}$, $R^{13}$ and $R^{14}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, aryl, halogen, haloalkyl, $NO_2$, or CN; and $R^{15}$ is H.

In another embodiment, the tyrphostin derivative is a compound of formula II wherein $R^3$, $R^7$, $R^8$, $R^9$, $R^{10}$ and $R^{11}$ are each independently H, halogen, haloalkyl, OH or $CH_2SR^a$; and $R^4$, $R^{12}$, $R^{13}$, $R^{14}$ and $R^{15}$ are each H, or a $C_1$-$C_4$ alkyl.

In another embodiment, the tyrphostin derivative is a compound of formula II wherein $R^1$, $R^2$, $R^5$ and $R^6$ are each H or a functional group that gives rise to hydroxyl upon hydrolysis; $R^3$, $R^8$, and $R^9$ are each independently H, halogen, haloalkyl, or $CH_2SR^a$; $R^7$, $R^{10}$ and $R^{11}$ are each independently H, halogen, haloalkyl, OH or a functional group that gives rise to hydroxyl upon hydrolysis; and $R^4$, $R^{12}$, $R^{13}$, $R^{14}$ and $R^{15}$ are each H, or $C_1$-$C_4$ alkyl.

In another embodiment, the tyrphostin derivative is a compound of formula II wherein the compound is represented by any one of the structures:

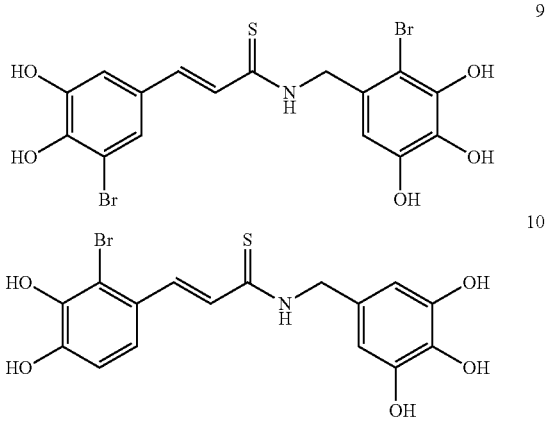

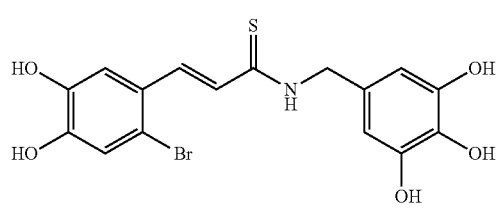
11
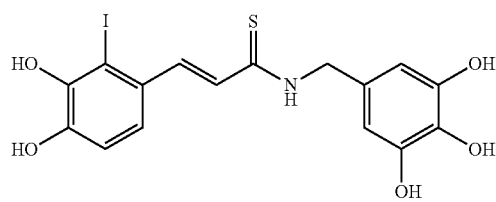
12
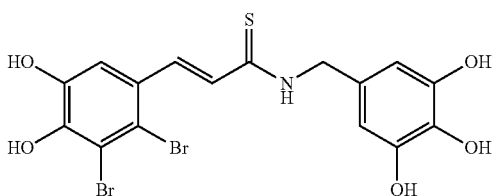
13a
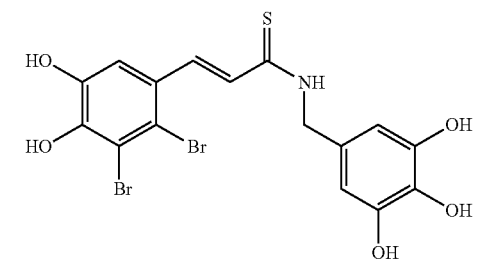
13b
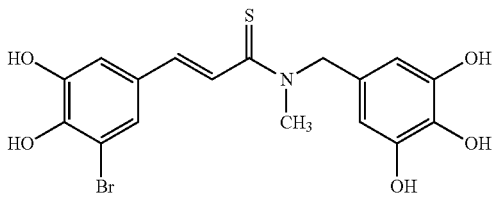
14a
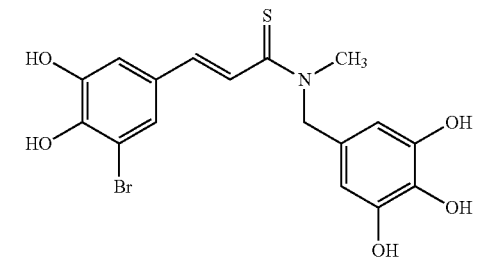
14b
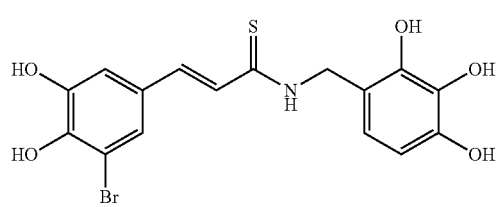
15
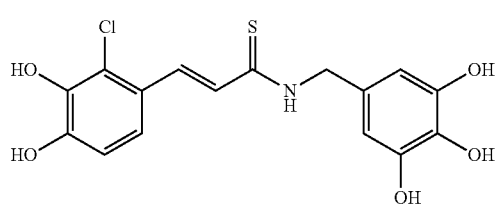
16
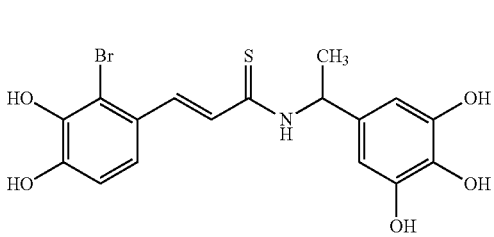
17a
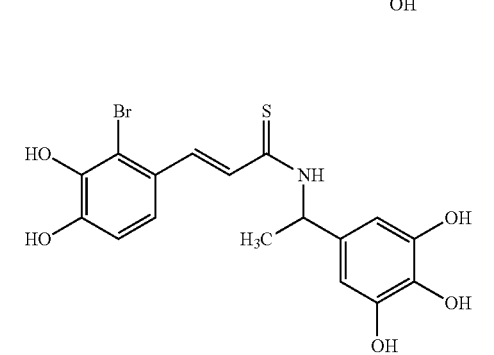
17b
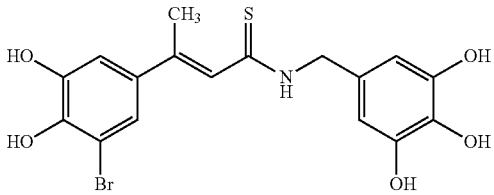
18a
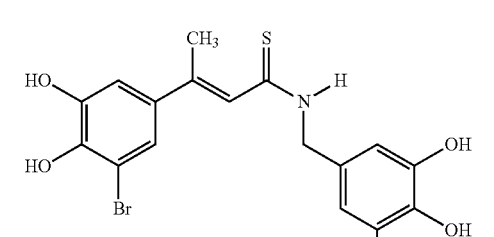
18b
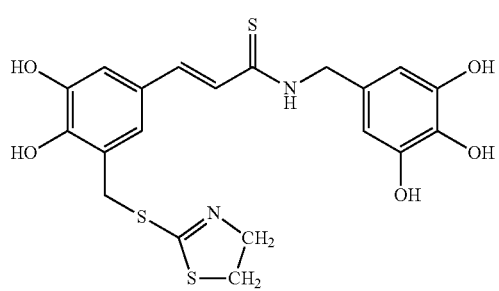
19

23
-continued

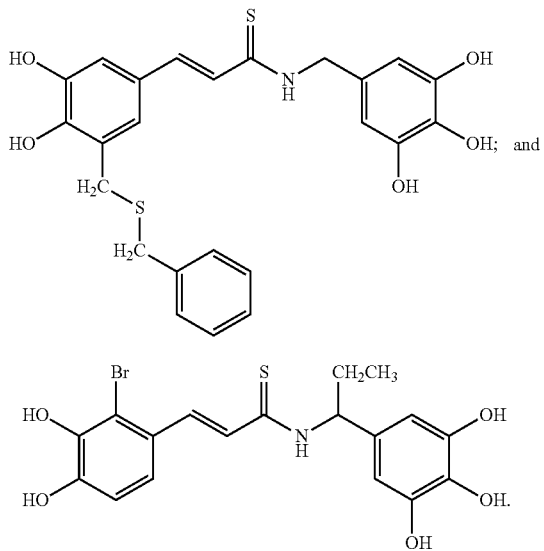

Each possibility represents a separate embodiment of the present invention.

In other embodiments, the tyrphostin derivative is a compound represented by the structure of formula II:

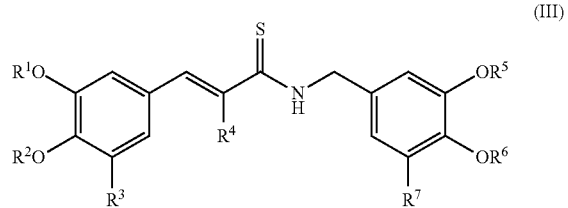

(III)

wherein
$R^1$, $R^2$, $R^5$ and $R^6$ are independently selected from H, $C_1$-$C_4$ alkyl, acyl and a functional group that gives rise to hydroxyl upon hydrolysis;
$R^3$ and $R^7$ are independently selected from H, halogen, haloalkyl and $OR^8$ wherein $R^8$ is H, $C_1$-$C_4$ alkyl, acyl or a functional group that gives rise to hydroxyl upon hydrolysis;
$R^4$ is H or CN,
including salts, hydrates, solvates, polymorphs, optical isomers, geometrical isomers, enantiomers, diastereomers, and mixtures thereof.

In other embodiments, the tyrphostin derivative is a compound represented by the structure of formula III, wherein
$R^1$, $R^2$, $R^5$ and $R^6$ are independently selected from H, $C_1$-$C_4$ alkyl, $(CH_2CH_2O)_n$, wherein n is an integer of 1 to 20, acyl and a functional group that gives rise to hydroxyl upon hydrolysis;
$R^3$ and $R^7$ are independently selected from H, halogen, $C_1$-$C_4$ alkyl, haloalkyl and $OR^{16}$ wherein $R^{16}$ is H, $C_1$-$C_4$ alkyl, $(CH_2CH_2O)_n$, acyl or a functional group that gives rise to hydroxyl upon hydrolysis; and
$R^4$ is H or CN,
including salts, hydrates, solvates, polymorphs, optical isomers, geometrical isomers, enantiomers, diastereomers, and mixtures thereof.

24

Each possibility represents a separate embodiment of the present invention.

In another embodiment, the tyrphostin derivative is a compound of formula III wherein $R^4$ is CN.

In other embodiments, the tyrphostin derivative is a compound of formula III wherein $R^1$, $R^2$, $R^5$ and $R^6$ are each hydrogen.

In other embodiments, the tyrphostin derivative is a compound of formula III wherein $R^1$, $R^2$, $R^5$ and $R^6$ are each $CH_3$.

In other embodiments, the tyrphostin derivative is a compound of formula III wherein $R^3$ and $R^7$ are each a hydrogen, halogen, halomethyl, OH or $OCH_3$.

In other embodiments, the tyrphostin derivative is a compound of formula III wherein $R^1$, $R^2$, $R^5$ and $R^6$ are each H, $R^3$ is halogen and $R^7$ is OH.

In other embodiments, the tyrphostin derivative is a compound of formula III wherein $R^1$, $R^2$, $R^5$ and $R^6$ are each H, and $R^3$ and $R^7$ are each halogen.

In other embodiments, the tyrphostin derivative is a compound of formula III wherein $R^1$, $R^2$, $R^5$ and $R^6$ are each H, $R^3$ is halomethyl and $R^7$ is OH.

In other embodiments, the tyrphostin derivative is a compound of formula III wherein $R^1$, $R^2$, $R^5$ and $R^6$ are each H, $R^3$ is halogen and $R^7$ is H.

In other embodiments, the tyrphostin derivative is a compound of formula III wherein $R^1$, $R^2$, $R^5$ and $R^6$ are each H, $R^3$ is OH and $R^7$ is halogen.

In other embodiments, the tyrphostin derivative is a compound of formula III wherein $R^1$, $R^2$, $R^5$ and $R^6$ are each $CH_3$, $R^3$ is halogen and $R^7$ is $OCH_3$.

In other embodiments, the tyrphostin derivative is a compound of formula III wherein $R^1$, $R^2$, $R^5$ and $R^6$ are each $CH_3$, and $R^3$ and $R^7$ are each halogen.

In other embodiments, the tyrphostin derivative is a compound of formula III wherein $R^4$ is hydrogen.

In other embodiments, the tyrphostin derivative is a compound of formula III wherein $R^1$, $R^2$, $R^5$ and $R^6$ are each hydrogen.

In other embodiments, the tyrphostin derivative is a compound of formula III wherein $R^1$, $R^2$, $R^5$ and $R^6$ are each $CH_3$.

In other embodiments, the tyrphostin derivative is a compound of formula III wherein $R^3$ and $R^7$ are each hydrogen, halogen, halomethyl, OH or $OCH_3$.

In other embodiments, the tyrphostin derivative is a compound of formula III wherein $R^1$, $R^2$, $R^5$ and $R^6$ are each H, $R^3$ is halogen and $R^7$ is OH.

In other embodiments, the tyrphostin derivative is a compound of formula III wherein $R^1$, $R^2$, $R^5$ and $R^6$ are each H, and $R^3$ and $R^7$ are each halogen.

In other embodiments, the tyrphostin derivative is a compound of formula III wherein $R^1$, $R^2$, $R^5$ and $R^6$ are each H, $R^3$ is halomethyl and $R^7$ is OH.

In other embodiments, the tyrphostin derivative is a compound of formula III wherein $R^1$, $R^2$, $R^5$ and $R^6$ are each H, $R^3$ is halogen and $R^7$ is H.

In other embodiments, the tyrphostin derivative is a compound of formula III wherein $R^1$, $R^2$, $R^5$ and $R^6$ are each H, $R^3$ is OH and $R^7$ is halogen.

In other embodiments, the tyrphostin derivative is a compound of formula III wherein $R^3$ is halogen and $R^7$ is $OCH_3$.

In other embodiments, the tyrphostin derivative is a compound of formula III wherein $R^1$, $R^2$, $R^5$ and $R^6$ are each $CH_3$, and $R^3$ and $R^7$ are each halogen.

In other embodiments, the tyrphostin derivative of formula (III) is represented by any of the following compounds:
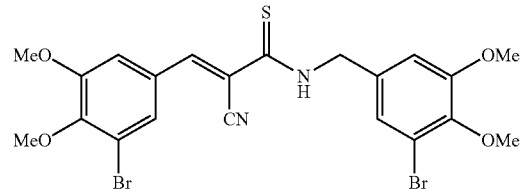
22
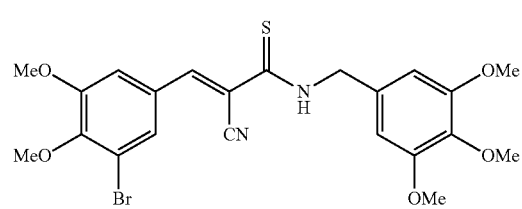
23
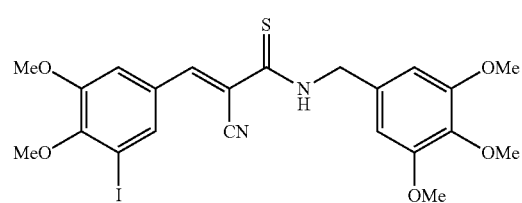
24
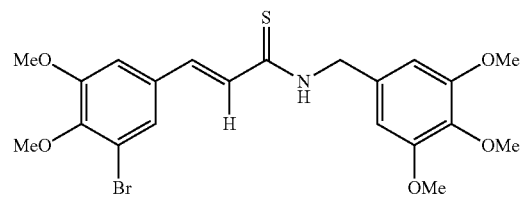
25
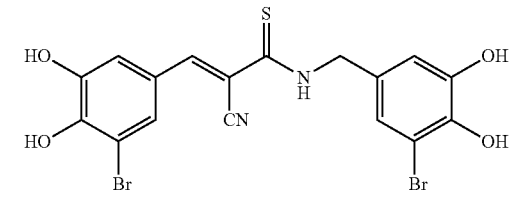
26
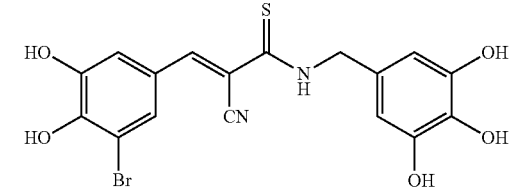
27
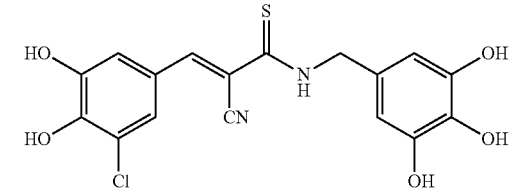
31
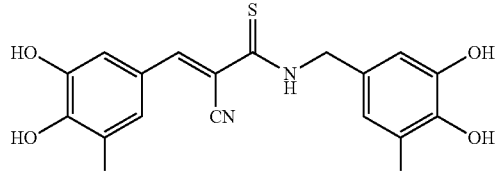
32
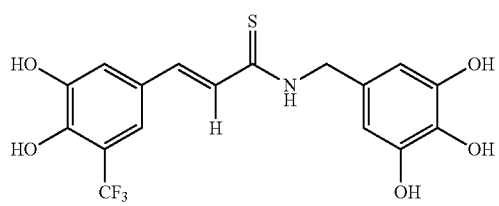
34
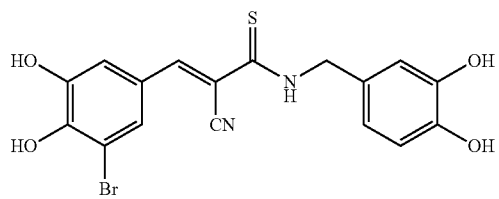
35
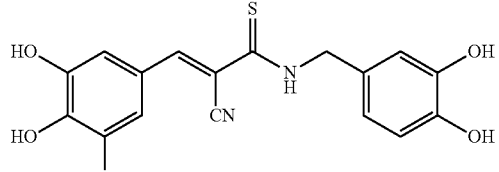
36
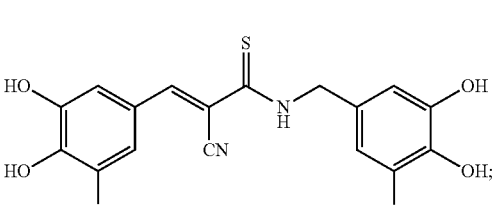
37; and
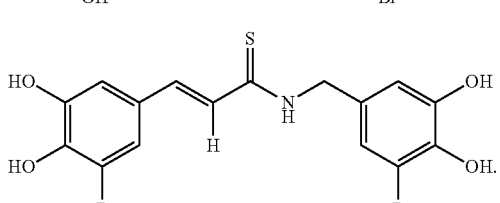
38
Each possibility represents a separate embodiment of the present invention.
In another embodiment, the tyrphostin compound is represented by the structure of formula IV:
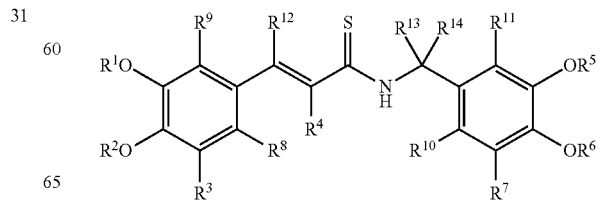
(IV)

wherein $R^1$, $R^2$, $R^5$ and $R^6$ are independently selected from H, $C_1$-$C_4$ alkyl, $(CH_2CH_2O)_n$, wherein n is an integer of 1 to 20, acyl and a functional group that gives rise to hydroxyl upon hydrolysis;

$R^3$, $R^7$, $R^8$, $R^9$, $R^{10}$, $R^{11}$, $R^{12}$, $R^{13}$ and $R^{14}$ are independently selected from H, halogen, $C_1$-$C_4$ alkyl, haloalkyl and $OR^{16}$ wherein $R^{16}$ is H, $C_1$-$C_4$ alkyl, $(CH_2CH_2O)_n$, acyl or a functional group that gives rise to hydroxyl upon hydrolysis; and $R^4$ is H or CN.

In other embodiments, the tyrphostin derivative is any of the derivatives described in A) PCT International Patent Application Publication No. WO 2008/068751; or B) PCT International Patent Application Publication No. WO2009/147682. The contents of each of the aforementioned references are incorporated by reference herein in their entirety as if fully set forth herein.

It is understood that all conformers, geometrical isomers, stereoisomers, enantiomers and diastereomers of any of the tyrphostin derivatives described herein, are encompassed and may be used in the combinations and methods described by the present application.

Chemical Definitions

An "alkyl" group refers to any saturated aliphatic hydrocarbon, including straight-chain, branched-chain and cyclic alkyl groups. In one embodiment, the alkyl group has 1-12 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

An "alkenyl" group refers to an aliphatic hydrocarbon group containing at least one carbon-carbon double bond including straight-chain, branched-chain and cyclic alkenyl groups. In one embodiment, the alkenyl group has 2-8 carbon atoms designated here as $C_2$-$C_8$-alkenyl. In another embodiment, the alkenyl group has 2-6 carbon atoms in the chain designated here as $C_2$-$C_6$-alkenyl. Exemplary alkenyl groups include ethenyl, propenyl, n-butenyl, i-butenyl, 3-methylbut-2-enyl, n-pentenyl, heptenyl, octenyl, cyclohexyl-butenyl and decenyl. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 2-8 carbon atoms in the chain designated here as $C_2$-$C_8$-alkynyl. In another embodiment, the alkynyl group has 2-6 carbon atoms in the chain designated here as $C_2$-$C_6$-alkynyl. Exemplary alkynyl groups include ethynyl, propynyl, n-butynyl, 2-butynyl, 3-methylbutynyl, n-pentynyl, heptynyl, octynyl and decynyl. The alkynyl group can be unsubstituted or substituted through available carbon atoms with one or more groups defined hereinabove for alkyl.

The term "$C_3$-$C_7$ cycloalkyl" used herein alone or as part of another group refers to any saturated or unsaturated (e.g., cycloalkenyl, cycloalkynyl) monocyclic or polycyclic group. Non-limiting examples of cycloalkyl groups are cyclopropyl, cyclobutyl, cyclopentyl, cyclohexyl or cycloheptyl. Non-limiting examples of cycloalkenyl groups include cyclopentenyl, cyclohexenyl and the like. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups.

The term "aryl" used herein alone or as part of another group refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "heteroaryl" used herein alone or as part of another group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. If nitrogen is a ring atom, the present invention also contemplates the N-oxides of the nitrogen containing heteroaryls. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

The term "heterocyclic ring" or "heterocyclyl" used herein alone or as part of another group refers to a five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings can be saturated, fully unsaturated or partially unsaturated, with fully saturated rings being preferred. Preferred heterocyclic rings include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, dihydrothiazolyl, and the like. The heterocyclyl group can be unsubstituted or substituted through available atoms with one or more groups defined hereinabove for alkyl.

The term "acyl" as used herein encompasses groups such as, but not limited to, formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Currently preferred acyl groups are acetyl and benzoyl.

A "hydroxy" group refers to an OH group. An "alkoxy" group refers to an —O-alkyl group wherein R is alkyl as defined above.

A "thio" group refers to an —SH group. An "alkylthio" group refers to an —SR group wherein R is alkyl as defined above.

An "amino" group refers to an $NH_2$ group. An alkylamino group refers to an —NHR group wherein R is alkyl as defined above. A dialkylamino group refers to an —NRR' group wherein R and R' are alkyl as defined above.

An "amido" group refers to a —C(O)$NH_2$ group. An alkylamido group refers to an —C(O)NHR group wherein R is alkyl is as defined above. A dialkylamido group refers to an —C(O)NRR' group wherein R and R' are alkyl as defined above.

A "thioamide" group refers to a —C(S)NHR group, where R is either alkyl, aryl, alkylaryl or H.

A "polyoxyalkylene" group refers to a $(CH_2CH_2O)_nH$ group wherein n=1-20. Currently preferred polyoxyalkylene groups are polyethyleneglycol (PEG) and polypropyleneglycole.

The term "halogen" or "halo" as used herein alone or as part of another group refers to chlorine, bromine, fluorine, and iodine. The term "haloalkyl" refers to an alkyl group having some or all of the hydrogens independently replaced by a halogen group including, but not limited to, trichloromethyl, tribromomethyl, trifluoromethyl, triiodomethyl, difluoromethyl, chlorodifluoromethyl, pentafluoroethyl, 1,1-difluoroethyl bromomethyl, chloromethyl, fluoromethyl, iodomethyl, and the like.

Examples of functional groups that give rise to hydroxyl upon hydrolysis include, but are not limited to, esters, anhydrides, carbamates, carbonates and the like. For example, when any of $R^1$, $R^2$, $R^5$ or $R^6$ is an acyl group (COR), the resulting functional group is an ester (OCOR). When any of $R^1$, $R^2$, $R^5$ or $R^6$ is an amide group (CONHR), the resulting functional group is a carbamate (OCONHR). When any of $R^1$, $R^2$, $R^5$ or $R^6$ is a carboxylate group (COOR), the resulting functional group is a carbonate (OCOOR).

Within the scope of the present invention are prodrugs of the compounds disclosed herein. The term "prodrug" represents compounds which are rapidly transformed in vivo to any of compounds represented by formula 1, 2 or 3 or any of compounds 4-16, for example by hydrolysis in the blood. Thus, the term "prodrug" refers to a precursor of any of the compounds of the present invention that is pharmaceutically acceptable. A prodrug may be inactive when administered to a subject, but is converted in vivo to an active compound. The use of prodrugs is particularly advantageous for facilitating the administration of the compounds. The prodrug compound often offers benefits of solubility, tissue compatibility or delayed release in a mammalian organism. For example the prodrug, according to the principles of the present invention, can be a compound represented by the structure of formula 1 wherein $R^1$, $R^2$, $R^5$ and $R^6$ are a functional group that gives rise to hydroxyl upon hydrolysis as defined hereinabove.

All stereoisomers of the compounds of the present invention are contemplated, either in admixture or in pure or substantially pure form. These compounds can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L. In addition, several of the compounds of the present invention contain one or more double bonds. The present invention intends to encompass all structural and geometrical isomers including cis, trans, E and Z isomers and optical isomers, independently at each occurrence.

One or more of the compounds of the invention, may be present as a salt. The term "salt" encompasses both basic and acid addition salts, including but not limited to carboxylate salts or salts with amine nitrogens, and include salts formed with the organic and inorganic anions and cations discussed below. Further encompassed by the term are salts formed by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and the like.

The term "organic or inorganic cation" refers to counter-ions for the carboxylate anion of a carboxylate salt. The counter-ions are chosen from the alkali and alkaline earth metals (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, Berge et al., *J. Pharm. Sci.* (1977), 66:1-19, which is incorporated herein by reference. Other cations encompassed by the above term include the protonated form of procaine, quinine and N-methylglucosamine. Furthermore, any zwitterionic form of the instant compounds formed by a carboxylic acid and an amino group is also contemplated.

The present invention also includes solvates of any of compounds represented by formulae I-IV or any of compounds 1-39 and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of any of compounds represented by formulae I-IV or any of compounds 1-39 and salts thereof. The term "polymorph" refers to a particular crystalline state of a substance, which can be characterized by particular physical properties such as X-ray diffraction, IR spectra, melting point, and the like.

Therapeutic Use

The present invention provides compounds and compositions comprising compounds effective in modulating IGF-1R signaling. These compounds and compositions are useful in the treatment of neurodegenerative diseases associated with the activity or signaling of IGF-1R such as enhanced activity or signaling of IGF-1R. In some embodiments, the compounds of the invention trigger any one or more of the following, in any order: (i) serine phosphorylation of the IGF-1R direct substrates IRS1 and/or IRS2; (ii) dissociation of IRS1 and/or IRS2 from the cell membrane; and/or (iii) degradation of IRS1 and/or IRS2, thus providing long-lasting effects which enhance the inhibitory activity of these compounds.

In particular these compounds and compositions are useful in protection from proteotoxicity (for example: Aβ proteotoxicity). Without wishing to be bound by theory or mechanism of action it is assumed that IGF-1R signaling reduction either early or late in life, can protect from age onset proteotoxicity by invoking a mechanism that converts toxic aggregates into larger, less toxic high molecular weight aggregates.

Thus, in one embodiment, the present invention provides a method of inhibiting signal transduction mediated by a IGF-1R in a cell comprising contacting the cell with an effective inhibitory amount of at least one compound represented by the structure of formulae I-IV, or at least one compound selected from compounds 1-39, or a pharmaceutical composition comprising one or more of such compounds as an active ingredient.

In another embodiment, the present invention provides a method of inhibiting toxic protein aggregation or proteotoxicity in a subject comprising administering to a subject an effective inhibitory amount of at least one compound represented by the structure of formulae I-IV or at least one compound selected from compounds 1-39.

The present invention further provides a method of inhibiting, treating or preventing a neurodegenerative disease characterized by toxic protein aggregation in a subject comprising the step of administering to the subject a therapeutically effective amount of at least one compound represented by the structure of formulae I-IV, or at least one compound selected from compounds 1-39. In another embodiment, the method comprises administering to the subject a pharmaceutical composition comprising a therapeutically effective amount of at least one compound represented by the structure of formulae I-IV, or at least one compound selected from compounds 1-39 and a pharmaceutically acceptable carrier or excipient.

The pharmaceutical compositions comprising at least one compound represented by the structure of formulae I-IV or at least one compound selected from compounds 1-39 in therapeutically effective amount and a pharmaceutically acceptable carrier or excipient are useful for inhibiting, treating or preventing a disorder selected from Amyloidosis, Prion disorders, Motor Neuron disease, Alzheimer's disease, Fronto temporal dementia 17 (FTD17), Huntington's disease (HD) and Parkinson's disease. Each possibility represents a separate embodiment of the present invention. Non limiting examples of Amyloidosis diseases include AL amyloidosis, AA amyloidosis, familial amyloid polyneuropathies, senile systemic amyloidosis, Leptomeningeal amyloidosis, Haemodialysis-associated amyloidosis, Finnish type amyloidosis, Cerebral amyloid angiopathy; Familial visceral amyloidosis; Familial corneal amyloidosis; Primary cutaneous amyloidosis and Senile amyloid of atria of heart. Non limiting examples of prion disorders include Finnish type amyloidosis; creutzfeldt-Jakob disease, kuru, fatal familiar insomnia and Gerstmann-Straussler-Scheinker disease.

Additional neurodegenerative diseases that may be treated by the methods of the current invention are dementia with Lewy bodies (DLB), the Lewy body variant of Alzheimer's disease (LBVAD), multiple systems atrophy (MSA), and neurodegeneration with brain iron accumulation type-1 (NBIA-1)].

The term "treating" as used herein refers to abrogating, inhibiting, slowing or reversing the progression of a disease, ameliorating clinical symptoms of a disease or preventing the appearance of clinical symptoms of a disease. The term "Preventing" or "prevention" of a disease or disorder means prevention of the occurrence or onset of a disease or disorder or some or all of its symptoms.

The term "treatment of a neurodegenerative disease" in the context of the present invention includes at least one of the following: protection from proteotoxicity possibly by promoting accumulation of high molecular weight protein aggregates; and elevated stress resistance. The term also includes protection from the neurodegenerative disease symptoms including reduced behavioral impairment, reduced neuroinflammation, and reduced neuronal loss.

The term "administering" as used herein refers to bringing into contact with a compound of the present invention thus affecting the activity, activation or signaling of the IGF-1R either directly; i.e. by interacting with IGF-1R itself, or indirectly; i.e. by interacting with another molecule on which the IGF-1 signaling is dependent. As used herein, administration can be accomplished in vitro, i.e. in a test tube, or in vivo, i.e. in cells or tissues of living organisms, for example humans. In one embodiment, the present invention encompasses administering the compounds of the present invention to a subject, preferably the subject is a mammal, more preferably the subject is human.

The term "therapeutically effective amount" refers to the amount of a compound being administered which provides a therapeutic effect for a given condition and administration regimen, specifically an amount which relieves to some extent one or more of the symptoms of the disorder being treated. Therapeutic effective doses for any compounds represented by the structure of formulae I, II, or any of the compounds 1-39 described herein can be estimated initially from cell culture and/or an animal model. A dose can be formulated in an animal model, and this dose can be used to more precisely determine useful doses in humans.

The term "effective inhibitory amount" refers to the amount of a compound being administered that inhibits to some extent IGF-1 Receptor with which it is contacted; alternatively it refers to the amount of a compound being administered that reduces proteotoxicity possibly by promoting accumulation of high molecular weight protein aggregates; alternatively it refers to the amount of a compound being administered that causes a reduction of behavioral impairment and/or reduced neuroinflammation and/or reduced neuronal loss in a subject as compared to the subject's condition prior to compound intake.

Pharmaceutical Compositions:

The present invention further provides pharmaceutical compositions useful in the treatment of a neurodegenerative disease, comprising at least one compound represented by the structure of formulae I, II, or at least one compound selected from compounds 1-39, and a pharmaceutically acceptable carrier or excipient. As used herein, "pharmaceutical composition" means therapeutically effective amounts of the compounds of the present invention, together with suitable diluents, preservatives, solubilizers, emulsifiers, adjuvant and/or carriers. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Further contemplated by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral. In one embodiment, the pharmaceutical composition is administered parenterally, paracancerally, transmucosally, transdermally, intramuscularly, intravenously, intradermally, subcutaneously, intraperitonealy, intraventricularly, intracranially or intratumorally.

Moreover, as used herein "pharmaceutically acceptable carriers" are well known to those skilled in the art and include, but are not limited to, 0.01-0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions include formulation in lipophilic depots (e.g. fatty acids, waxes, oils). Also contemplated by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions of the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see for example Saudek et al., *N. Engl. J. Med.* (1989), 321:574-579). In another embodiment, polymeric materials can be used. In yet another embodiment, a controlled release system can be placed in proximity to the therapeutic target, i.e., the brain, thus requiring only a fraction of the systemic dose (see, e.g., Goodson, *Medical Applications of Controlled Release*, supra (1984), 2:115-138). Preferably, a controlled release device is introduced into a subject in proximity to the site of inappropriate immune activation or a tumor. Other controlled release systems are discussed in the review by Langer, *Science* (1990), 249: 1527-1533.

The pharmaceutical preparation may comprise one or more of the compounds represented by the structure of formulae I, II, or any of the compounds 1-39, or may further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the receptor modulator can be administered to a subject by, for example, subcutaneous implantation of a pellet; in a further embodiment, the pellet provides for controlled release of receptor modulator over a period of time. The preparation can also be administered by intravenous, intra-arterial, or intramuscular injection of a liquid preparation, oral administration of a liquid or solid preparation, or by topical application. Administration can also be accomplished by use of a rectal suppository or a urethral suppository.

The pharmaceutical preparations of the invention can be prepared by known dissolving, mixing, granulating, or tablet-forming processes. For oral administration, the receptor modulators or their physiologically tolerated derivatives such as salts, esters, N-oxides, and the like are mixed with additives customary for this purpose, such as vehicles, stabilizers, or inert diluents, and converted by customary methods into a suitable form of administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, or with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intra-arterial, or intramuscular injection), the compounds of the present invention or their physiologically tolerated derivatives such as salts, hydrates and the like are converted into a solution, suspension, or emulsion, if desired with the substances customary and suitable for this purpose, for example, solubilizers or other auxiliaries. Examples are sterile liquids such as water and oils, with or without the addition of a surfactant, and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycols are preferred liquid carriers, particularly for injectable solutions.

The preparation of pharmaceutical compositions which contain an active component is well understood in the art. Typically, such compositions are prepared as aerosols of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically acceptable and compatible with the active ingredient. Suitable excipients are, for example, water, saline, dextrose, glycerol, ethanol, or the like and combinations thereof.

In addition, if desired, the composition can contain minor amounts of auxiliary substances such as wetting or emulsifying agents, pH buffering agents, which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the compounds of the present invention or their physiologically tolerated derivatives such as salts, hydrates, and the like are prepared and applied as solutions, suspensions, or emulsions in a physiologically acceptable diluent with or without a pharmaceutical carrier.

In another embodiment, the active compound can be delivered in a vesicle, in particular a liposome (see for example Langer, *Science* (1990), 249: 1527-1533; Treat et al., *Liposomes in the Therapy of Infectious Disease and Cancer* (1989), Lopez-Berestein and Fidler (eds.), Liss, N.Y., 353-365).

The pharmaceutical compositions of the present invention may further comprise any of the conventional excipients such as stabilizers, tonicity modifiers, buffering agents, preservatives, disintegrating agents, diluents, binders, emulsifying agents, lubricants, wetting agents, and complexing agents as defined herein above.

It should be noted that the term "and" or the term "or" are generally employed in its sense including "and/or" unless the content clearly dictates otherwise.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

Example 1: Synthesis—General Procedure

The compounds of formula (I) can generally be prepared by oxidation of general precursors of formula (V) as set forth in the scheme below:

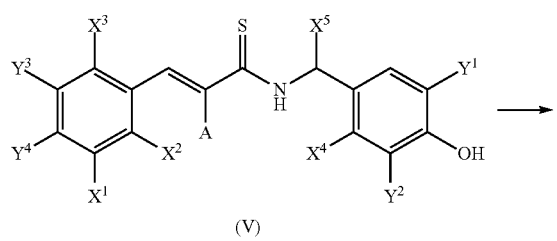

(V)

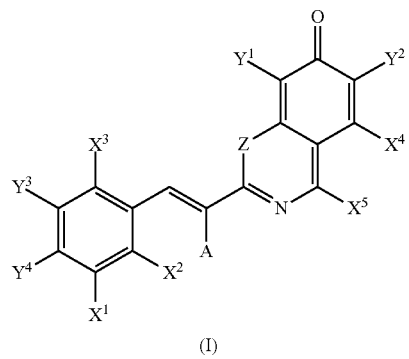

(I)

The precursor of formula (V) was reacted with an oxidizing agent, e.g., a mixture of $H_2NaPO_4$ and $HNa_2PO_4$. Following incubation, the product was centrifuged and the precipitate was washed with (2-N-morpholine)-ethane sulphonic acid (MES) and water, and lyophilized to give a compound of formula (I) wherein Z=S. Further oxidation to the sulfoxide (Z=SO) or sulfone (Z=$SO_2$) can be performed as known to a person of skill in the art.

This procedure is exemplified for the preparation of compounds of formula 1-8:

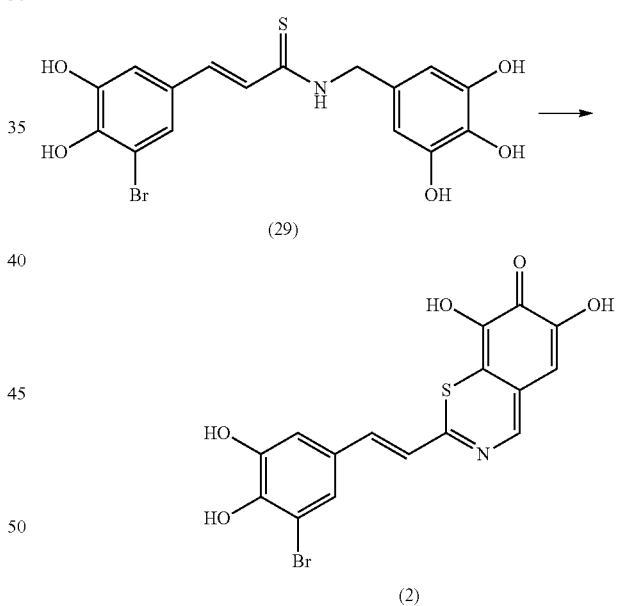

960 mg of compound no. 29 were dissolved in 10% ACN/DDW (4.8 lit). A mixture of 304 ml 0.2M $H_2NaPO_4$ and 1.3 ml 0.2M $HNa_2PO_4$ was added and the solution was stirred at room temperature for 1 hour, in which the solution changed its color from yellow to black. The reaction mixture was allowed to stay for at least 48 hours at 4° C. Following the incubation, the product was centrifuged. The precipitate was washed with 0.1M MES (2-(N-morpholine)-ethane sulphonic acid) pH~5, then with DDW and lyophilized to give compound 3 as a black powder (90%). The purity of compound 3 was >99% as detected by HPLC and by elemental microanalysis.

The assignment of the proton NMR signals of compound 2 is as follows:

¹H NMR (500 MHz, in DMSO-d$_6$): δ 8.25 (s, 1H), 7.71 (d, J=16 Hz, 1H), 7.51 (s, 1H), 7.15 (s, 1H), 7.12 (d, J=16 Hz, 1H), 6.80 (s, 1H). Represents only H atoms in C—H bonds. MS (ESI): found (m/z) 407.9. calculated for $C_{16}H_{10}BrNO_5S$ (MH$^+$) 407.95. Anal. ($C_{16}H_{10}BrNO_5S$) C, H, N, Br, S.

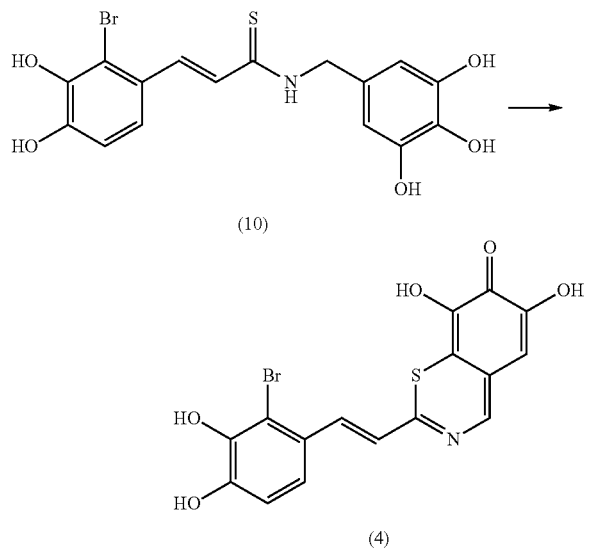 [SMILES: Oc1cc(Br)c(/C=C/C(=S)NCc2cc(O)c(O)c(O)c2)cc1O ; O=c1c(O)cc2cnc(/C=C/c3cc(O)c(O)cc3Br)sc-2c1O]

960 mg of compound no. 10 were dissolved in 10% ACN/DDW (4.8 lit). A mixture of 304 ml 0.2M H$_2$NaPO$_4$ and 1.3 L 0.2M HNa$_2$PO$_4$ was added and the solution was stirred at room temperature for 1 hour, in which the solution changed its color from yellow to black. The reaction mixture was allowed to stay for at least 48 hours at 4° C. Following the incubation, the product was centrifuged. The precipitate was washed with 0.1M MES (2-(N-morpholine)-ethane sulphonic acid) pH~5, then with DDW and finally lyophilized to give compound 5 as a black powder (55%). Compound 5 was obtained as a hydrate containing 1.5 molecules of water. The purity of compound 5 was >99% as detected by HPLC and by elemental microanalysis.

The assignment of the proton NMR signals of compound 4 is as follows:

¹H NMR (500 MHz, in DMSO-d$_6$): δ 8.25 (s, 1H), 8.12 (d, J=16 Hz, 1H), 7.45 (d, J=8 Hz, 1H), 7.17 (d, J=16 Hz 1H), 6.96 (s, 1H), 6.80 (d, J=8 Hz 1H). Represents only H atoms in C—H bonds. MS (ESI): found (m/z) 407.9. calculated for $C_{16}H_{10}BrNO_5S$ (MH$^+$) 407.95. Anal. ($C_{16}H_{10}BrNO_5S$) C, H, N, Br, S.

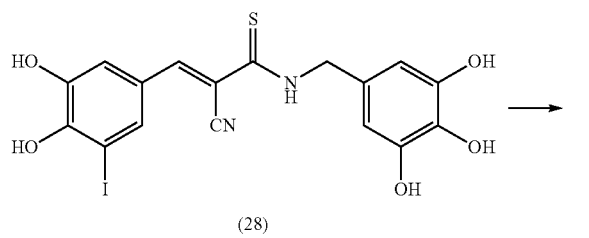

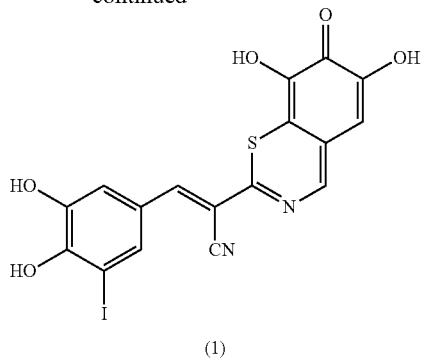

120 mg of compound no. 28 were dissolved in 10% ACN/DDW (1.2 lit). A mixture of 76 ml 0.2M H$_2$NaPO$_4$ and 325 ml 0.2M HNa$_2$PO$_4$ was added and the solution was stirred at room temperature for 1 hour, in which the solution changed its color from yellow to black. The reaction mixture was allowed to stay for at least 48 hours at 4° C. Following the incubation, the product was centrifuged. The precipitate was washed with 0.1M MES (2-(N-morpholine)-ethane sulphonic acid) pH~5, then with DDW and finally lyophilized to give compound 2 as a dark brown powder (34%). The purity of compound 2 was 80% as detected by HPLC and by elemental microanalysis.

The assignment of the proton NMR signals of compound 1 is as follows:

¹H NMR (500 MHz, in DMSO-d$_6$): δ 8.20 (s, 1H), 8.07 (s, 1H), 8.03 (s, 1H), 7.71 (s, 1H), 6.95 (s, 1H). Represents only H atoms in C—H bonds. MS (ESI): found (m/z) 480.93. calculated for $C_{17}H_{10}IN_2O_5S$ (MH$^+$) 480.93.

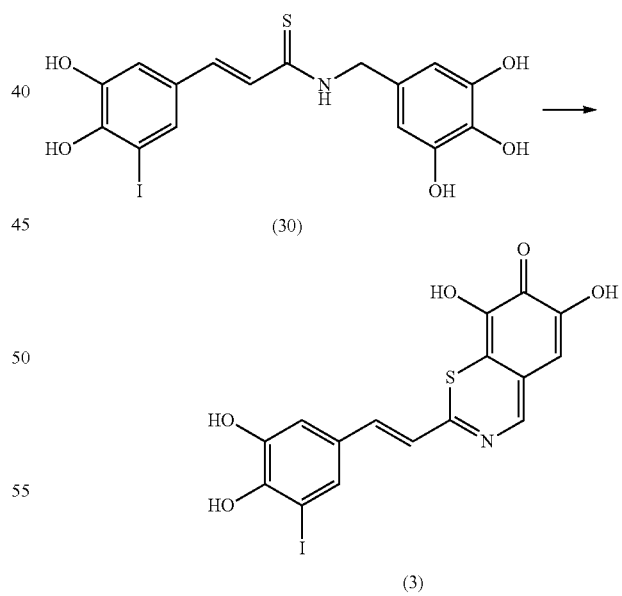

240 mg of compound no. 30 were dissolved in 10% ACN/DDW (1.2 lit). A mixture of 76 ml 0.2M H$_2$NaPO$_4$ and 325 ml 0.2M HNa$_2$PO$_4$ was added and the solution was stirred at room temperature for 1 hour, in which the solution changed its color from yellow to black. The reaction mixture was allowed to stay for at least 48 hours at 4° C. Following the incubation, the product was centrifuged. The precipitate was washed with 0.1M MES (2-(N-morpholine)-ethane sulphonic acid) pH~5, then with DDW and finally lyophilized to give compound 4 as a black powder (55%). The crude product was obtained at 90% purity. Further purification was performed by dissolving and stirring crude compound 4 in 3 ml MeOH and 100 L HCl 6N. After 20 minutes, the solution was filtered through silicagel 60, and neutralized to pH=7.5 with ammonium hydroxide. The dark precipitant obtained after 48 hours was filtered, washed with water and lyophilized. The purity of compound 4 was >99% as detected by HPLC and by elemental microanalysis.

The assignment of the proton NMR signals of compound 3 is as follows:

$^1$H NMR (500 MHz, in DMSO-d$_6$): δ 8.26 (s, 1H), 8.12 (d, J=16 Hz, 1H), 7.5 (d, J=1.5 Hz, 1H), 7.16 (d, J=1.5 Hz 1H), 7.09 (d, J=16, 1H), 6.99 (s, 1H). Represents only H atoms in C—H bonds. MS (ESI): found (m/z) 455.93. calculated for C$_{16}$H$_{10}$INO$_5$S (MH$^+$) 455.93.

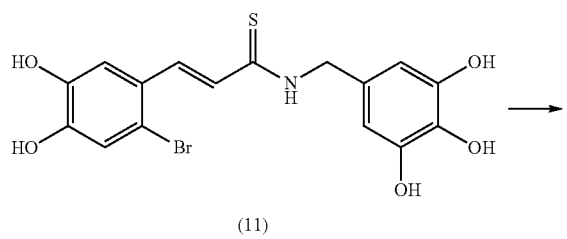

(11)

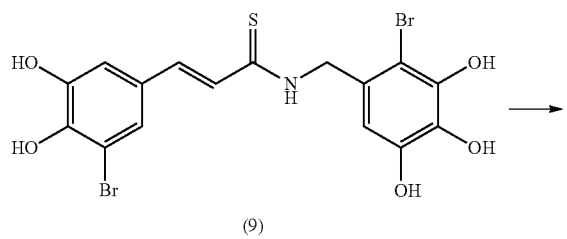

(6)

30 mg of compound no. 11 were dissolved in 10% ACN/DDW (8 ml). A mixture of 5 ml 0.2M H$_2$NaPO$_4$/HNa$_2$PO$_4$ buffer, pH=7.4 was added and the solution was stirred at room temperature for 1 hour, in which the solution changed its color from yellow to black. The reaction mixture was allowed to stay for at least 48 hours at 4° C. Following the incubation, the product was centrifuged. The precipitate was washed with 0.1M MES (2-(N-morpholine)-ethane sulphonic acid) pH~5, then with DDW and finally lyophilized to give compound 6 as a dark brown powder (30%). The purity of compound 6 was 70% as detected by HPLC.

MS (ESI): found (m/z) 407.95. calculated for C$_{16}$H$_{10}$BrNO$_5$S (MH$^+$) 407.95.

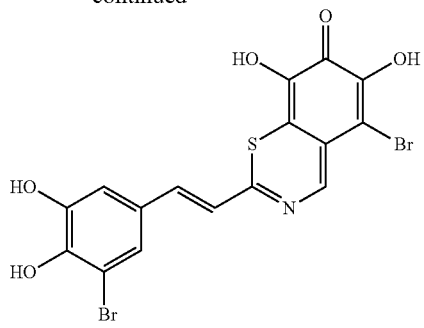

(7)

45 mg of compound no. 9 were dissolved in 10% ACN/DDW (2 ml). A mixture of 3 ml 0.2M H$_2$NaPO$_4$ and 12 ml 0.2M HNa$_2$PO$_4$ was added and the solution was stirred at room temperature for 1 hour. The reaction mixture was allowed to stand for at least 48 hours at 4° C. Following the incubation the product was centrifuged. The precipitate was washed with 0.1M MES (2-(N-morpholine)-ethane sulphonic acid) pH~5, then with DDW and finally was lyophilized to give compound 8 as a dark brown powder (45%). The purity of compound 7 was 70% as detected by HPLC and NMR. Cleaning of compound 7 was performed by preparative HPLC, yielding 4 mg of 8, 80% purity according to HPLC and NMR.

The assignment of the proton NMR signals of compound 7 is as follows $^1$H NMR (500 MHz, in MeOH, $^4$d): δ 7.75 (d, J=6, 1H), 7.35 (s, 1H), 7.1 (s, 1H), 7.05 (dd, J=16, 0.7 Hz 1H), Represents only H atoms in C—H bonds. MS (ESI): found (m/z) 487.86 (MH$^+$). calculated for C$_{16}$H$_9$Br$_2$NO$_5$S (MH$^+$) 486.86.

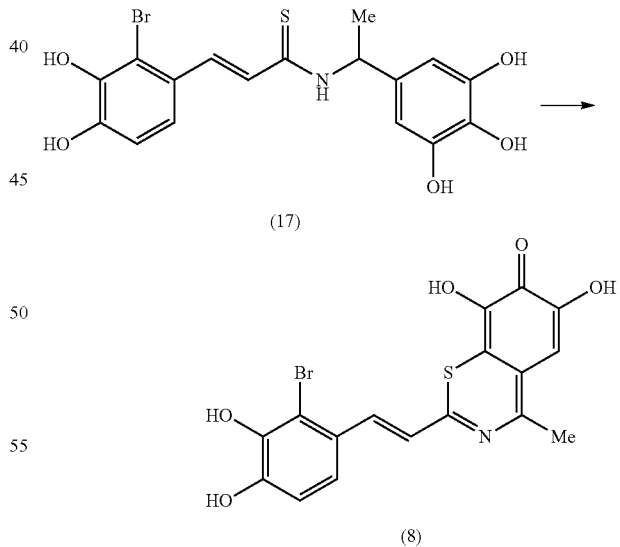

30 mg of precursor compound no. 17 are dissolved in 10% ACN/DDW (10 ml). A mixture of 5 ml 0.2M H$_2$KPO$_4$/HK$_2$PO$_4$ buffer, pH=7.4 is added and the solution stirred at room temperature for 1 hour, in which the solution changes its color from yellow to black. The reaction mixture is allowed to stay for at least 48 hours at 4° C. Following incubation the product is centrifuged. The precipitate is washed with 0.1M MES (2-(N-morpholine)-ethane sulphonic acid) pH~5, then with DDW and finally lyophilized to give compound 9 as a dark powder. The purity of compound 8 is detected by HPLC and NMR.

Other compounds of formula I may be prepared in the same manner from their corresponding precursors of formula II.

General procedures for the synthesis of compounds of formula II are further described in PCT international patent applications WO 2008/068751 and WO 2009/147682, the contents of each of which are incorporated by reference in their entirety. Some non-limiting examples are provided in the description below.

I. General Procedure for the Synthesis of Precursors of Formula V Wherein a Respectively are CN):

A. General Procedure for the Synthesis of the Following Intermediate Compound:

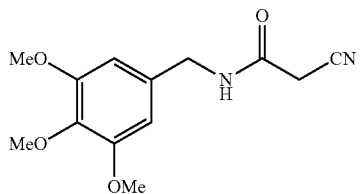 [SMILES: COc1cc(CNC(=O)CC#N)cc(OC)c1OC]

3,4,5-trimethoxybenzylamine (1.2 equiv) and methyl cyanoacetate (1 equiv) were stirred at room temperature until the precipitation of the product was observed. The product was collected by filtration, washed twice with ethanol, and dried under reduced pressure. The product was obtained as a white solid in 70-80% yield.

$^1$H NMR (300 MHz, in CDCl$_3$): δ 6.49 (s, 2H), 6.37 (bs, 1H), 4.40 (d, J=4.4 Hz, 2H), 3.86 (s, 6H), 3.84 (s, 3H), 3.43 (s, 2H). MS (ESI): found (m/z) 265.60. calculated for C$_{13}$H$_{17}$N$_2$O$_4$ (MH$^+$) 265.11.

B. General Procedure for the Synthesis of the Following Intermediate Compound:

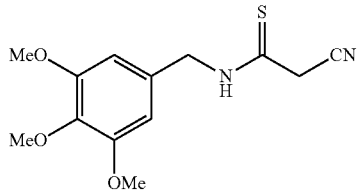

The amide produced in step (a) (1 equiv) and Lawesson's reagent (0.55 equiv) were heated in dry toluene (ca. 2 mL/mmol of the compound obtained in step (a)) under reflux for 3 hours (until TLC indicated the disappearance of the amide). The reaction mixture was cooled and evaporated under reduced pressure. The residue was purified by flash chromatography to yield a pale yellow solid in 50-60% yield.

$^1$H NMR (300 MHz, in Acetone-d$_6$): δ 9.20 (bs, 1H), 6.72 (s, 2H), 4.77 (d, J=5.2 Hz, 2H), 4.06 (s, 2H), 3.80 (s, 6H), 3.71 (s, 3H). MS (CI): found (m/z) 281.51. calculated for C$_{13}$H$_{17}$N$_2$O$_3$S (MH$^+$) 281.34.

C. General Procedure for the Synthesis of Compounds Denoted (i) Wherein X$^1$=F, (ii) Wherein X$^1$=Cl, (iii) Wherein X$^1$=Br, (iv) Wherein X$^1$=I, and (v) Wherein X$^1$=CF$_3$:

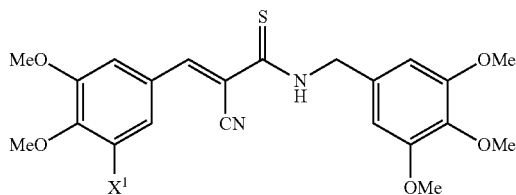

A catalytic amount of fl-alanine (0.2 equiv) was added to a solution of β-cyanothioamide (1 equiv) and an aldehyde ((1.2 equiv), commercially available except for 3,4-dimethoxy-5-(trifluoromethyl)benzaldehyde which was prepared according to Backstrom et al., *J. Med. Chem.* (1989), 32:841-846) in ethanol (ca. 20 mL/mmol of the compound obtained in step (b)). The solution was heated to 60° C. for 0.5 hour to overnight. The product was precipitated, collected by filtration, washed with H$_2$O, EtOH, and ether and then dried under reduced pressure to yield a pure yellow solid in 70% to quantitative yield.

For Compound (i):

$^1$H NMR (400 MHz, in Acetone-d$_6$): δ 9.60 (bs, 1H), 8.24 (s, 1H), 7.55 (m, 3H), 6.81 (s, 1H), 4.98 (s, 2H), 3.96 (s, 3H), 3.83 (s, 6H), 3.73 (s, 3H).

For Compound (ii):

$^1$H NMR (400 MHz, in CDCl$_3$): δ 8.69 (s, 1H), 7.99 (bt, 1H), 7.58 (d, J=2.0 Hz, 1H), 7.55 (d, J=2.0 Hz, 1H), 6.60 (s, 1H), 4.92 (d, J=5.2 Hz, 2H), 3.96 (s, 3H), 3.87 (s, 6H), 3.84 (s, 3H).

For Compound (iii):

$^1$H NMR (300 MHz, in Acetone-d$_6$): δ 9.62 (bt, 1H), 8.21 (s, 1H), 7.81 (s, 1H), 7.76 (s, 1H), 6.79 (s, 2H), 4.96 (m, 2H), 3.94 (s, 3H), 3.81 (s, 6H), 3.71 (s, 3H). MS (CI): found (m/z) 494.73. calculated for C$_{21}$H$_{22}$BrN$_2$O$_5$S (MH$^+$) 494.37.

For Compound (iv):

$^1$H NMR (400 MHz, in CDCl$_3$): δ 8.66 (s, 1H), 7.99 (bt, 1H), 7.86 (d, J=2.0 Hz, 1H), 7.72 (d, J=2.0 Hz, 1H), 6.60 (s, 2H), 4.93 (d, J=5.0 Hz, 2H), 3.97 (s, 3H), 3.88 (s, 6H), 3.86 (s, 3H). MS (CI): found (m/z) 540.67. calculated for C$_{21}$H$_{21}$N$_2$O$_5$S (M$^+$) 540.37.

For Compound (v):

$^1$H NMR (200 MHz, in CDCl$_3$): 8.75 (s, 1H), δ 8.22 (bt, 1H), 7.91 (d, J=2.0 Hz, 1H), 7.69 (d, J=2.0 Hz, 1H), 6.61 (s, 2H), 4.94 (d, J=5.0 Hz, 2H), 4.03 (s, 3H), 3.88 (s, 6H), 3.86 (s, 3H).

D. General Procedure for the Synthesis of Compounds of Formula V Wherein A=CN:

Boron tribromide (1.5 equiv excess for each hydroxyl group) was added to a cold solution of the protected product in anhydrous CH$_2$Cl$_2$ (ca. 20 mL/mmol of compounds of step (c)). The reaction mixture was allowed to warm to room temperature and stirred for 2-4 hours (until HPLC indicated the formation of the deprotected compound). The solution was cooled and then treated with dilute hydrochloric acid. The solution was extracted three times with ethyl acetate, the organic layer was dried over Na$_2$SO$_4$, filtered and the solvent was evaporated. The crude compound was recrystallized from water/ethanol to give yellow solid in 60-70% yield. This procedure can be used to prepare the precursor of compound 2, which is represented by the structure:

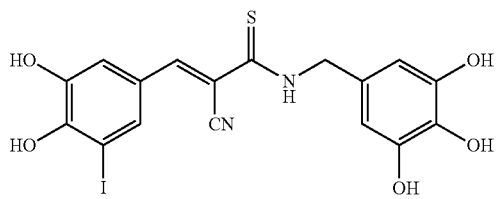 [SMILES: N#C/C(=C\c1cc(O)c(O)c(I)c1)C(=S)NCc1cc(O)c(O)c(O)c1]

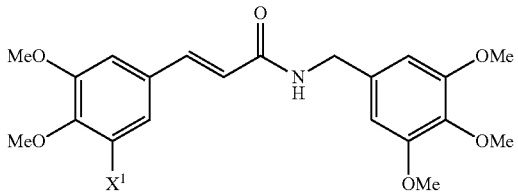

¹H NMR (200 MHz, in Acetone-$d_6$): δ 9.42 (bs, 1H), 8.24 (s, 1H), 7.91 (d, J=2.1 Hz, 1H), 7.64 (d, J=2.1 Hz, 1H), 6.47 (s, 2H), 4.79 (d, J=5.5 Hz, 2H). MS (ESI): found (m/z) 484.80. calculated for $C_{17}H_{14}IN_2O_5S$ (M⁺) 484.96. Anal. ($C_{17}H_{13}INO_5S$) C, H, N, I, S Other compounds of formula (B) can be prepared by similar methods.

II. General Procedure for the Synthesis of Precursors of Formula V Wherein A=H:

A. General Procedure for the Synthesis of the Following Compounds Denoted (vi) Wherein $X^1$=Br, (vii) Wherein $X^1$=I, and (viii) Wherein $X^1$=$CF_3$.

Compounds wherein X=H or compounds having additional substituents on the phenyl ring can be made in a similar manner.

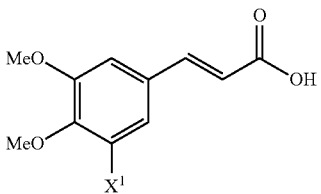

A catalytic amount of piperidine (0.2 equiv) was added to a solution of aldehyde ((1 equiv) commercially available except for 3,4-dimethoxy-5-(trifluoromethyl) benzaldehyde which was prepared according to Backstrom et al., *J. Med. Chem.* (1989), 32:841-846) and malonic acid (1.5 equiv) in pyridine. The reaction mixture was heated to 120° C. for 6 h. The solution was cooled to room temperature and concentrated HCl was added dropwise to pH<3. The white solid was collected by filtration, washed with water and dried under reduced pressure.

For Compound (vi):

¹H NMR (300 MHz, in CDCl₃): δ 7.65 (d, J=15.9 Hz), 7.35 (d, J=2.1 Hz, 1H), 7.01 (d, J=2.1 Hz, 1H), 6.35 (d, J=15.9 Hz, 1H), 3.90 (s, 3H), 3.88 (s, 3H).

For Compound (vii):

¹H NMR (400 MHz, in CDCl₃): δ 7.64 (d, J=2.0 Hz, 1H), 7.56 (d, J=2.0 Hz), 7.04 (d, J=2.0 Hz, 1H), 6.35 (d, J=16.0 Hz, 1H), 3.92 (s, 3H), 3.88 (s, 3H).

For Compound (viii):

¹H NMR (400 MHz, in CDCl₃): δ 7.63 (d, J=16 Hz), 7.61 (s, 1H), 7.43 (s, 1H), 6.50 (d, J=16 Hz, 1H), 3.90 (s, 3H), 3.88 (s, 3H).

B. General Procedure for the Synthesis of the Following Compounds Denoted (ix) Wherein $X^1$=Br, (x) Wherein $X^1$=I, and (xi) Wherein $X^1$=$CF_3$:

The solution of compounds (vi-viii, 1 equiv) in oxalyl chloride (4 equiv) was stirred for 1-2 hours at room temperature. The excess of oxalyl chloride was distilled off and the mixture was evaporated to dryness. The residue was dissolved in $CH_2Cl_2$ and added drop wise to a solution of an amine (0.85 equiv) and $Et_3N$ (4 equiv) in $CH_2Cl_2$. the reaction mixture was stirred at room temperature for 0.5-1 hour (until TLC indicated the disappearance of the amine). The solvent was evaporated under reduced pressure and the residual oil was purified by flash chromatography.

For Compound (ix):

¹H NMR (300 MHz, in CDCl₃): δ 7.52 (d, J=15.8 Hz, 1H), 7.29 (s, 1H), 6.92 (s, 1H), 6.50 (s, 2H), 6.37 (d, J=15.8 Hz, 1H), 6.23 (bt, 1H), 4.46 (d, J=5.7 Hz, 2H), 3.81-3.85 (s, 15H). MS (ESI): found (m/z) 467.87. calculated for $C_{21}H_{25}BrNO_6$ (MH⁺) 466.32.

For Compound (x):

¹H NMR (400 MHz, in CDCl₃): δ 7.51 (d, J=2.0 Hz, 1H), 7.50 (d, J=15.6 Hz), 6.96 (d, J=2.0 Hz, 1H), 6.51 (s, 2H), 6.35 (d, J=15.6 Hz, 1H), 6.10 (bt, J=5.2 Hz, 1H), 4.47 (d, J=5.2 Hz, 2H), 3.85 (s, 3H), 3.84 (s, 3H) 3.82 (s, 6H), 3.81 (s, 3H).

For Compound (xi):

¹H NMR (300 MHz, in CDCl₃): δ 7.52 (d, J=15.8 Hz, 1H), 7.29 (s, 1H), 6.92 (s, 1H), 6.50 (s, 2H), 6.37 (d, J=15.8 Hz, 1H), 6.23 (bt, 1H), 4.46 (d, J=5.7 Hz, 2H), 3.81-3.85 (s, 15H). MS (ESI): found (m/z) 467.87. calculated for $C_{21}H_{25}BrNO_6$ (MH⁺) 466.32.

C. General Procedure for the Synthesis of the Following Compounds Denoted (xii) Wherein $X^1$=Br, (xiii) Wherein $X^1$=I, and (xiv) Wherein $X^1$=$CF_3$:

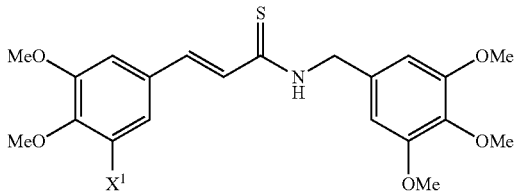

An amide (1 equiv) and Lawesson's reagent (0.55 equiv) were refluxed in toluene for 3 hours (until TLC indicated the disappearance of the amide). The reaction mixture was cooled and evaporated under reduced pressure. The residue was purified by flash chromatography to yield a pale yellow solid in 50-60% yield.

For Compound xii:

¹H NMR (300 MHz, in CDCl₃): δ 7.75 (d, J=15.3 Hz, 1H), 7.41 (d, J=2.1 Hz, 1H), 7.29 (d, J=2.1 Hz, 1H), 7.16 (d, J=15.3 Hz, 1H), 6.76 (s, 2H), 4.90 (m, 2H), 3.94 (s, 3H), 3.83 (s, 3H), 3.77 (s, 6H), 3.70 (s, 3H). MS (ESI): found (m/z) 483.87. calculated for $C_{21}H_{25}BrNO_5S$ (MH⁺) 483.38.

For Compound (xiii):

¹H NMR (400 MHz, in CDCl₃): δ 7.71 (d, J=15.2 Hz, 1H), 7.6 (bt, 1H), 7.56 (d, J=1.8 Hz, 1H), 7.01 (d, J=1.8 Hz,

1H), 6.78 (d, J=15.2 Hz, 1H), 6.55 (s, 2H), 4.86 (d, J=5.0 Hz, 2H), 3.86 (s, 3H), 3.84 (s, 3H), 3.83 (s, 6H), 3.82 (s, 3H).

For Compound (xiv):

$^1$H NMR (300 MHz, in CDCl$_3$): δ 7.75 (d, J=15.3 Hz, 1H), 7.41 (d, J=2.1 Hz, 1H), 7.29 (d, J=2.1 Hz, 1H), 7.16 (d, J=15.3 Hz, 1H), 6.76 (s, 2H), 4.90 (m, 2H), 3.94 (s, 3H), 3.83 (s, 3H), 3.77 (s, 6H), 3.70 (s, 3H). MS (ESI): found (m/z) 483.87. calculated for C$_{21}$H$_{25}$BrNO$_5$S (MH$^+$) 483.38.

D. General Procedure for the Synthesis Compounds of Formula V Wherein A=H:

Compounds of formula V wherein A=H may be prepared in the same manner as set forth in step (I)(D) described above for the corresponding compounds of formula II wherein A=CN.

This procedure can be used to prepare the precursors of compounds 2-8, which are represented by the structures

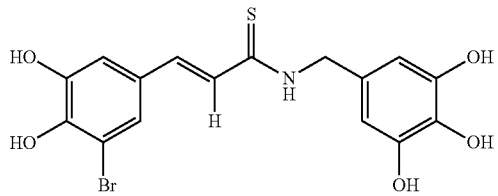 [SMILES: Oc1cc(CNC(=S)/C=C/c2cc(O)c(O)c(Br)c2)cc(O)c1O]

Compound No. 29 is the Precursor of Compounds 2 and 5

$^1$H NMR (400 MHz, in Acetone-d$_6$): δ 9.16 (bs, 1H), 7.69 (d, J=15.4 Hz, 1H), 7.31 (d, J=1.9 Hz, 1H), 7.09 (d, J=1.9 Hz, 1H), 7.06 (d, J=15.4 Hz, 1H), 6.44 (s, 2H), 4.76 (d, J=5.7 Hz, 2H). MS (ESI): found (m/z) 411.93. calculated for C$_{16}$H$_{15}$BrNO$_5$S (MH$^+$) 411.97. Anal. (C$_{16}$H$_{14}$BrNO$_5$S) C, H, N, Br, S

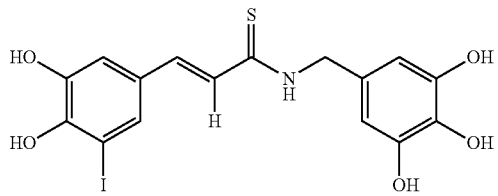 [SMILES: Oc1cc(CNC(=S)/C=C/c2cc(O)c(O)c(I)c2)cc(O)c1O]

Compound No. 30 is the Precursor of Compound 3

$^1$H NMR (400 MHz, in Acetone-d$_6$): δ 9.2 (bs, 1H), 7.67 (d, J=15.2 Hz, 1H), 7.51 (d, J=2.0 Hz, 1H), 7.12 (d, J=2.0 Hz, 1H), 7.02 (d, J=15.2 Hz, 1H), 6.44 (s, 2H), 4.76 (d, J=5.2 Hz, 2H). MS (ESI): found (m/z) 460.13. calculated for C$_{16}$H$_{15}$INO$_5$S (MH$^+$) 460.26. Anal. (C$_{16}$H$_{14}$INO$_5$S) C, H, N, I, S

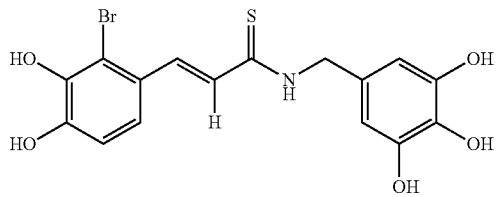 [SMILES: Oc1cc(CNC(=S)/C=C/c2ccc(O)c(O)c2Br)cc(O)c1O]

Compound No. 10 is the Precursor of Compound 4

$^1$H NMR (300 MHz, CDCl$_3$): δ 4.77 (d, 2H, J=5.2 Hz, CH$_2$N), 6.43 (s, 2H, aromatic), 6.86 (d, 1H, J=8.4 Hz, aromatic), 7.01 (d, 1H, J=15.2 Hz, alkene), 7.16 (d, 1H, J=8.4 Hz, aromatic), 8.27 (d, 1H, J=15.2 Hz, alkene), 8.99 (br.s., 1H, NH). Anal. (C$_{16}$H$_{14}$BrNO$_5$S) C, H, N, Br, S

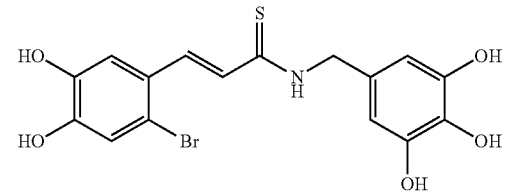

Compound No. 11 is the Precursor of Compound 6

$^1$H NMR (400 MHz, CDCl$_3$): δ 8.20 (d, J=15.2 Hz, 1H, Ar—C$\underline{H}$=CH), 7.23 (s, 1H, aromatic CH), 7.12 (s, 1H, aromatic CH), 6.99 (d, J=15.2 Hz, 1H, 1H, Ar—CH=C$\underline{H}$), 6.46 (s, 2H, aromatic CH), 4.79 (d, J=5.6 Hz, 2H, CH$_2$N).

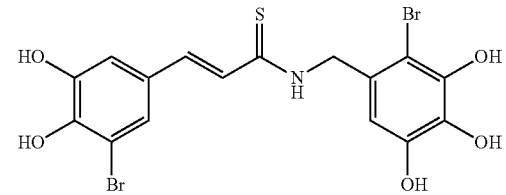 [SMILES: Oc1cc(/C=C/C(=S)NCc2cc(O)c(O)c(O)c2Br)cc(Br)c1O]

Compound No. 9 is the Precursor of Compound 7

δ 9.10 (bt, 1H), 7.70 (d, J=15.2 Hz, 1H), 7.32 (d, J=2 Hz, 1H), 7.12 (d, J=2 Hz, 1H), 7.08 (d, J=15.2 Hz, 1H), 6.60 (s, 1H), 4.91 (d, J=4.8 Hz, 2H).

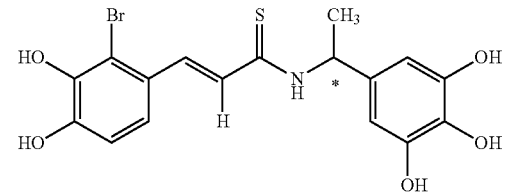 [SMILES: CC(NC(=S)/C=C/c1ccc(O)c(O)c1Br)c1cc(O)c(O)c(O)c1]

Compound No. 17 is the Precursor of Compound 8

$^1$H NMR (400 MHz, in Acetone-d$_6$): δ 1.54 (d, 3H, J=5.2 Hz, CH$_3$), 5.84 (q, 1H, J=7 Hz, CH), 6.49 (s, 2H, aromatic), 6.89 (d, 1H, J=8.8 Hz, aromatic), 7.0 (d, 1H, J=15.2 Hz, alkene), 7.17 (d, 1H, J=8.4 Hz, aromatic), 8.21 (d, 1H, J=12.8 Hz, alkene), 9.18 (d., 1H, NH, J=8).

It is noted that all enantiomers and diastereomers of the compounds of the present invention and their precursors are included within the scope of the invention. For example, the compound of formula 9 is chiral. The present invention contemplates the use of the R and S enantiomers, mixtures thereof in any ratio, as well as the racemic mixtures.

Other compounds of formula (V) can be prepared by similar methods.

Example 2: Materials and Methods

Worm and RNAi Strains

CL2006 (Link, 1995), CL2070, TJ356 and $N_2$ worm strains were obtained from the *Caenorhabditis* Genetics Center (Minneapolis, Minn.). The worms were grown at 20° C. To reduce gene expression, we used previously described (Dillin et al., 2002) bacterial strains expressing dsRNA towards: EV (pAD12), daf-2 (pAD48), daf-16 (pAD43). hsf-1 dsRNA expressing bacterial strain was from genomic RNAi library (J. Ahringer). Each RNAi bacterial colony was grown at 37° C. in LB with 100 μg mL) 1 carbenicillin, and then seeded onto NG-carbenicillin plates supplemented with 100 mM Isopropyl 13-D-1-thiogalactopyranoside (IPTG).

DAF-16 Localization Assay

Synchronized TJ356 worms were grown on the EV control bacteria. At the indicated ages (days 1 of adulthood), 25 worms were transferred onto daf-2 RNAi bacteria for the indicated time (6 h). The worms were washed twice with M9, snap froze in liquid nitrogen and nuclei were labeled for 30 min using 4¢,6-diamidino-2-phenylindole (DAPI) [200 ng mL); (Molecular Probes), Invitrogen, Carlsbad, Calif., USA]. DAPI and GFP signals were visualized using a fluorescent microscope (Leica DM6000 B; Leica, Wetzlar, Germany).

Paralysis Assay

Synchronous CL2006 worm populations were grown on NG plates containing 100 μg/ml ampicillin, spotted with *E. coli* cultures expressing either dsRNA towards daf-2 or harboring the empty vector control. On the first and second days of adulthood, the worms were soaked for three hours in buffer containing either 300 μM of the indicated drug (treatment group) or identical volume of the chemical vehicle (control group). 120 worms were placed on 10 plates (12 animals per plate). The plates were divided randomly to 5 sets (2 plates, 24 worms per set). The worms were tested every day for paralysis by tapping their noses with a platinum wire. Worms that moved their noses but failed to move their bodies were scored as "paralyzed" and removed from the plates. After scoring additional 25 μl of the drug or vehicle were added to each plate daily. To avoid scoring old animals as paralyzed, paralysis assays were terminated at day 12 of adulthood.

Lifespan Assay

Synchronized CF512 worm eggs were placed on master NG-carbenicillin plates seeded with control bacteria (EV) or with RNAi bacterial strain (daf-2 RNAi control) and supplemented with 100 mM IPTG. The eggs were let hatch and the larvae developed at 20° C. until day 1 of adulthood. The worms were soaked in PBS buffer containing either 300 m of the indicated drug or identical volume of the chemical vehicle (control) for three hours every day from day 1 to day 5 of adulthood (the lifespan regulatory time window) and were transferred onto small NG-carbenicillin plates (12 animals per plate). Adult worms were transferred onto freshly seeded plates every four days. Worms that failed to move their noses when tapped twice with a platinum wire were scored as dead. Worms were scored daily. Lifespan analyses were conducted at 20° C.

Figure 1A:
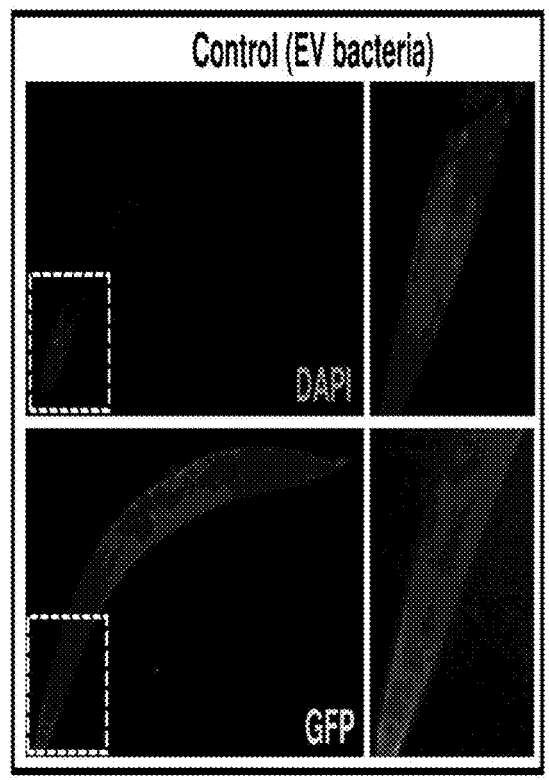
FIG. 1: A compound according to some embodiments of the invention (i.e. compound no. 29) promotes DAF-16 nuclear localization. DAF-16::GFP expressing worms (strain TJ356) were grown on control bacteria (EV) to day 1 of adulthood (A) and then placed on daf-2-RNAi bacteria (B) or 300 μM of compound no. 29 (C). After 6 hours of incubation, the worms were fixed and stained with DAPI. Co-localization of the DAPI and GFP signals (arrows) confirmed the nuclear localization of DAF-16 in day 1 old worms that were treated with either daf-2-RNAi or compound no. 29.
Figure 1B:
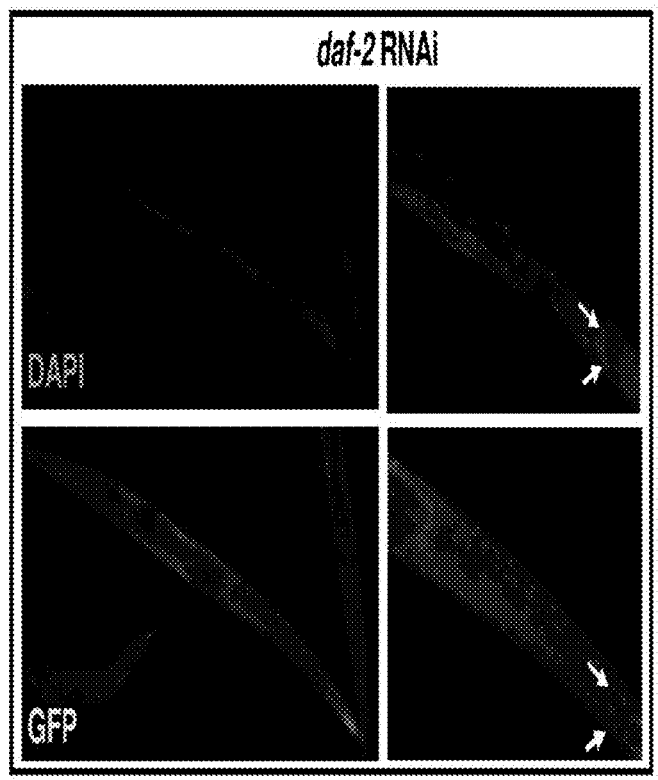
Figure 1C:
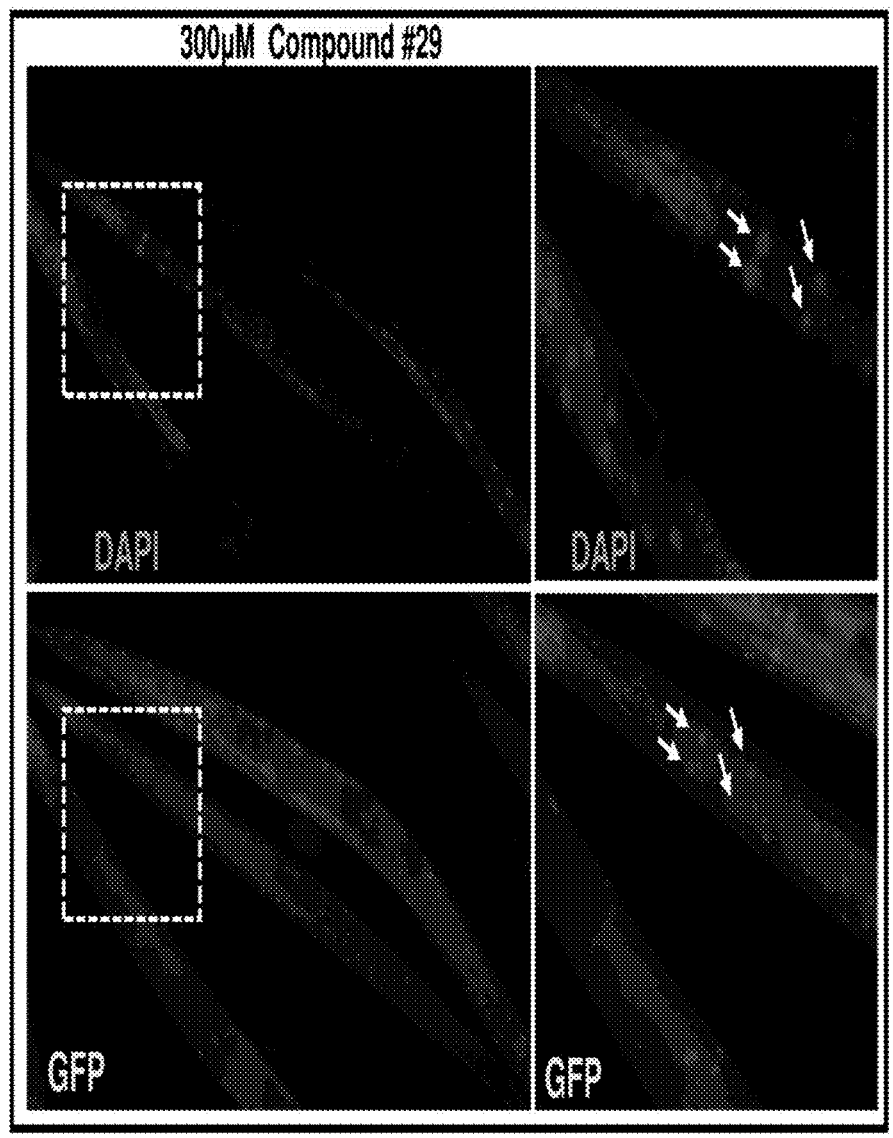

Compound No. 29 Promotes DAF-16 Nuclear Localization:

TJ356 worms (DAF-16 tagged worms) were used to test whether IIS reduction by compound no. 29 drives DAF-16 into the nucleus. The worms were let hatched and develop on control bacteria harboring an empty vector (EV) (FIG. 1A) or on daf-2 RNAi bacteria (FIG. 1B). One group of EV bacteria fed animals was soaked for 6 hours in buffer containing 300 μM compound no. 29 (FIG. 1C) while another EV-grown group was soaked in buffer containing the chemical vehicle. The worms were then fixed and stained with DAPI. Co-localization of the DAPI and GFP signals (arrows) confirmed the nuclear localization of DAF-16 in worms that were fed compound no. 29 as well as daf-2 RNAi.

Figure 2:
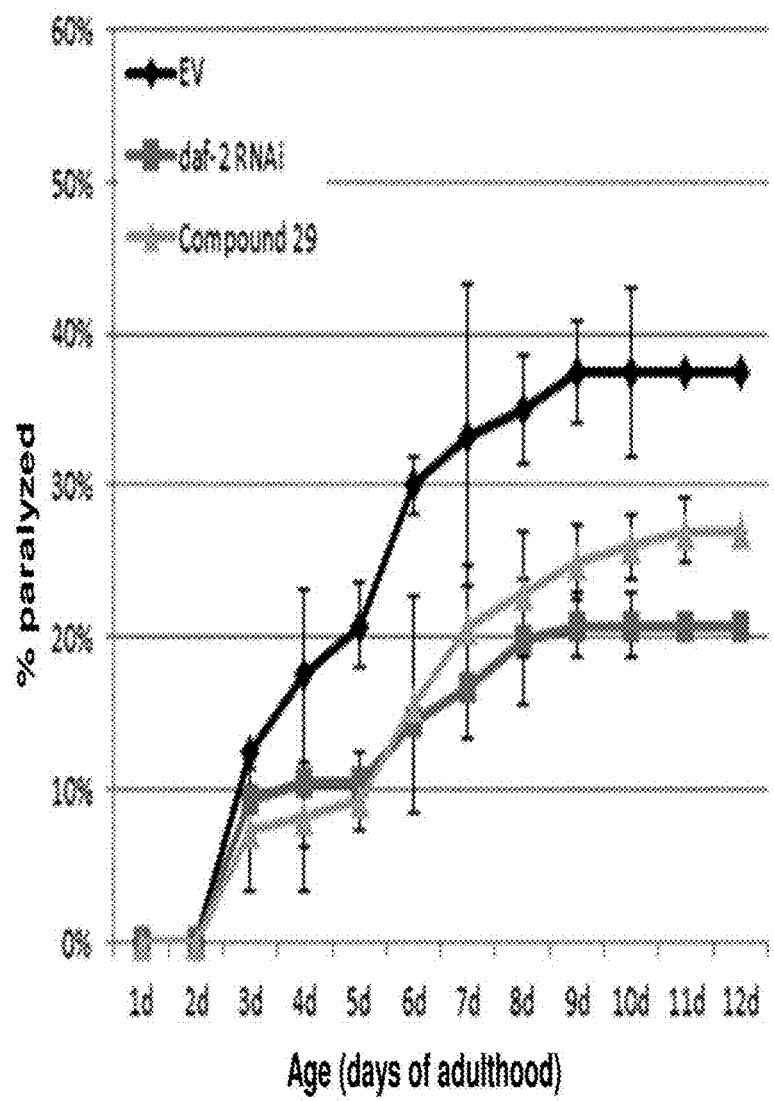
FIG. 2: Compound 29 according to some embodiments of the invention protects worms from Aβ toxicity. Aβ worms (strain CL2006) at days 1 and 2 of adulthood were soaked in a buffer containing compound no. 29. At day 3 of adulthood the worms treated with compound no. 29 were transferred onto empty vector (EV) bacteria and were supplemented daily with 25 μl of 300 μM of compound 29. Paralyzed worms were scored daily. Control experiments include: 1) untreated control: worms soaked with buffer only and 2) daf-2 RNAi treated control worms which were grown throughout the experiment on daf-2 RNAi expressing bacteria.

The IGF-1R Inhibitors, Compound No. 29 Protects Worms from Aβ Toxicity:

CL2006 worms at days 1 and 2 of adulthood (according to the 'paralysis assay' protocol above) were soaked for 3 hours a day in a buffer containing either compound no. 29 in solution (300 μM) (worms soaked with buffer only with no active compound, served as an untreated control).daf-2 RNAi treated control worms were grown throughout the experiment on daf-2 RNAi expressing bacteria. At day 3 of adulthood the worms were transferred onto EV bacteria or left on daf-2 RNAi bacteria (daf-2 RNAi control group). The plates of the treated groups were supplemented daily with 25 μl of 300 μM of compound no. 29 (FIG. 2). Paralyzed worms were scored daily. The results show that the paralysis rates within the treated groups increased in reduced rates compared to the untreated control.

Figure 3:
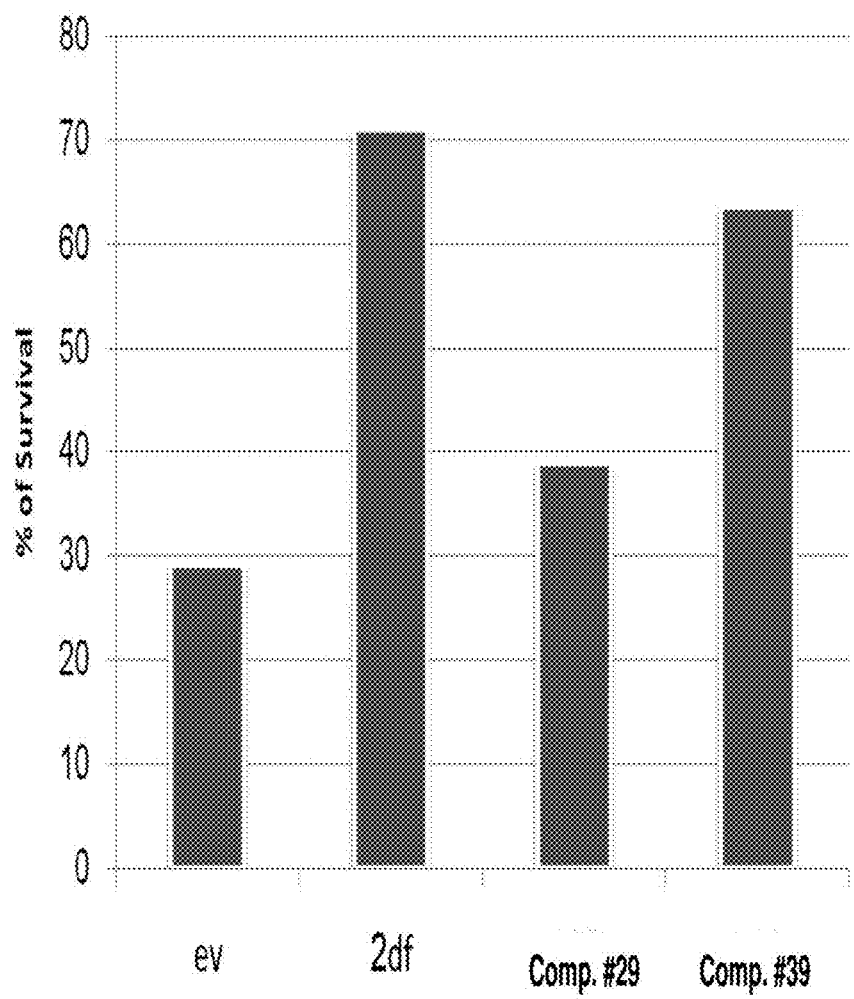
FIG. 3: Compounds according to some embodiments of the invention (i.e. compounds 29 and 39) elevate stress resistance of CF512 worms. At day 1 adult CF512 worms were either treated with daf-2 RNAi, compound 29 or compound no 39 (in solution (300 μM)) 3 hours at day 1. The worms were placed on plates seeded with EV bacteria and exposed to 35° C. for 15 hours, survival was measured.

Compound No. 39 Elevates Stress Resistance of CF512 Worms:

Day 1 adult CF512 worms were either treated with daf-2 RNAi, compound no. 29 or compound no. 39 (in solution (300 μM)) for 3 hours at day 1. The worms were placed on plates seeded with EV bacteria and exposed to 35° C. for 15 hours and survival rates were scored by counting the surviving worms. The results of a representative experiment (three repeats were performed) is presented on FIG. 3.

Example 3: Effects of Compound 39 on IGF1 Signaling in Cultured Human Cells, Expression of IIS-Regulated Genes in Worm, Protoxocity in Nematodes, and PrP Aggregation in Cyclosporine-A Treated Cells Methods Worm and RNAi Strains All worm strains were obtained from the *Caenorhabditis* Genetics Center (CGC, Minneapolis, Minn.). The worms were grown at 20° C. CF512 (fer-15(b26)II; fem-1(hc17)IV) worms are heat-sensitive sterile that were routinely grown at 15° C. To avoid progeny, eggs of CF512 worms were incubated at 20° C. for 16 h, larvae transferred to 25° C. for 48 h and back to 20° C. until harvested. To reduce gene expression we used previously described (Dillin et al, 2002) bacterial strains expressing dsRNA: empty vector (pAD12) and daf-2 (pAD48). Each RNAi bacteria colony was grown at 37° C. in LB medium with 100 μg/ml Ampicillin, and then seeded onto Nematode growth (NG)-ampicillin plates supplemented with 100 mM Isopropyl 3-D-1-thiogalactopyranoside (IPTG).

Protein Blotting and Analysis

Human melanoma A375 cells were obtained from the ATCC and cultured in RPMI with 10% fetal calf serum (FCS) and antibiotics. A375 cells were grown in 6-well plates, treated as indicated in a serum-starved medium, stimulated with 50 ng/ml IGF1 for 5 min, and lysed with boiling sample buffer (10% glycerol, 50 mM Tris-HCl, pH6.8, 3% SDS, and 5% 2-mercaptoethanol). Western blot analysis was as described previously (Mizrachy-Schwartz et al, 2011). Equal amounts of protein per sample were subjected to SDS-PAGE and immunoblotted with anti-p(T308) PKB (cat#9275), anti-p(S473) PKB (cat#9271), anti-p (Y1131) IGF1Rβ/(Y1146) IR (cat#3021) and anti-pS(636/639)IRS1 (cat#2388) antibodies (Cell Signaling Technology (Beverly, Mass.)), and anti-p(Y612)IRS1 (cat#44-816G) antibody (Biosource), to detect the phosphorylation levels (designated p in figures) of the indicated proteins. Following stripping the membranes were immunoblotted with anti-IRS1 (cat#ab40777) and anti-IRS2 (cat#ab52606) antibodies (Abcam (Cambridge, UK)), anti-PKB1/2 (cat#sc8312) and anti-IGF1R(3 (cat#sc731) antibodies (Santa Cruz Biotechnology (Santa Cruz, Calif.) and anti-β-Catenin (cat#610154, BD Transduction Laboratories) as a control protein, to visualize the total amount of the indicated proteins. The antibodies against pS(636/639)IRS1 and pY(612) IRS1 cross react with the corresponding phosphorylated forms of IRS2, therefore marked as pS-IRS1/2 and pY-IRS1/2 in FIG. 1 (Cancer Research 2013).

Worms were grown on RNAi bacterial strains and treated with compound no. 39 as indicated. Compound no. 39 was diluted in 20% 2-hydroxypropyl-j-cyclodextrin (2-HP-3-CD) (Sigma, St. Louis, Mo.) and diluted to the indicated concentration in the buffer reaction in all worm experiments. The vehicle, 20% 2-HP-β-CD, was diluted the same in the control systems. The worms were resuspended in cold PBS, transferred to a 2 ml tissue grinder (885482, Kontes, Vineland, N.J.) and homogenized. Homogenates were spun in a desktop microfuge (3000 rpm, 3 min) at 4° C. Total protein concentrations in the supernatants were measured using Bradford reagent (Biorad #500-0006). SDS-Loading dye was added to the protein lysates and boiled for 10 min at 95° C. After separation on a PAA gel, proteins were transferred onto a PVDF membrane and blotted. GFP was detected with anti-GFP antibody (Cell Signaling, Danvers, Mass. cat #2956). All antibodies were labeled with HRP-conjugated secondary antibody and developed using an ECL system. Chemiluminescence was detected using a Luminescent Image Analyzer (LASS-3000-Fujifilm, Tokyo, Japan). For fluorescent detection of polyQ40-YFP aggregates native loading dye (2×: 0.125M Tris pH6.8, 20% Glycerol, 0.02% Bromophenolblue) was added to an equal amount of worm homogenates and the samples were loaded onto a 1% native agarose gel, dissolved in running buffer (25 mM Tris pH8.3, 0.19M Glycine) and run at 50V for 20 h. Images were taken using the LASS-3000 visualization system and band intensities were measured using ImageJ software.

High-Speed PrP Sedimentation Assay

Cells were washed with PBS and TX-DOC lysis buffer (0.5% Triton X-100, 0.25% Na-deoxycholate, 150 mM NaCl, 10 mM Tris HCl pH 7.5, 10 mM EDTA) containing protease inhibitor cocktail (Calbiochem, SD, Calif. USA cat#534133)) was added. Lysates were centrifuged for 1 min at 6000 rpm at 4° C. The post nuclear supernant (PDS) was used for the following steps. Protein concentrations were adjusted using BCA protein measurement kit (Thermo Scientific), the samples were supplemented with Sarkosyl (final 1%) and incubated for 30 min on ice with gentle mixing. PDS were ultra-centrifuged for 1 h at 4° C. at 45000 rpm (gav=109,000). The supernatant and pellet were analyzed by WB using a PrP antibody (clone 3F4 (1:2000), Millipore, Billerica, Mass. USA).

RNA Isolation and Quantitative Real Time PCR

Total RNA was isolated from synchronized populations of approximately 15,000 sterile worms grown at 20° C. for the indicated age using QIAzol reagent (Cat #79306 QIAGEN, Hilden Germany) and purified by RNeasy lipid tissue kit (QIAGEN #74104). cDNA was created using iScript advanced cDNA Synthesis Kit (BIO-RAD, #170-8891). For quantitative PCR reactions, dilutions of 1:10 were used. Real-time qPCR experiments were performed as described in the manual using CFX cycler (Biorad, Hercules, Calif. USA) and EvaGreen supermix (Biorad, #172-5204). Quantification was normalized to control levels of act-1 cDNA.

```
sod-3 primer set: Forward:
CTA AGG ATG GTG GAG AAC CTT CA

Reverse:
CGC GCT AAA TAG TGT CCA TCA G hsp-12.6 primer set: Forward:
TTCCAGTGATGGCTGACG;

Reverse:
GGCTTCTAGGCCTACTTCG hsp-70 primer set: Forward:
GGTTGGGGGATCAACTCG

Reverse:
CACCAAAGGCTACTGCTTCG.

hsp-16.1: Forward: Reverse:

gst-4: Forward:
CCCATTTTACAAGTCGATGG

Reverse:
CTTCCTCTGCAGTTTTTCCA gst-10: Forward:
GTCTACCACGTTTTGGATGC

Reverse:
ACTTTGTCGGCCTTTCTCTT act-1 primer set: Forward:
GAGCACGGTATCGTCACCAA

Reverse:
TGTGATGCCAGATCTTCTCCAT.
```

Heat and UV Stress Assays

Synchronous eggs of CF512 worms were placed on NG plates containing 100 μg/mL ampicillin, seeded with the indicated bacterial strain (EV or daf-2 RNAi) and supplemented with 100 mM IPTG. The worms were incubated at 20° C. until day 1 of adulthood and treated as indicated. Total of 120 worms were transferred onto fresh plates (12 animals per plate) spotted with bacteria. The plates were exposed to 35° C. for 15 hours and vitality was recorded by tapping each animal's nose with a platinum wire. Worms that did not respond were scored dead. To evaluate resistance to UV radiation eggs of CF512 worms were placed on plates and treated as described above. Day 1 adult, EV-grown worms were either treated with compound no. 39 or soaked in the chemical vehicle for 3 hours and exposed to 800 j/cm² UV for 20 seconds (add type of UV radiator in here) along with worms that were treated with daf-2 RNAi. The worms were transferred onto plates seeded with bacteria and compound no. 39 or the vehicle was added to the plates daily after scoring the numbers of viable worms.

Lifespan Analysis

Synchronized worm eggs were placed on master NG-ampicillin plates seeded with the indicated RNAi bacterial strain and supplemented with 100 mM IPTG. The eggs were incubated at 20° C. until transferred onto small NG-ampicillin plates (10 animals per plate) at the indicated ages. Adult worms were transferred onto freshly seeded plates every four days. Worms that failed to move their noses when tapped twice with a platinum wire were scored as dead. Dead worms were scored daily. Lifespan analyses were conducted at 20° C.

Paralysis and Motility Assays

Synchronous CL2006 worm populations were grown on NG plates containing 100 μg/ml ampicillin and spotted with EV or daf-2 RNAi bacteria. At days 1 and 2 of adulthood the worms were either treated for three hours with 600 μM compound no. 39 or with the chemical vehicle in solution. 120 worms were placed on 10 plates (12 animals per plate) and the plates were divided randomly to 5 sets (2 plates, 24 worms per set). compound no. 39 or the chemical vehicle was supplemented daily to the plates after testing the rate of paralysis by tapping their noses with a platinum wire. Worms that moved their noses but failed to move their bodies were scored as "paralyzed" and removed from the plates. Paralysis assays were terminated at day 12 of adulthood.

To test the rates of motility, polyQ35-YFP worms were treated daily with either the chemical vehicle or with 600 μM compound no. 39 from day 1 to day 11 of adulthood. As control groups we used polyQ35-YFP that were grown on daf-2 RNAi bacteria and polyQ0-YFP animals that were grown on EV bacteria and supplemented daily with the chemical vehicle. At days 1 and 11 of adulthood 56 worms of each treatment were transferred onto 8 plates (7 animals/plate) and video-taped by an automated microscope system (30 frames per minute for 1 minute). Crawling speeds were calculated by a worm tracking software.

Worm and Cell Immunofluorescence

Immunofluorescence was performed as described previously (Cohen et al, 2006). Briefly, worms were pre-fixed with 4% paraformaldehyde in MRWB (80 mM KCl, 20 mM NaCl, 10 mM EGTA, 5 mM Spermidine, 50% Methanol), froze on dry ice, incubated on ice for 1 h and washed once in M9 buffer and twice more in Tris-Triton buffer (100 mM Tris pH7.4, 1% TX-100, 1 mM EDTA). The worms were then incubated for 2 h at 37° C. in Tris-Triton buffer supplemented with 1% 1-Mercaptoethanol, washed in $BO_3$ buffer (25 mM $H_3BO_3$, 12.5 mM NaOH) and incubated for 15 min in $BO_3$ buffer supplemented with 10 mM DTT. Next, the worms were washed and incubated in $BO_3$ buffer supplemented with 0.3% $H_2O_2$ for 15 min (RT) and washed with $BO_3$ buffer and with blocking buffer (PBSX1, 1% BSA, 0.5% TX-100, 1 mM EDTA). Aβ staining was performed overnight at 4° C. using 4G8 antibody, washed in blocking buffer and stained for 30 min (RT) with a secondary antibody conjugated to Rhodamin.

To detect PrP CHO-M cells (expressing PrP MHM2) were grown on a chamber slide (Lab-Tek). The cells were treated as indicated, washed with PBS and fixed with 3.7% formaldehyde solution for 30 min (RT). The cells were than washed with 1% $NH_4Cl$ (in PBS), permeabilized using 0.1% Triton X-100 in PBS, blocked with 2% BSA in PBS for 45 min and incubated over night with PrP antibody (clone 3F4 (1:200), Millipore, Billerica, Mass. USA). The cells were washed with PBS and incubated in the CY5-labeled secondary antibody (Jackson ImmunoResearch West Grove, Pa., USA) for 1 h (RT) followed by washing (PBS) and mounting with Vectashield (Vector Laboratories, Burlingame, Calif. USA).

Results

Compound 39 Effectively Inhibits the IGF1 Signaling Pathway in Mammalian Cells

To assess the efficiency of Compound (FIG. 4A) as an inhibitor of the IGF1 signaling cascade and to explore its mechanism of action the human melanoma cell line, A375, was used. The cells were treated with increasing concentrations of compound no. 39 for either 4 hours (FIG. 4B, short exposure) or 19 hours (FIG. 4C, long exposure), and the IGF1 signaling cascade was activated by the supplementation of IGF1 to the cell media five minutes prior to lysis. Western blot (WB) analysis showed that IGF1 induced the auto-phosphorylation of IGF1R (pIGF1R, FIGS. 4B and C, lane 2), and that this phosphorylation was largely abolished when 6 μM of compound no. 39 was added to the cell media (pIGF1R, FIG. 4B lane 5 and 1C lane 6). Since upon activation IGF1R undergoes auto-phosphorylation (Favelyukis et al, 2001) this observation indicates that this compound reduces the activation of IGF1R.

The phosphorylation of the Insulin Receptor Substrates (IRS) 1 and 2, direct substrates of IGF1R and major mediators of its signals, on serine residues, are known to block IGF1 signaling by decoupling these molecules from the receptor and directing them for degradation. This is a well-defined negative feedback loop that enables cells to shut off the IGF1 signaling cascade (Boura-Halfon & Zick, 2009). Compound no. 39 and related compounds uniquely induce Ser-phosphorylation and degradation of IRS1 and IRS2 to gain a long-lasting inhibition of the IGF1 signaling. As shown herein, both IRS1 and IRS2 undergo massive phosphorylation on serine residues after a short exposure to compound no. 39, as detected by specific antibodies (pS-IRS1/2, FIG. 4B lanes 4-5), and by the upshift of these proteins in the gels (IRS2 and IRS1, FIG. 4B lanes 4-5). A subsequent elimination of IRS1 and IRS2 was revealed (IRS1 and IRS2, FIG. 4C, lanes 4-6). The results indicate that compound no. 39 uniquely triggers the IRS1/2 Serine-phosphorylation and degradation loop to gain a long-lasting blockage of the IGF1 signaling pathway.

Figure 4:
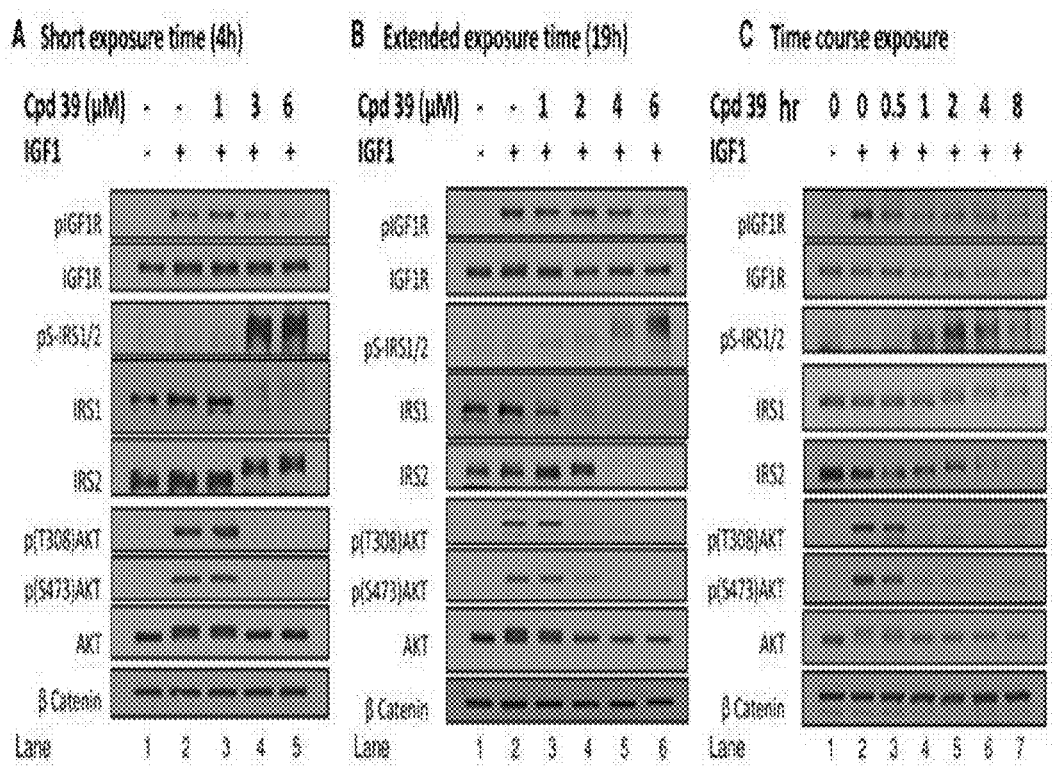
FIG. 4: Compound no. 39 inhibits the IGF1R to AKT signaling pathway in human melanoma cells. A-B. Compound 39 treatment reduces the IGF1-induced auto-phosphorylation of the IGF1R, induces inhibitory Ser-phosphorylation and subsequent elimination of the Insulin Receptor Substrate 1 (IRS1) and 2 (IRS2), and prevents the IGF1-induced activation of AKT in A375 human melanoma cells, following short (A) and long (B) exposures. C. Temporal analysis of the effects of Compound 39 on components of the IGF pathway indicates that the compound acts on the IGF1R and AKT within 1 hour to block the signaling cascade and confers Ser-phosphorylation and degradation of IRS1 and IRS2 2-8 hours after exposure to achieve long-term inhibitory effect.

To further scrutinize the effect of compound no. 39 on IGF1 signaling, the rate of phosphorylation of the kinase AKT, a major and well-established downstream target of the pathway whose phosphorylation is a prerequisite for its activation in various tissues including the brain, was examined. Compound no. 39 treatment abolished the IGF1-induced activation of AKT after short and long exposures, demonstrated by the inhibition of AKT phosphorylation on threonine 308 and serine 473 (FIGS. 4B and C, lanes 4-6).

To explore the temporal order of events consequently to the addition of compound no. 39 to the cell media, a kinetic experiment was performed in which the cells were treated for the indicated times (FIG. 4D, 0.5-8 hours), stimulated with IGF1 for 5 min and subjected to WB. The results show that partial inhibition of IGF1R auto-phosphorylation is achieved merely half an hour after the addition of the drug, leading to a partial inhibition of AKT phosphorylation (FIG. 4D). Significant and long-term inhibition of AKT activation is attained when the second inhibitory mechanism, involving serine-phosphorylation and subsequent degradation of IRS1 and IRS2, occurs.

Together, the results indicate that compound no. 39 is an efficient IGF1 signaling inhibitor which acts by a dual step mechanism; (i) reducing the auto-phosphorylation and activation of the IGF1R to achieve an immediate inhibitory effect and (ii) induction of IRS1 and IRS2 phosphorylation on multiple serine residues, leading to their degradation, conferring a long term blockage of the IGF1 to AKT pathway.

Elevated Expression of IIS-Regulated Genes in Compound 39-Treated Worms

Figure 5:
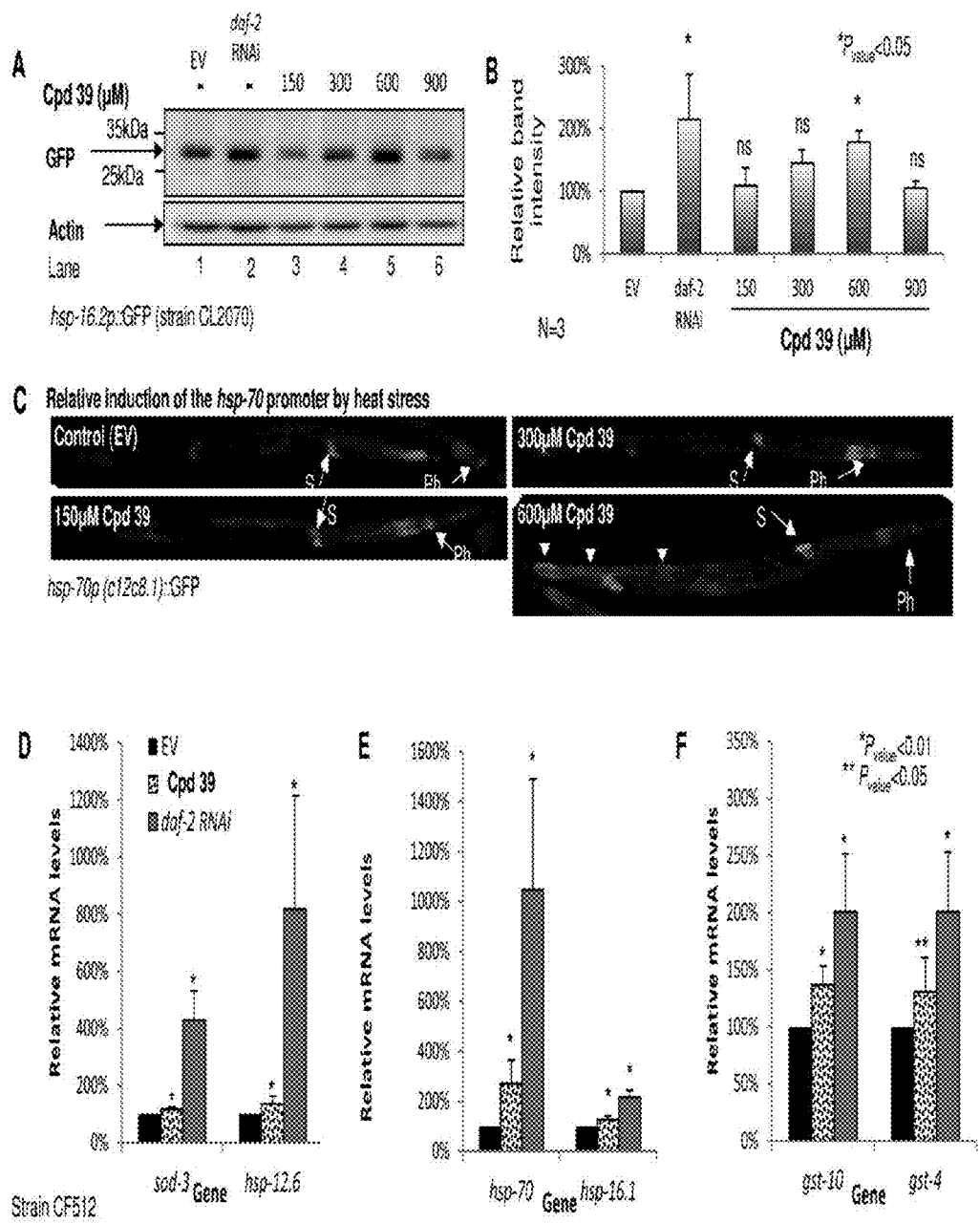
FIG. 5: Compound no. 39 activates the expression of IIS target genes. A. Worms expressing GFP under the regulation of the hsp-16.2 promoter (strain CL2070) were treated for 3 hours at days 1 and 2 of adulthood with the indicated Compound 39 concentrations. Western blot analysis shows that Compound 39 activates the hsp-16.2 promoter in a concentration dependent manner up to 600 μM. CL2070 worms that were treated with 900 μM Compound 39 exhibited lower activation rate compared to the level seen in their counterparts treated with 600 μM. B. Three independent experiments confirmed the significance of the results presented in (A). C. 600 μM Compound 39, but not lower concentrations of the compound, elevates the expression level of GFP driven by the hsp-70 promoter after exposure to heat stress (33° C., 3 h) as visualized by fluorescent microscopy. This effect was foremost prominent in the intestine (arrowheads)("Ph"—pharynx, "S"—spermatheca).

IIS reduction was shown to elevate the induction rate of the HSF-1 target gene hsp-16.2, upon exposure to heat beyond the induction level of untreated animals (Hsu et al, 2003; McColl et al, 2010). This feature was exploited to assess whether compound no. 39 is capable of reducing the activity of the IIS in *C. elegans*, employing worms that express the Green Fluorescent Protein (GFP) under the regulation of the hsp-16.2 promoter (strain CL2070). CL2070 worms were grown on control bacteria (harboring the empty vector (EV)). The animals were divided to identical groups and treated at days 1 and 2 of adulthood for three hours with either the chemical solvent of compound no. 39 (FIG. 5A, lane 1 (EV)), or with 150, 300, 600 or 900 µM compound no. 39 (lanes 2-6 respectively). An identical worm group was grown from hatching on daf-2 RNAi bacteria (lane 2). At day 2 of adulthood all worm groups were exposed to 33° C. for three hours, harvested and GFP levels were analyzed by WB analysis. The results indicated that compound no. 39 increased the hsp-16.2 induction levels in heat-stressed animals in a dose dependent manner. While treatment with 150 µM compound no. 39 had no detectable effect on the level of GFP, 300 µM had a moderate effect and 600 µM compound no. 39 remarkably increased the induction of GFP to a level similar to that seen in daf-2 RNAi-treated animals. Interestingly, treatment with 900 µM compound no. 39 had lower effect than that of 600 µM of the drug (FIG. 5B).

Further experiments tested whether compound no. 39 affects the induction of Hsp-70 by treating worms that express GFP under the control of the hsp-70 promoter (hsp-70p::GFP) with the vehicle (EV), compound no. 39 or daf-2 RNAi, exposing them to heat stress as described above and visualizing them by fluorescent microscopy. An increase in GFP signal was observable as worms treated with 600 µM compound no. 39, exhibited elevated GFP fluorescence levels (FIG. 5C, 600 µM compound no. 39 arrowheads).

Together these observations indicate that compound no. 39 inhibits the IIS, hyper-activates DAF-16 and HSF-1 and elevates the activity of the IIS-regulated genes and suggest that treatment with 600 µM compound no. 39 is preferable to achieve these effects. Thus, this compound no. 39 concentration was for the worm-based experiments described below.

To further establish these observations, quantitative real-time PCR (qPCR) and specific primer sets were used to measure the expression levels of DAF-16, HSF-1 and SKN-1 target genes. In this set of experiments temperature sensitive sterile worms were used (strain CF512) that lack progeny when exposed to 25° C. during development. The infertility of these animals enabled to examine the expression levels of IIS-target genes in adult worms with no background of gene expression in developing embryos. The worms were grown on EV bacteria and treated for 3 hours with 600 µM compound no. 39 at days 1 and 2 of adulthood. An identical group of worms was treated with the chemical vehicle (EV) and a third group was grown on daf-2 RNAi bacteria. qPCR reactions were performed using primer sets towards the DAF-16 target genes sod-3 and hsp-12.6 (Murphy et al, 2003), the HSF-1 regulated genes hsp-16.1 (Link et al, 1999) and hsp-70 (Snutch et al, 1988) and the SKN-1 controlled genes gst-4 and gst-10 (Wang et al, 2010). Three independent experiments indicated that compound no. 39 (FIG. 5, D-F, spotted bars) elevates the expression levels of all target genes compared to the levels seen in the control group (black bars). Yet, while DAF-16 (D) and SKN-1 (E) target genes exhibited average increase levels of 19-37%, the expression level of hsp-70 was elevated by approximately 170% (F). This observation proposes that compound no. 39 differentially affects the activity levels of the IIS-regulated transcription factors, displaying a more prominent effect on activating HSF-1. In all cases, the knockdown of daf-2 by RNAi (gray bars) resulted in larger increase in the expression of the tested genes compared to compound no. 39 treatment (spotted bars).

Alleviated Proteotoxicity in Compound No. 399-Treated Model Nematodes

The findings that compound no. 39 treatment reduces the activity of the IIS have led to the hypothesis that this compound can protect worms from Aβ aggregation-mediated toxicity. To examine this hypothesis Aβ worms and the paralysis assay were employed (Cohen et al, 2006), as described above in Example 2. The worms were developed on EV bacteria and soaked for 3 hours at days 1 and 2 of adulthood in either 600 µM compound no. 39 or in the chemical vehicle (EV). From day 3 of adulthood up until the termination of the experiment each worm group was supplemented daily with the same compound as treated at days 1 and 2 of adulthood. An additional worm group was grown throughout development and adulthood on daf-2 RNAi bacteria. While the rates of paralyzed worms within the control group (EV) reached 53% at day 12, daily compound no. 39 treatment reduced the rate of paralysis to merely 29% at the same age. The rate of paralysis within the daf-2 RNAi-treated animals was only 9% (FIG. 6A). Four independent experiments confirmed the significance of this phenomenon (FIG. 6B, $P_{value}$<0.01).

Since IIS inhibition protects Aβ worms by hyper-aggregating Aβ oligomers (Cohen et al, 2006) it was next investigated whether compound no. 39 acts through a similar mechanism. Aβ worms that were grown on control bacteria (EV) were either left untreated or treated with compound no. 39, as described above. A third worm group was grown from hatching until day 2 of adulthood on daf-2 RNAi bacteria. The worms were homogenized, cleared and subjected to high-speed centrifugation. Aβ structures in the post debris supernatants (PDS) were analyzed by WB using an Aβ antibody (clone 6E10). Similarly to daf-2 RNAi, compound no. 39-treated worms contained an elevated amount of high molecular-weight Aβ aggregates compared to control animals (FIG. 6C). Since it was found previously that the knockdown of daf-2 by RNAi results in the accumulation of Aβ in the center of the worm's body (Cohen et al, 2006) it was investigated whether a similar phenomenon occurs in compound no. 39-treated animals.

To address this question, Aβ amounts and distribution in compound no. 39- or daf-2 RNAi-treated Aβ worms were analyzed by immuno-fluorescence. The results showed that both treatments enhanced the amount of Aβ and led to its accumulation in the central part of the animal's body (FIG. 6D, arrows), supporting the notion that they activate the same protective mechanism.

To assess whether compound no. 39 also protects from disease-linked, aggregative proteins other than A, worms that express polyQ stretches of either 35 or 40 repeats fused to the Yellow Fluorescent Protein (YFP) in their body wall muscles (strains polyQ35-YFP and polyQ40-YFP respectively) were employed. The expression of either one of the polyQ-YFP constructs leads to the accumulation of aggregates in visible foci and to reduced motility in an aging dependent manner. These phenomena can be delayed by IIS reduction (Morley et al, 2002).

To assess whether compound no. 39 affects the number of aggregate-containing foci in polyQ40-YFP worms, the fluorescent dots in at least seventy animals of each of the following groups were counted: worms that were grown on EV bacteria and treated with either (i) compound no. 39 or (ii) the vehicle (EV) at days 1 and 2 of adulthood, as well as in worms that were grown on (iii) daf-2 RNAi (FIG. 7A). The average number of foci per worm in the compound no. 39-treated group was significantly lower compared to the animals of the control group (FIG. 7B, *$P_{value}$<0.01) but higher than in the daf-2 RNAi treated animals.

It was also examined whether compound no. 39 mitigates polyQ35-YFP aggregation-mediated motility impairment by measuring the crawling speed of young (day 1) and old (day 11) polyQ35-YFP animals that were treated daily from day 1 of adulthood either with compound no. 39, with the chemical vehicle (EV) or grown on daf-2 RNAi. As an additional control we measured the average crawling speed of untreated worms that solely express YFP in their muscles (polyQ0-YFP). The measurements were performed by an automated system that followed 56 animals per group. The results (FIG. 7C) clearly show that while the crawling speed of untreated, 11 days old polyQ35-YFP was only 8.8% compared to their speed at day 1 of adulthood, their compound no. 39-treated counterparts were largely rescued from the motility impairment associated with the aggregation of polyQ35-YFP. Animals of the latter group exhibited crawling speeds similar to these of polyQ0-YFP animals (32.9% and 31.8% respectively) indicating that compound no. 39 largely abolished the toxic effect of polyQ35-YFP aggregation. As seen in Aβ worms, the protective effect provided by compound no. 39 was less prominent than that conferred by daf-2 RNAi.

To explore the mechanism by which compound no. 39 protects from polyQ aggregation we subjected poly40-YFP worms to compound no. 39 or daf-2 RNAi treatment as above, homogenized them at day 2 of adulthood and analyzed the quantities of SDS resistant polyQ40-YFP aggregates using WB and a GFP antibody. While highly aggregated molecules were apparent in homogenates of daf-2 RNAi treated worms, no such material could be detected in homogenates of untreated and of compound no. 39-treated animals (FIG. 7D). Analogous results were obtained when homogenates were prepared as above and supernatants were separated from pellets by high-speed centrifugation and analyzed by WB. While treatment with daf-2 RNAi resulted in increased amounts of aggregated polyQ40-YFP compared to untreated animals (EV), no increase was seen in compound no. 39-treated animals (FIG. 7E).

To further scrutinize the effect of compound no. 39 on the amount of polyQ40-YFP aggregates we analyzed the amounts of polyQ40-YFP aggregates using native gels. PolyQ40-YFP animals were grown and treated with either the vehicle (EV), compound no. 39 or daf-2 RNAi, homogenized and loaded onto a 1% native gel that preserves polyQ40-YFP aggregates and enables YFP to fluoresce (van Ham et al, 2010). YFP fluorescence levels were visualized and compared. The results (FIG. 7F) indicated that in contrary to daf-2 RNAi treatment, compound no. 39-treated worms did not exhibit elevated rates of polyQ40-YFP aggregation as indicated by the low fluorescence levels compared to the these observed in untreated animals.

Together these observations propose that although both daf-2 RNAi and compound no. 39 protect worms from polyQ40 aggregation-mediated toxicity, these treatments confer their protective effects by differentially modulating the disaggregation and hyper-aggregation mechanisms of the worm.

Increased Rate of PrP Aggregation in Cells Treated with Cyclosporine-A and Compound No. 39

The aggregation of the prion protein (PrP) underlies the development of several neurodegenerative disorders including the familial Gerstmann-Sträussler-Scheinker syndrome (GSS). The substitution of the proline residue in either position 102 or 105 in the sequence of PrP leads to the development of GSS by preventing folding chaperone members of the cyclophilin family from assisting the protein attaining its correct spatial structure. Similarly, the inhibition of cyclophilins by the specific drug cyclosporin-A (CsA) leads to the misfolding and deposition of wild-type PrP in cellular deposition sites known as "aggresomes". CsA-induced PrP aggresomes are dynamic quality control cellular compartments that enable the clearance of misfolded PrP molecules. To test whether compound no. 39 affects the PrP aggregation and deposition following CsA-treatment Chinese Hamster Ovary cells which stably express the MHM2 PrP construct (CHO-M cells) (Scott et al, 1992) were employed. CHO-M cells were either treated with ethanol (EtOH, the vehicle of CsA), 60 µg/ml CsA, the compound no. 39 vehicle (Veh), CsA and the vehicle, 3 µM compound no. 39 or both CsA and compound no. 39. The cells were homogenized and subjected to high-speed centrifugation. PrP was blotted in supernatants and pellets by WB and a specific antibody. While CsA- and compound no. 39-treated cells exhibited elevated PrP quantities in both supernatants and pellets (FIGS. 8, A and B respectively, lanes 2, 4 and 5) compared to control cells (lanes 1 and 3) the combination of both drugs resulted in reduced amounts of soluble PrP molecules (FIG. 8A, lane 6) and elevated quantities of aggregated PrP (FIG. 8B, lane 6 arrow). Importantly, treatment with compound no. 39 induced the hyper-aggregation of PrP molecules solely when the cells were also treated with CsA (FIG. 8B, compare lanes 5 and 6), suggesting that the inhibition of IGF1 signaling by the compound primarily enhances hyper-aggregation of misfolded, potentially toxic PrP molecules but not of their soluble counterparts. This proposes that, similarly to the hyper-aggregation of Aβ by the knockdown of daf-2 in the worm (Cohen et al, 2006), compound no. 39 acts to sequester toxic misfolded PrP molecules from the cell by inducing their aggregation and deposition in aggresomes.

To examine whether PrP-containing aggresomes of cells that were treated with both CsA and compound no. 39 (60 µg/ml and 3 µM respectively) occupy larger areas than these of cells that were treated solely with CsA, an immunofluorescence analysis was performed. The results (FIG. 8C) indicated that aggresomes of cells that were treated with both drugs were bigger in size than these of CsA-treated cells. Quantification of at least eighty cells per treatment (FIG. 8D) confirmed the enlargement of aggresomes in cells that were treated with CsA and compound no. 39, supporting the concept that compound no. 39 enhances the aggregation and deposition of misfolded molecules in mammalian cells.

Elevated Resistance to Heat and to Ultra-Violet Radiation Exhibited by Compound No. 39-Treated Worms The ability of compound no. 39 to elevate resistance to heat stress was examined. CF512 worms that were grown on EV bacteria to day 1 of adulthood were divided to two identical groups. One group was treated with the chemical vehicle (EV) while the other was treated with compound no. 39 for 3 hours at days 1 and 2 of adulthood. A third group was grown on daf-2 RNAi bacteria throughout development and during day 1 of adulthood. Worms of all groups were exposed to 35° C. and rates of survival within the worm populations were scored after 15 hours of exposure. Results of four independent experiments (FIG. 9A) indicated that compound no. 39 treatment raised the survival rates within the worm populations by 33% compared to the untreated population (survival rates of 54% and 72% for untreated and compound no. 39-treated animals respectively, $P_{value}=0.008$). In the control group of daf-2 RNAi treated worms, an average of 85% survived the heat shock.

Next it was examined whether compound no. 39 treatment elevates the worms resistance to DNA damage by ultraviolet (UV) radiation, a feature of IIS reduction (Murakami & Johnson, 1996). To address that, two groups of CF512 worms were grown on EV bacteria. At day 1 of adulthood the worms were treated with either the vehicle (EV) of compound no. 39 and exposed to sub-lethal UV dose. The vehicle or compound no. 39 treatments were continued throughout the experiment by a daily supplementation and the worms' survival rates were recorded daily. A third group of worms was grown throughout development and adulthood on daf-2 RNAi bacteria. Compound no. 39 significantly elevated the rate of survival of UV-radiated worms (FIG. 9B, mean survival rates (days±SEM): EV 7.03±0.22, Compound no. 39-treated 8.76±0.21 $P_{value}=2.36E-8$). As observed for heat stress, the effect of compound no. 39 on the survival of UV-radiated animals was less prominent than that of daf-2 RNAi treatment (average survival 13.89±0.41 days).

Compound No. Has No Effect on the Nematode's Lifespan

Since longevity is also a hallmark characteristic of IIS reduction (Kenyon et al, 1993) it was next tested whether compound no. 39 influences the worms' lifespan. CF512 worms were treated with compound no. 39 in two regimes; in the first setup EV bacteria-grown worms were soaked for three hours in either compound no. 39 or the vehicle in days 1 and 2 of adulthood. The worms were then transferred onto plates spotted with EV bacteria and supplemented daily with either the vehicle or the drug. A third group of worms was fed daf-2 RNAi bacteria throughout life. Since IIS reduction regulates lifespan exclusively during reproductive adulthood, a second experiment was performed in which the worms' exposure to the drug was maximized during this period of their lifecycle. EV bacteria-grown CF512 worms were treated daily with either 600 μM compound no. 39 or the vehicle during reproductive adulthood (days 1 to 6 of adulthood). At day 6 the worms were split onto plates seeded with EV bacteria and lifespans were recorded daily. Worms that were treated with daf-2 RNAi throughout life served as a control group. Surprisingly, in both setups compound no. 39-treated and untreated worm populations exhibited indistinguishable lifespans indicating that compound no. 39 has no effect on lifespan (FIG. 9C).

Similarly, the mean lifespan of wild-type (strain $N_2$) worm population that was treated daily with compound no. 39 was indistinguishable from that of their untreated counterparts (FIG. 9D).

DISCUSSION

The therapeutic potential of IIS inhibition as a treatment for neurodegenerative maladies has been demonstrated. As demonstrated herein, the IIS inhibitor, compound no. 39, exhibits counter-proteotoxic activity and can potentially serve as a drug to treat neurodegenerative disorders. Employing model nematodes we found that compound no. 39 mitigates the toxic effects that stem from neurodegeneration-linked protein aggregation. Similarly, the drug enhances the aggregation of misfolded PrP and leads to their deposition in quality control deposition sites. It was further found that compound no. 39 efficiently blocks IGF1R to AKT signaling in mammalian cells by a dual step mechanism. It reduces the auto-phosphorylation of the IGF1R to prevent the phosphorylation and activation of AKT and induces a negative feedback loop, directing IRS1/2, major components of this pathway, for degradation (Boura-Halfon & Zick, 2009). Compound no. 39 was also found to increase the expression levels of target genes downstream of all three known IIS-regulated transcription factors of the nematode C. elegans, DAF-16, HSF-1 and SKN-1 and to elevate the nematode's resistance to heat and UV radiation. compound no. 39 had no effect on nematodes' lifespans.

The indications that compound no. 39 protects from the toxicity of two neurodegeneration-linked, aggregative peptides, Aβ and polyQ35-YFP, in worms and enhances the deposition of misfolded PrP in aggresomes, show that this compound has the potential to combat more than one neurodegenerative disorder. The lack of effect on lifespan promises to inhibit the progression of neurodegeneration rather than postponing it to later stages of life.

In conclusion, this study supports the notion that longevity and protection from aging-associated diseases are separable and strengthens the theme that selective aging manipulations by small molecules that inhibit the IIS bears the promise to efficiently delay the emergence and slow the progression of late-onset neurodegenerative maladies.

While certain embodiments of the invention have been illustrated and described, it is to be clear that the invention is not limited to the embodiments described herein. Numerous modifications, changes, variations, substitutions and equivalents will be apparent to those skilled in the art without departing from the spirit and scope of the present invention as described by the claims, which follow.

ADDITIONAL REFERENCES

Boura-Halfon S, Zick Y (2009) Serine kinases of insulin receptor substrate proteins. *Vitam Horm* 80: 313-349

Cohen E, Bieschke J, Perciavalle R M, Kelly J W, Dillin A (2006) Opposing activities protect against age-onset proteotoxicity. *Science* (New York, N.Y. 313: 1604-1610

Favelyukis S, Till J H, Hubbard S R, Miller W T (2001) Structure and autoregulation of the insulin-like growth factor 1 receptor kinase. *Nat Struct Biol* 8: 1058-1063

Hsu A L, Murphy C T, Kenyon C (2003) Regulation of aging and age-related disease by DAF-16 and heat-shock factor. *Science* (New York, N.Y. 300: 1142-1145

Link C D, Cypser J R, Johnson C J, Johnson T E (1999) Direct observation of stress response in *Caenorhabditis elegans* using a reporter transgene. *Cell Stress Chaperones* 4: 235-242

Morley J F, Brignull H R, Weyers J J, Morimoto R I (2002) The threshold for polyglutamine-expansion protein aggregation and cellular toxicity is dynamic and influenced by aging in *Caenorhabditis elegans*. *Proceedings of the National Academy of Sciences of the United States of America* 99: 10417-10422

Murphy C T, McCarroll S A, Bargmann C I, Fraser A, Kamath R S, Ahringer J, Li H, Kenyon C (2003) Genes that act downstream of DAF-16 to influence the lifespan of *Caenorhabditis elegans*. *Nature* 424: 277-283

Scott M R, Kohler R, Foster D, Prusiner S B (1992) Chimeric prion protein expression in cultured cells and transgenic mice. *Protein Sci* 1: 986-997

Snutch T P, Heschl M F, Baillie D L (1988) The *Caenorhabditis elegans* hsp70 gene family: a molecular genetic characterization. *Gene* 64: 241-255 van Ham T J, Holmberg M A, van der Goot A T, Teuling E, Garcia-Arencibia M, Kim H E, Du D, Thijssen K L, Wiersma M, Burggraaff R, van Bergeijk P, van Rheenen J, Jerre van Veluw G, Hofstra R M, Rubinsztein D C, Nollen E A (2010) Identification of MOAG-4/SERF as a regulator of age-related proteotoxicity. *Cell* 142: 601-612

Wang J, Robida-Stubbs S, Tullet J M, Rual J F, Vidal M, Blackwell T K (2010) RNAi screening implicates a SKN-1-dependent transcriptional response in stress resistance and longevity deriving from translation inhibition. *PLoS Genet* 6

The invention claimed is:

1. A method of inhibiting toxic protein aggregation in a subject having a neurodegenerative disease selected from the group consisting of Amyloidosis, Prion disorders, Motor Neuron disease, Alzheimer's disease, Fronto temporal dementia 17 (FTD17), Huntington disease and Parkinson's disease, the method comprising the step of administering to the subject a therapeutically effective amount of a compound represented by the structure of formula IV:

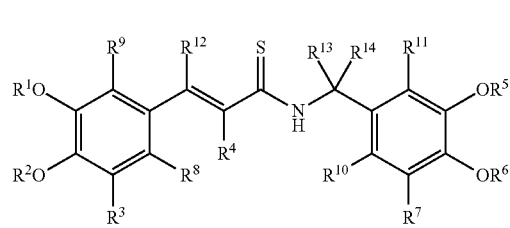

(IV)

wherein
$R^1$, $R^2$, $R^5$ and $R^6$ are independently selected from the group consisting of H, $(CH_2CH_2O)_n$, wherein n is an integer of 1 to 20, acyl and a functional group that gives rise to hydroxyl upon hydrolysis;
$R^3$, $R^7$, $R^8$, $R^9$, $R^{10}$, $R^{11}$, $R^{12}$, $R^{13}$ and $R^{14}$ are independently selected from the group consisting of H, halogen, $C_1$-$C_4$ alkyl, haloalkyl and $OR^{16}$ wherein $R^{16}$ is H, $C_1$-$C_4$ alkyl, $(CH_2CH_2O)_n$, acyl or a functional group that gives rise to hydroxyl upon hydrolysis; and
$R^4$ is H or CN;
and salts, hydrates and solvates thereof.

2. The method of claim 1, wherein the compound is represented by the structure of formula III:

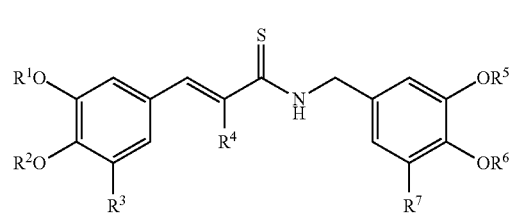

(III)

wherein
$R^1$, $R^2$, $R^5$ and $R^6$ are independently selected from the group consisting of H, $(CH_2CH_2O)_n$, wherein n is an integer of 1 to 20, acyl and a functional group that gives rise to hydroxyl upon hydrolysis;
$R^3$ and $R^7$ are independently selected from the group consisting of H, halogen, $C_1$-$C_4$ alkyl, haloalkyl and $OR^{16}$ wherein $R^{16}$ is H, $C_1$-$C_4$ alkyl, $(CH_2CH_2O)_n$, acyl or a functional group that gives rise to hydroxyl upon hydrolysis; and
$R^4$ is H or CN;
and salts, hydrates and solvates thereof.

3. The method of claim 1, wherein the compound is selected from the group consisting of:

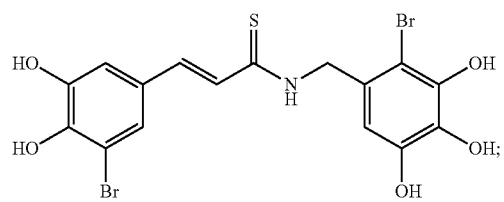

9

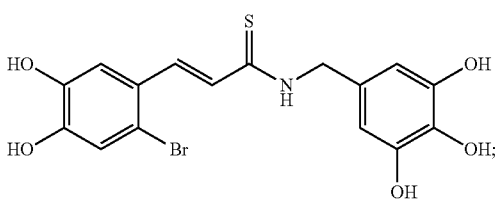

11

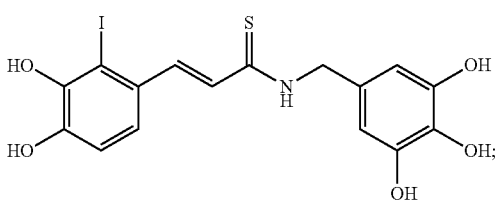

12

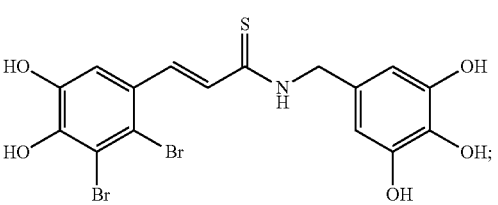

13a

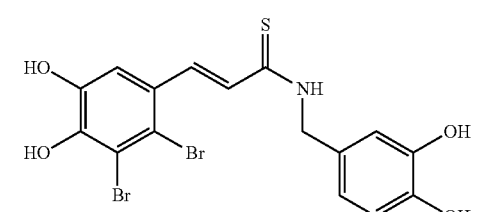

13b

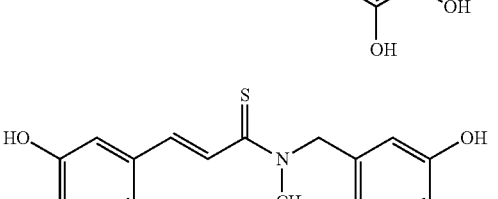

14a

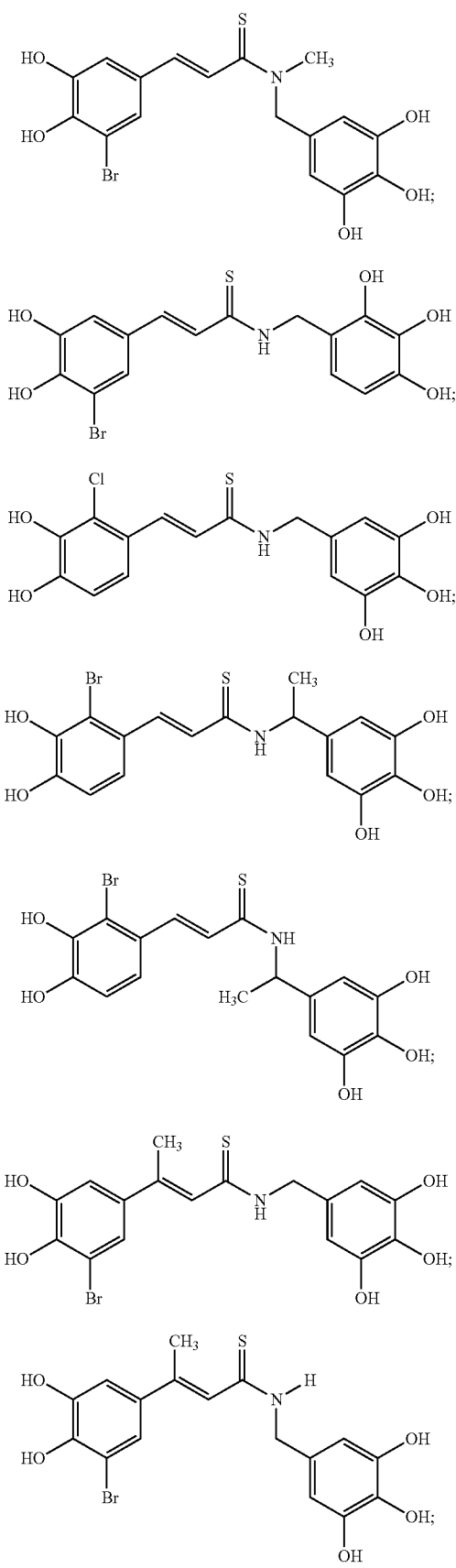
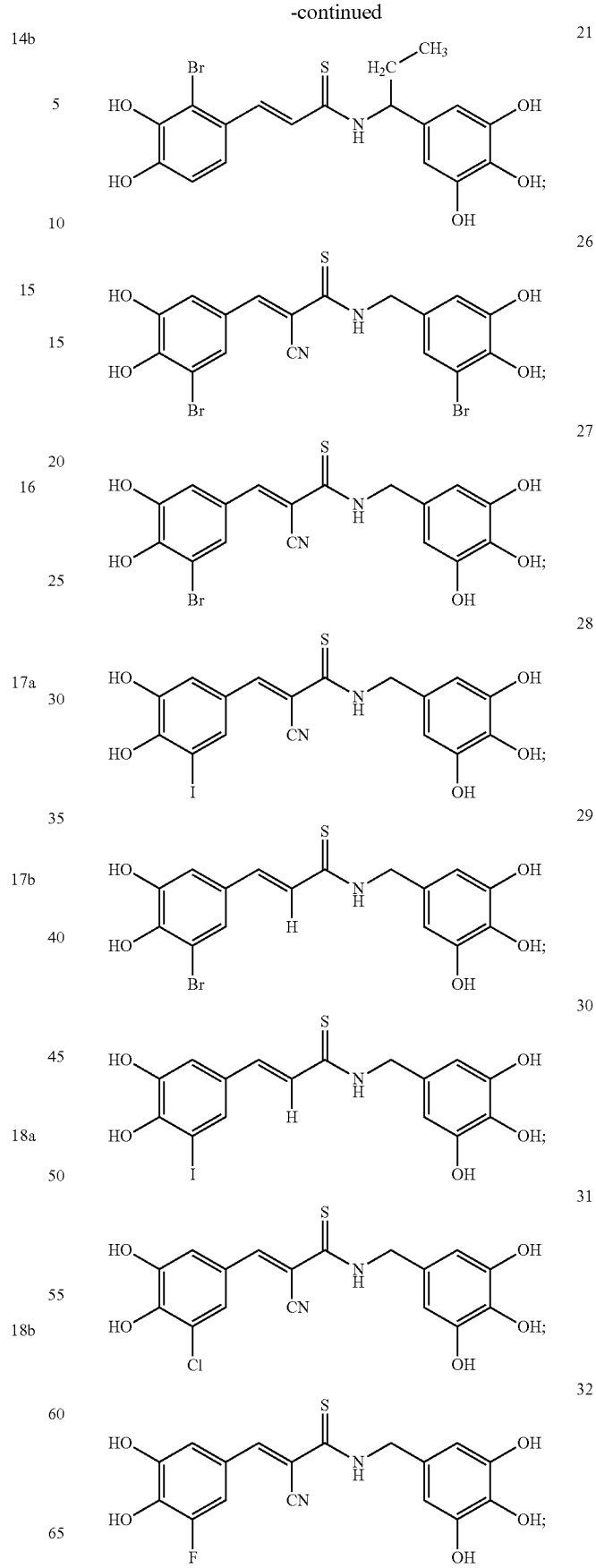

33

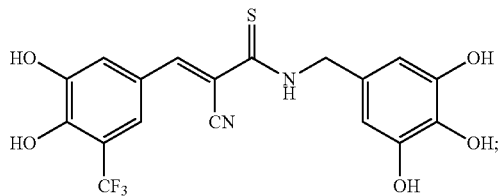

34

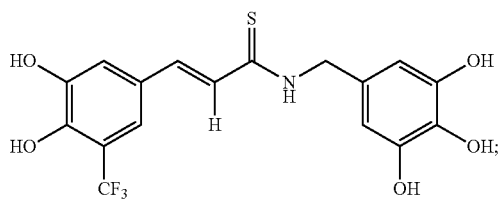

35

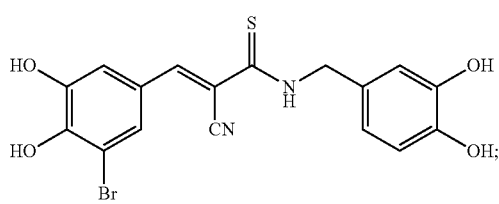

36

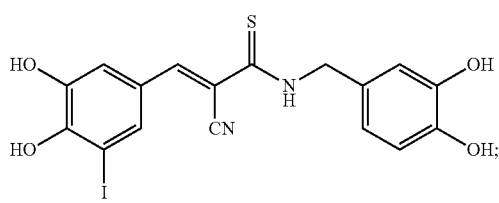

37

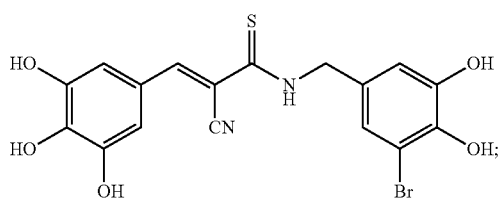

38

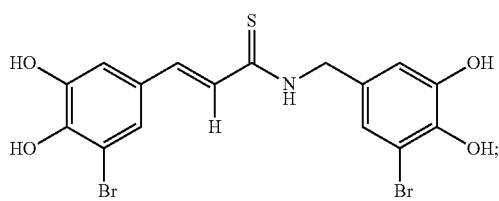

39

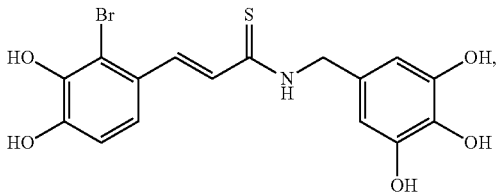

and salts, hydrates and solvates thereof.

4. The method of claim 3, comprising administering to the subject a therapeutically effective amount of compound no. 39 or salts, hydrates or solvates thereof.

5. The method of claim 3, comprising administering to the subject a therapeutically effective amount of compound no. 29 or salts, hydrates or solvates thereof.

6. The method of claim 1, wherein Amyloidosis is selected from the group consisting of AL amyloidosis, AA amyloidosis, familial amyloid polyneuropathies, senile systemic amyloidosis, Leptomeningeal amyloidosis, Haemodialysis-associated amyloidosis, Finnish type amyloidosis, Cerebral amyloid angiopathy; Familial visceral amyloidosis; Familial corneal amyloidosis; Primary cutaneous amyloidosis and Senile amyloid of atria of heart.

7. The method of claim 1, wherein the prion disorders are selected from the group consisting of Finnish type amyloidosis; Creutzfeldt-Jakob disease, fatal familial insomnia (FFI) and Gerstmann-Straussler-Scheinker syndrome (GSS).

8. The method of claim 1, wherein the neurodegenerative disease is caused by toxic amyloid beta (Aβ) aggregation.

9. The method of claim 8, wherein the neurodegenerative disease is Alzheimer's disease.

10. The method of claim 1, wherein the compound inhibits Insulin/IGF signaling cascade (IIS).

11. The method of claim 1, wherein the compound is compound no. 39 or salts, hydrates and solvates thereof, and wherein the neurodegenerative disease is Alzheimer's disease.

12. The method of claim 1, wherein the compound is compound no. 39 or salts, hydrates and solvates thereof, and wherein the neurodegenerative disease is selected from the group consisting of Alzheimer's disease, Huntington's disease, and Prion disorders.

* * * * *

UNITED STATES PATENT AND TRADEMARK OFFICE
CERTIFICATE OF CORRECTION

PATENT NO. : 9,770,454 B2
APPLICATION NO. : 14/904787
DATED : September 26, 2017
INVENTOR(S) : Reuveni et al.

It is certified that error appears in the above-identified patent and that said Letters Patent is hereby corrected as shown below:

In the Claims

Column 59, Line 44, delete "$(CH_2CH_2O)n$" and insert --$(CH_2CH_2O)_nH$--

Column 59, Line 50, delete "$(CH_2CH_2O)n$" and insert --$(CH_2CH_2O)_nH$--

Signed and Sealed this
Thirty-first Day of July, 2018

Andrei Iancu
*Director of the United States Patent and Trademark Office*